United States Patent [19]
von der Osten et al.

[11] Patent Number: 6,015,783
[45] Date of Patent: Jan. 18, 2000

[54] PROCESS FOR REMOVAL OR BLEACHING OF SOILING OR STAINS FROM CELLULOSIC FABRIC

[75] Inventors: Claus von der Osten, Lyngby, Denmark; Joel R. Cherry, Davis, Calif.; Mads E. Bjornvad, Frederiksberg, Denmark; Jesper Vind, Lyngby, Denmark; Michael Dolberg Rasmussen, Vallensbaek, Denmark

[73] Assignee: Novo Nordisk A/S, Bagsvaerd, Denmark

[21] Appl. No.: 08/814,052

[22] Filed: Mar. 6, 1997

Related U.S. Application Data

[63] Continuation of application No. PCT/DK97/00042, Jan. 29, 1997.

[30] Foreign Application Priority Data

Jan. 29, 1996 [DK] Denmark ................................ 0094/96

[51] Int. Cl.$^7$ ................................................. C11D 3/386
[52] U.S. Cl. ............................................................ 510/392
[58] Field of Search .................................... 435/263, 264, 435/209; 8/137, 401; 510/392, 393, 320, 321

[56] References Cited

U.S. PATENT DOCUMENTS

| | | | |
|---|---|---|---|
| 5,525,193 | 6/1996 | Franks et al. | 162/5 |
| 5,536,655 | 7/1996 | Thomas et al. | 435/209 |
| 5,578,489 | 11/1996 | Petersen | 435/263 |

FOREIGN PATENT DOCUMENTS

| | | |
|---|---|---|
| 90/00609 | 1/1990 | WIPO . |
| 91/10732 | 6/1991 | WIPO . |
| WO 91/17244 | 11/1991 | WIPO . |
| WO 93/05226 | 3/1993 | WIPO . |
| WO 93/11249 | 6/1993 | WIPO . |
| 94/07998 | 4/1994 | WIPO . |
| 94/24158 | 10/1994 | WIPO . |
| 95/16782 | 6/1995 | WIPO . |
| WO 96/13524 | 5/1996 | WIPO . |
| 97/28243 | 8/1997 | WIPO . |
| 97/28256 | 8/1997 | WIPO . |

OTHER PUBLICATIONS

Greenwood, J.M., et al., Biotechnology & Bioengineering, accession No. 11434006, vol. 44 (11), pp. 1295–1305 (1994).

Chalfie et al. (1994) Science 263:802–805.

*Primary Examiner*—Kery Fries
*Attorney, Agent, or Firm*—Steve T. Zelson, Esq.; Reza Green, Esq.

[57] ABSTRACT

The present invention relates to a process for removal or bleaching of soiling or stains present on cellulosic fabric, wherein the fabric is contacted in aqueous medium with a modified enzyme (enzyme hybrid) which comprises a catalytically active amino acid sequence of a non-cellulolytic enzyme linked to an amino acid sequence comprising a cellulose-binding domain. The invention further relates to a detergent composition comprising an enzyme hybrid of the type in question and a surfactant, and to a process for washing soiled or stained cellulosic fabric, wherein the fabric is washed in an aqueous medium to which is added such a detergent composition.

11 Claims, No Drawings

SEQUENCE LISTING (1) GENERAL INFORMATION:

(iii) NUMBER OF SEQUENCES: 55

(2) INFORMATION FOR SEQ ID NO: 1:

(i) SEQUENCE CHARACTERISTICS:
      (A) LENGTH: 2253 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

```
ATGAAACAAC AAAAACGGCT TTACGCCCGA TTGCTGACGC TGTTATTTGC GCTCATCTTC        60

TTGCTGCCTC ATTCTGCAGC AGCGGCGGCA AATCTTAATG GGACGCTGAT GCAGTATTTT       120

GAATGGTACA TGCCCAATGA CGGCCAACAT TGGAAGCGTT TGCAAAACGA CTCGGCATAT       180

TTGGCTGAAC ACGGTATTAC TGCCGTCTGG ATTCCCCCGG CATATAAGGG AACGAGCCAA       240

GCGGATGTGG GCTACGGTGC TTACGACCTT TATGATTTAG GGGAGTTTCA TCAAAAAGGG       300

ACGGTTCGGA CAAAGTACGG CACAAAAGGA GAGCTGCAAT CTGCGATCAA AAGTCTTCAT       360

TCCCGCGACA TTAACGTTTA CGGGGATGTG GTCATCAACC ACAAAGGCGG CGCTGATGCG       420

ACCGAAGATG TAACCGCGGT TGAAGTCGAT CCCGCTGACC GCAACCGCGT AATCTCAGGA       480

GAACACCTAA TTAAAGCCTG GACACATTTT CATTTTCCGG GGGCCGGCAG CACATACAGC       540

GATTTTAAAT GGCATTGGTA CCATTTTGAC GGAACCGATT GGGACGAGTC CCGAAAGCTG       600
```

-continued

```
AACCGCATCT ATAAGTTTCA AGGAAAGGCT TGGGATTGGG AAGTTTCCAA TGAAAACGGC    660

AACTATGATT ATTTGATGTA TGCCGACATC GATTATGACC ATCCTGATGT CGCAGCAGAA    720

ATTAAGAGAT GGGGCACTTG GTATGCCAAT GAACTGCAAT GGACGGAAA CCGTCTTGAT    780

GCTGTCAAAC ACATTAAATT TTCTTTTTTG CGGGATTGGG TTAATCATGT CAGGGAAAAA    840

ACGGGGAAGG AAATGTTTAC GGTAGCTGAA TATTGGCAGA ATGACTTGGG CGCGCTGGAA    900

AACTATTTGA ACAAAACAAA TTTTAATCAT TCAGTGTTTG ACGTGCCGCT TCATTATCAG    960

TTCCATGCTG CATCGACACA GGGAGGCGGC TATGATATGA GGAAATTGCT GAACGGTACG    1020

GTCGTTTCCA AGCATCCGTT GAAATCGGTT ACATTTGTCG ATAACCATGA TACACAGCCG    1080

GGGCAATCGC TTGAGTCGAC TGTCCAAACA TGGTTTAAGC CGCTTGCTTA CGCTTTTATT    1140

CTCACAAGGG AATCTGGATA CCCTCAGGTT TTCTACGGGG ATATGTACGG GACGAAAGGA    1200

GACTCCCAGC GCGAAATTCC TGCCTTGAAA CACAAAATTG AACCGATCTT AAAAGCGAGA    1260

AAACAGTATG CGTACGGAGC ACAGCATGAT TATTTCGACC ACCATGACAT TGTCGGCTGG    1320

ACAAGGGAAG GCGACAGCTC GGTTGCAAAT TCAGGTTTGG CGGCATTAAT AACAGACGGA    1380

CCCGGTGGGG CAAAGCGAAT GTATGTCGGC CGGCAAAACG CCGGTGAGAC ATGGCATGAC    1440

ATTACCGGAA ACCGTTCGGA GCCGGTTGTC ATCAATTCGG AAGGCTGGGG AGAGTTTCAC    1500

GTAAACGGCG GATCCGTTTC AATTTATGTT CAAAGATCTG GCGGACCTGG AACGCCAAAT    1560

AATGGCAGAG GAATTGGTTA TATTGAAAAT GGTAATACCG TAACTTACAG CAATATAGAT    1620

TTTGGTAGTG GTGCAACAGG GTTCTCTGCA ACTGTTGCAA CGGAGGTTAA TACCTCAATT    1680

CAAATCCGTT CTGACAGTCC TACCGGAACT CTACTTGGTA CCTTATATGT AAGTTCTACC    1740

GGCAGCTGGA ATACATATCA ACCGTATCTA CAAACATCAG CAAAATTACC GGCGTTCATG    1800

ATATTGTATT GGTATTCTCA GGTCCAGTCA ATGTGGACAA CTTCATATTT AGCAGAAGTT    1860

CACCAGTGCC TGCACCTGGT GATAACACAA GAGACGCATA TTCTATCATT CAGGCCGAGG    1920

ATTATGACAG CAGTTATGGT CCCAACCTTC AAATCTTTAG CTTACCAGGT GGTGGCAGCG    1980

CTTGGCTATA TTGAAAATGG TTATTCCACT ACCTATAAAA ATATTGATTT TGGTGACGGC    2040

GCAACGTCCG TAACAGCAAG AGTAGCTACC CAGAATGCTA CTACCATTCA GGTAAGATTG    2100

GGAAGTCCAT CGGGTACATT ACTTGGAACA ATTTACGTGG GGTCCACAGG AAGCTTTGAT    2160

ACTTATAGGG ATGTATCCGC TACCATTAGT AATACTGCGG GTGTAAAAGA TATTGTTCTT    2220

GTATTCTCAG GTCCTGTTAA TGTTGACTGG TAG                                 2253
```

(2) INFORMATION FOR SEQ ID NO: 2:

(i) SEQUENCE CHARACTERISTICS:
        (A) LENGTH: 750 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

```
Met Lys Gln Gln Lys Arg Leu Tyr Ala Arg Leu Leu Thr Leu Leu Phe
 1               5                  10                  15

Ala Leu Ile Phe Leu Leu Pro His Ser Ala Ala Ala Ala Asn Leu
                20                  25                  30

Asn Gly Thr Leu Met Gln Tyr Phe Glu Trp Tyr Met Pro Asn Asp Gly
            35                  40                  45

Gln His Trp Lys Arg Leu Gln Asn Asp Ser Ala Tyr Leu Ala Glu His
        50                  55                  60
```

```
Gly Ile Thr Ala Val Trp Ile Pro Pro Ala Tyr Lys Gly Thr Ser Gln
 65                  70                  75                  80

Ala Asp Val Gly Tyr Gly Ala Tyr Asp Leu Tyr Asp Leu Gly Glu Phe
                 85                  90                  95

His Gln Lys Gly Thr Val Arg Thr Lys Tyr Gly Thr Lys Gly Glu Leu
            100                 105                 110

Gln Ser Ala Ile Lys Ser Leu His Ser Arg Asp Ile Asn Val Tyr Gly
        115                 120                 125

Asp Val Val Ile Asn His Lys Gly Ala Asp Ala Thr Glu Asp Val
    130                 135                 140

Thr Ala Val Glu Val Asp Pro Ala Asp Arg Asn Arg Val Ile Ser Gly
145                 150                 155                 160

Glu His Leu Ile Lys Ala Trp Thr His Phe His Phe Pro Gly Ala Gly
                165                 170                 175

Ser Thr Tyr Ser Asp Phe Lys Trp His Trp Tyr His Phe Asp Gly Thr
            180                 185                 190

Asp Trp Asp Glu Ser Arg Lys Leu Asn Arg Ile Tyr Lys Phe Gln Gly
        195                 200                 205

Lys Ala Trp Asp Trp Glu Val Ser Asn Glu Asn Gly Asn Tyr Asp Tyr
    210                 215                 220

Leu Met Tyr Ala Asp Ile Asp Tyr Asp His Pro Asp Val Ala Ala Glu
225                 230                 235                 240

Ile Lys Arg Trp Gly Thr Trp Tyr Ala Asn Glu Leu Gln Leu Asp Gly
                245                 250                 255

Asn Arg Leu Asp Ala Val Lys His Ile Lys Phe Ser Phe Leu Arg Asp
            260                 265                 270

Trp Val Asn His Val Arg Glu Lys Thr Gly Lys Glu Met Phe Thr Val
        275                 280                 285

Ala Glu Tyr Trp Gln Asn Asp Leu Gly Ala Leu Glu Asn Tyr Leu Asn
    290                 295                 300

Lys Thr Asn Phe Asn His Ser Val Phe Asp Val Pro Leu His Tyr Gln
305                 310                 315                 320

Phe His Ala Ala Ser Thr Gln Gly Gly Gly Tyr Asp Met Arg Lys Leu
                325                 330                 335

Leu Asn Gly Thr Val Val Ser Lys His Pro Leu Lys Ser Val Thr Phe
            340                 345                 350

Val Asp Asn His Asp Thr Gln Pro Gly Gln Ser Leu Glu Ser Thr Val
        355                 360                 365

Gln Thr Trp Phe Lys Pro Leu Ala Tyr Ala Phe Ile Leu Thr Arg Glu
    370                 375                 380

Ser Gly Tyr Pro Gln Val Phe Tyr Gly Asp Met Tyr Gly Thr Lys Gly
385                 390                 395                 400

Asp Ser Gln Arg Glu Ile Pro Ala Leu Lys His Lys Ile Glu Pro Ile
                405                 410                 415

Leu Lys Ala Arg Lys Gln Tyr Ala Tyr Gly Ala Gln His Asp Tyr Phe
            420                 425                 430

Asp His His Asp Ile Val Gly Trp Thr Arg Glu Gly Asp Ser Ser Val
        435                 440                 445

Ala Asn Ser Gly Leu Ala Ala Leu Ile Thr Asp Gly Pro Gly Gly Ala
    450                 455                 460

Lys Arg Met Tyr Val Gly Arg Gln Asn Ala Gly Glu Thr Trp His Asp
465                 470                 475                 480

Ile Thr Gly Asn Arg Ser Glu Pro Val Val Ile Asn Ser Glu Gly Trp
```

```
                485                 490                 495
Gly Glu Phe His Val Asn Gly Ser Val Ser Ile Tyr Val Gln Arg
            500                 505                 510

Ser Gly Gly Pro Gly Thr Pro Asn Asn Gly Arg Gly Ile Gly Tyr Ile
            515                 520                 525

Glu Asn Gly Asn Thr Val Thr Tyr Ser Asn Ile Asp Phe Gly Ser Gly
            530                 535                 540

Ala Thr Gly Phe Ser Ala Thr Val Ala Thr Glu Val Asn Thr Ser Ile
545                 550                 555                 560

Gln Ile Arg Ser Asp Ser Pro Thr Gly Thr Leu Leu Gly Thr Leu Tyr
            565                 570                 575

Val Ser Ser Thr Gly Ser Trp Asn Thr Tyr Gln Pro Tyr Leu Gln Thr
            580                 585                 590

Ser Ala Lys Leu Pro Ala Phe Met Ile Leu Tyr Trp Tyr Ser Gln Val
            595                 600                 605

Gln Ser Met Trp Thr Thr Ser Tyr Leu Ala Glu Val His Gln Cys Leu
            610                 615                 620

His Leu Val Ile Thr Gln Glu Thr His Ile Leu Ser Phe Arg Pro Arg
625                 630                 635                 640

Ile Met Thr Ala Val Met Val Pro Thr Phe Lys Ser Leu Ala Tyr Gln
            645                 650                 655

Val Val Ala Ala Leu Gly Tyr Ile Glu Asn Gly Tyr Ser Thr Thr Tyr
            660                 665                 670

Lys Asn Ile Asp Phe Gly Asp Gly Ala Thr Ser Val Thr Ala Arg Val
            675                 680                 685

Ala Thr Gln Asn Ala Thr Thr Ile Gln Val Arg Leu Gly Ser Pro Ser
            690                 695                 700

Gly Thr Leu Leu Gly Thr Ile Tyr Val Gly Ser Thr Gly Ser Phe Asp
705                 710                 715                 720

Thr Tyr Arg Asp Val Ser Ala Thr Ile Ser Asn Thr Ala Gly Val Lys
                725                 730                 735

Asp Ile Val Leu Val Phe Ser Gly Pro Val Asn Val Asp Trp
                740                 745                 750

(2) INFORMATION FOR SEQ ID NO: 3:

(i) SEQUENCE CHARACTERISTICS:
        (A) LENGTH: 1203 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

ATGAAAAAGA TAACTACTAT TTTTGTCGTA TTGCTTATGA CAGTGGCGTT GTTCAGTATA    60

GGAAACACGA CTGCTGCTGA TAATGATTCA GTTGTAGAAG AACATGGGCA ATTAAGTATT   120

AGTAACGGTG AATTAGTCAA TGAACGAGGC GAACAAGTTC AGTTAAAAGG GATGAGTTCC   180

CATGGTTTGC AATGGTACGG TCAATTTGTA AACTATGAAA GTATGAAATG GCTAAGAGAT   240

GATTGGGGAA TAAATGTATT CCGAGCAGCA ATGTATACCT CTTCAGGAGG ATATATTGAT   300

GATCCATCAG TAAAGGAAAA AGTAAAAGAG GCTGTTGAAG CTGCGATAGA CCTTGATATA   360

TATGTGATCA TTGATTGGCA TATCCTTTCA GACAATGACC CAAATATATA TAAAGAAGAA   420

GCGAAGGATT TCTTTGATGA AATGTCAGAG TTGTATGGAG ACTATCCGAA TGTGATATAC   480

GAAATTGCAA ATGAACCGAA TGGTAGTGAT GTTACGTGGG GCAATCAAAT AAAACCGTAT   540
```

-continued

```
GCAGAGGAAG TCATTCCGAT TATTCGTAAC AATGACCCTA ATAACATTAT TATTGTAGGT      600

ACAGGTACAT GGAGTCAGGA TGTCCATCAT GCAGCTGATA ATCAGCTTGC AGATCCTAAC      660

GTCATGTATG CATTTCATTT TTATGCAGGG ACACATGGTC AAAATTTACG AGACCAAGTA      720

GATTATGCAT TAGATCAAGG AGCAGCGATA TTTGTTAGTG AATGGGGAAC AAGTGCAGCT      780

ACAGGTGATG GTGGCGTGTT TTTAGATGAA GCACAAGTGT GGATTGACTT TATGGATGAA      840

AGAAATTTAA GCTGGGCCAA CTGGTCTCTA ACGCATAAAG ATGAGTCATC TGCAGCGTTA      900

ATGCCAGGTG CAAATCCAAC TGGTGGTTGG ACAGAGGCTG AACTATCTCC ATCTGGTACA      960

TTTGTGAGGG AAAAAATAAG AGAATCAGCA TCTATTCCGC CAAGCGATCC AACACCGCCA     1020

TCTGATCCAG GAGAACCGGA TCCAACGCCC CCAAGTGATC AGGAGAGTA TCCAGCATGG     1080

GATCCAAATC AAATTTACAC AAATGAAATT GTGTACCATA ACGGCCAGCT ATGGCAAGCA     1140

AAATGGTGGA CACAAAATCA AGAGCCAGGT GACCCGTACG GTCCGTGGGA ACCACTCAAT     1200

TAA                                                                 1203
```

(2) INFORMATION FOR SEQ ID NO: 4:

(i) SEQUENCE CHARACTERISTICS:
        (A) LENGTH: 400 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

```
Met Lys Lys Ile Thr Thr Ile Phe Val Val Leu Leu Met Thr Val Ala
1               5                  10                  15

Leu Phe Ser Ile Gly Asn Thr Thr Ala Ala Asp Asn Asp Ser Val Val
                20                  25                  30

Glu Glu His Gly Gln Leu Ser Ile Ser Asn Gly Glu Leu Val Asn Glu
            35                  40                  45

Arg Gly Glu Gln Val Gln Leu Lys Gly Met Ser His Gly Leu Gln
    50                  55                  60

Trp Tyr Gly Gln Phe Val Asn Tyr Glu Ser Met Lys Trp Leu Arg Asp
65                  70                  75                  80

Asp Trp Gly Ile Asn Val Phe Arg Ala Ala Met Tyr Thr Ser Ser Gly
                85                  90                  95

Gly Tyr Ile Asp Asp Pro Ser Val Lys Glu Lys Val Lys Glu Ala Val
                100                 105                 110

Glu Ala Ala Ile Asp Leu Asp Ile Tyr Val Ile Ile Asp Trp His Ile
            115                 120                 125

Leu Ser Asp Asn Asp Pro Asn Ile Tyr Lys Glu Glu Ala Lys Asp Phe
        130                 135                 140

Phe Asp Glu Met Ser Glu Leu Tyr Gly Asp Tyr Pro Asn Val Ile Tyr
145                 150                 155                 160

Glu Ile Ala Asn Glu Pro Asn Gly Ser Asp Val Thr Trp Gly Asn Gln
                165                 170                 175

Ile Lys Pro Tyr Ala Glu Glu Val Ile Pro Ile Ile Arg Asn Asn Asp
            180                 185                 190

Pro Asn Asn Ile Ile Ile Val Gly Thr Gly Thr Trp Ser Gln Asp Val
        195                 200                 205

His His Ala Ala Asp Asn Gln Leu Ala Asp Pro Asn Val Met Tyr Ala
    210                 215                 220
```

```
Phe His Phe Tyr Ala Gly Thr His Gly Gln Asn Leu Arg Asp Gln Val
225                 230                 235                 240

Asp Tyr Ala Leu Asp Gln Gly Ala Ala Ile Phe Val Ser Glu Trp Gly
            245                 250                 255

Thr Ser Ala Ala Thr Gly Asp Gly Val Phe Leu Asp Glu Ala Gln
        260                 265                 270

Val Trp Ile Asp Phe Met Asp Glu Arg Asn Leu Ser Trp Ala Asn Trp
        275                 280                 285

Ser Leu Thr His Lys Asp Glu Ser Ser Ala Ala Leu Met Pro Gly Ala
290                 295                 300

Asn Pro Thr Gly Gly Trp Thr Glu Ala Glu Leu Ser Pro Ser Gly Thr
305                 310                 315                 320

Phe Val Arg Glu Lys Ile Arg Glu Ser Ala Ser Ile Pro Pro Ser Asp
            325                 330                 335

Pro Thr Pro Pro Ser Asp Pro Gly Glu Pro Asp Pro Thr Pro Pro Ser
            340                 345                 350

Asp Pro Gly Glu Tyr Pro Ala Trp Asp Pro Asn Gln Ile Tyr Thr Asn
            355                 360                 365

Glu Ile Val Tyr His Asn Gly Gln Leu Trp Gln Ala Lys Trp Trp Thr
370                 375                 380

Gln Asn Gln Glu Pro Gly Asp Pro Tyr Gly Pro Trp Glu Pro Leu Asn
385                 390                 395                 400
```

(2) INFORMATION FOR SEQ ID NO: 5:

(i) SEQUENCE CHARACTERISTICS:
        (A) LENGTH: 1683 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
ATGAAACAAC AAAAACGGCT TTACGCCCGA TTGCTGACGC TGTTATTTGC GCTCATCTTC      60
TTGCTGCCTC ATTCTGCAGC AGCGGCGGCA AATCTTAATG GGACGCTGAT GCAGTATTTT     120
GAATGGTACA TGCCCAATGA CGGCCAACAT TGGAAGCGTT TGCAAAACGA CTCGGCATAT     180
TTGGCTGAAC ACGGTATTAC TGCCGTCTGG ATTCCCCCGG CATATAAGGG AACGAGCCAA     240
GCGGATGTGG GCTACGGTGC TTACGACCTT TATGATTTAG GGAGTTTCA TCAAAAAGGG      300
ACGGTTCGGA CAAAGTACGG CACAAAAGGA GAGCTGCAAT CTGCGATCAA AGTCTTCAT      360
TCCCGCGACA TTAACGTTTA CGGGGATGTG GTCATCAACC ACAAAGGCGG CGCTGATGCG     420
ACCGAAGATG TAACCGCGGT TGAAGTCGAT CCCGCTGACC GCAACCGCGT AATCTCAGGA     480
GAACACCTAA TTAAAGCCTG GACACATTTT CATTTTCCGG GGGCCGGCAG CACATACAGC     540
GATTTTAAAT GGCATTGGTA CCATTTTGAC GGAACCGATT GGGACGAGTC CCGAAAGCTG     600
AACCGCATCT ATAAGTTTCA AGGAAAGGCT TGGGATTGGG AAGTTTCCAA TGAAAACGGC     660
AACTATGATT ATTTGATGTA TGCCGACATC GATTATGACC ATCCTGATGT CGCAGCAGAA     720
ATTAAGAGAT GGGGCACTTG GTATGCCAAT GAACTGCAAT GGACGGAAA CCGTCTTGAT      780
GCTGTCAAAC ACATTAAATT TTCTTTTTTG CGGGATTGGG TTAATCATGT CAGGGAAAAA     840
ACGGGGAAGG AAATGTTTAC GGTAGCTGAA TATTGGCAGA ATGACTTGGG CGCGCTGGAA     900
AACTATTTGA ACAAAACAAA TTTTAATCAT TCAGTGTTTG ACGTGCCGCT TCATTATCAG     960
TTCCATGCTG CATCGACACA GGGAGGCGGC TATGATATGA GGAAATTGCT GAACGGTACG    1020
```

```
GTCGTTTCCA AGCATCCGTT GAAATCGGTT ACATTTGTCG ATAACCATGA TACACAGCCG    1080

GGGCAATCGC TTGAGTCGAC TGTCCAAACA TGGTTTAAGC CGCTTGCTTA CGCTTTTATT    1140

CTCACAAGGG AATCTGGATA CCCTCAGGTT TTCTACGGGG ATATGTACGG GACGAAAGGA    1200

GACTCCCAGC GCGAAATTCC TGCCTTGAAA CACAAAATTG AACCGATCTT AAAAGCGAGA    1260

AAACAGTATG CGTACGGAGC ACAGCATGAT TATTTCGACC ACCATGACAT TGTCGGCTGG    1320

ACAAGGGAAG GCGACAGCTC GGTTGCAAAT TCAGGTTTGG CGGCATTAAT AACAGACGGA    1380

CCCGGTGGGG CAAAGCGAAT GTATGTCGGC CGGCAAAACG CCGGTGAGAC ATGGCATGAC    1440

ATTACCGGAA ACCGTTCGGA GCCGGTTGTC ATCAATTCGG AAGGCTGGGG AGAGTTTCAC    1500

GTAAACGGCG GATCCGTTTC AATTTATGTT CAAAGATCTC CTGGAGAGTA TCCAGCATGG    1560

GATCCAAATC AAATTTACAC AAATGAAATT GTGTACCATA ACGGCCAGCT ATGGCAAGCA    1620

AAATGGTGGA CACAAAATCA AGAGCCAGGT GACCCGTACG GTCCGTGGGA ACCACTCAAT    1680

TAA                                                                  1683
```

(2) INFORMATION FOR SEQ ID NO: 6:

(i) SEQUENCE CHARACTERISTICS:
        (A) LENGTH: 560 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

```
Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ala Ala Ala Asn Leu
            20                  25                  30

Asn Gly Thr Leu Met Gln Tyr Phe Glu Trp Tyr Met Pro Asn Asp Gly
        35                  40                  45

Gln His Trp Lys Arg Leu Gln Asn Asp Ser Ala Tyr Leu Ala Glu His
    50                  55                  60

Gly Ile Thr Ala Val Trp Ile Pro Pro Ala Tyr Lys Gly Thr Ser Gln
65                  70                  75                  80

Ala Asp Val Gly Tyr Gly Ala Tyr Asp Leu Tyr Asp Leu Gly Glu Phe
                85                  90                  95

His Gln Lys Gly Thr Val Arg Thr Lys Tyr Gly Thr Lys Gly Glu Leu
            100                 105                 110

Gln Ser Ala Ile Lys Ser Leu His Ser Arg Asp Ile Asn Val Tyr Gly
        115                 120                 125

Asp Val Val Ile Asn His Lys Gly Gly Ala Asp Ala Thr Glu Asp Val
    130                 135                 140

Thr Ala Val Glu Val Asp Pro Ala Asp Arg Asn Arg Val Ile Ser Gly
145                 150                 155                 160

Glu His Leu Ile Lys Ala Trp Thr His Phe His Phe Pro Gly Ala Gly
                165                 170                 175

Ser Thr Tyr Ser Asp Phe Lys Trp His Trp Tyr His Phe Asp Gly Thr
            180                 185                 190

Asp Trp Asp Glu Ser Arg Lys Leu Asn Arg Ile Tyr Lys Phe Gln Gly
        195                 200                 205

Lys Ala Trp Asp Trp Glu Val Ser Asn Glu Asn Gly Asn Tyr Asp Tyr
    210                 215                 220

Leu Met Tyr Ala Asp Ile Asp Tyr Asp His Pro Asp Val Ala Ala Glu
```

```
                225                 230                 235                 240
Ile Lys Arg Trp Gly Thr Trp Tyr Ala Asn Glu Leu Gln Leu Asp Gly
                245                 250                 255

Asn Arg Leu Asp Ala Val Lys His Ile Lys Phe Ser Phe Leu Arg Asp
            260                 265                 270

Trp Val Asn His Val Arg Glu Lys Thr Gly Lys Glu Met Phe Thr Val
        275                 280                 285

Ala Glu Tyr Trp Gln Asn Asp Leu Gly Ala Leu Glu Asn Tyr Leu Asn
    290                 295                 300

Lys Thr Asn Phe Asn His Ser Val Phe Asp Val Pro Leu His Tyr Gln
305                 310                 315                 320

Phe His Ala Ala Ser Thr Gln Gly Gly Gly Tyr Asp Met Arg Lys Leu
                325                 330                 335

Leu Asn Gly Thr Val Val Ser Lys His Pro Leu Lys Ser Val Thr Phe
            340                 345                 350

Val Asp Asn His Asp Thr Gln Pro Gly Gln Ser Leu Glu Ser Thr Val
        355                 360                 365

Gln Thr Trp Phe Lys Pro Leu Ala Tyr Ala Phe Ile Leu Thr Arg Glu
    370                 375                 380

Ser Gly Tyr Pro Gln Val Phe Tyr Gly Asp Met Tyr Gly Thr Lys Gly
385                 390                 395                 400

Asp Ser Gln Arg Glu Ile Pro Ala Leu Lys His Lys Ile Glu Pro Ile
                405                 410                 415

Leu Lys Ala Arg Lys Gln Tyr Ala Tyr Gly Ala Gln His Asp Tyr Phe
            420                 425                 430

Asp His His Asp Ile Val Gly Trp Thr Arg Glu Gly Asp Ser Ser Val
        435                 440                 445

Ala Asn Ser Gly Leu Ala Ala Leu Ile Thr Asp Gly Pro Gly Gly Ala
    450                 455                 460

Lys Arg Met Tyr Val Gly Arg Gln Asn Ala Gly Glu Thr Trp His Asp
465                 470                 475                 480

Ile Thr Gly Asn Arg Ser Glu Pro Val Val Ile Asn Ser Glu Gly Trp
                485                 490                 495

Gly Glu Phe His Val Asn Gly Gly Ser Val Ser Ile Tyr Val Gln Arg
            500                 505                 510

Ser Pro Gly Glu Tyr Pro Ala Trp Asp Pro Asn Gln Ile Tyr Thr Asn
        515                 520                 525

Glu Ile Val Tyr His Asn Gly Gln Leu Trp Gln Ala Lys Trp Trp Thr
    530                 535                 540

Gln Asn Gln Glu Pro Gly Asp Pro Tyr Gly Pro Trp Glu Pro Leu Asn
545                 550                 555                 560

(2) INFORMATION FOR SEQ ID NO:7:

(i) SEQUENCE CHARACTERISTICS:
        (A) LENGTH: 1893 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

ATGAAACAAC AAAAACGGCT TTACGCCCGA TTGCTGACGC TGTTATTTGC GCTCATCTTC      60

TTGCTGCCTC ATTCTGCAGC AGCGGCGGCA AATCTTAATG CTCCCGGCTG CCGCGTCGAC     120

TACGCCGTCA CCAACCAGTG GCCCGGCGGC TTCGGCGCCA ACGTCACGAT CACCAACCTC     180
```

```
GGCGACCCCG TCTCGTCGTG GAAGCTCGAC TGGACCTACA CCGCAGGCCA GCGGATCCAG    240

CAGCTGTGGA ACGGCACCGC GTCGACCAAC GGCGGCCAGG TCTCCGTCAC CAGCCTGCCC    300

TGGAACGGCA GCATCCCGAC CGGCGGCACG GCGTCGTTCG GGTTCAACGG CTCGTGGGCC    360

GGGTCCAACC CGACGCCGGC GTCGTTCTCG CTCAACGGCA CCACGTGCAC TGGTACAGTT    420

CCTACAACTA GTCCTACACG TGCAAATCTT AATGGGACGC TGATGCAGTA TTTTGAATGG    480

TACATGCCCA ATGACGGCCA ACATTGGAGG CGTTTGCAAA ACGACTCGGC ATATTTGGCT    540

GAACACGGTA TTACTGCCGT CTGGATTCCC CCGGCATATA AGGGAACGAG CCAAGCGGAT    600

GTGGGCTACG GTGCTTACGA CCTTTATGAT TTAGGGGAGT TTCATCAAAA AGGGACGGTT    660

CGGACAAAGT ACGGCACAAA AGGAGAGCTG CAATCTGCGA TCAAAAGTCT TCATTCCCGC    720

GACATTAACG TTTACGGGGA TGTGGTCATC AACCACAAAG GCGGCGCTGA TGCGACCGAA    780

GATGTAACCG CGGTTGAAGT CGATCCCGCT GACCGCAACC GCGTAATTTC AGGAGAACAC    840

CTAATTAAAG CCTGGACACA TTTTCATTTT CCGGGGCGCG GCAGCACATA CAGCGATTTT    900

AAATGGCATT GGTACCATTT TGACGGAACC GATTGGGACG AGTCCCGAAA GCTGAACCGC    960

ATCTATAAGT TCAAGGAAA GGCTTGGGAT TGGGAAGTTT CCAATGAAAA CGGCAACTAT   1020

GATTATTTGA TGTATGCCGA CATCGATTAT GACCATCCTG ATGTCGCAGC AGAAATTAAG   1080

AGATGGGGCA CTTGGTATGC CAATGAACTG CAATTGGACG GTTTCCGTCT TGATGCTGTC   1140

AAACACATTA AATTTTCTTT TTTGCGGGAT TGGGTTAATC ATGTCAGGGA AAAAACGGGG   1200

AAGGAAATGT TTACGGTAGC TGAATATTGG CAGAATGACT TGGGCGCGCT GGAAAACTAT   1260

TTGAACAAAA CAAATTTTAA TCATTCAGTG TTTGACGTGC CGCTTCATTA TCAGTTCCAT   1320

GCTGCATCGA CACAGGGAGG CGGCTATGAT ATGAGGAAAT TGCTGAACGG TACGGTCGTT   1380

TCCAAGCATC CGTTGAAATC GGTTACATTT GTCGATAACC ATGATACACA GCCGGGGCAA   1440

TCGCTTGAGT CGACTGTCCA ACATGGTTTT AAGCCGCTTG CTTACGCTTT TATTCTCACA   1500

AGGGAATCTG GATACCCTCA GGTTTTCTAC GGGGATATGT ACGGGACGAA AGGAGACTCC   1560

CAGCGCGAAA TTCCTGCCTT GAAACACAAA ATTGAACCGA TCTTAAAAGC GAGAAAACAG   1620

TATGCGTACG GAGCACAGCA TGATTATTTC GACCACCATG ACATTGTCGG CTGGACAAGG   1680

GAAGGCGACA GCTCGGTTGC AAATTCAGGT TTGGCGGCAT TAATAACAGA CGGACCCGGT   1740

GGGGCAAAGC GAATGTATGT CGGCCGGCAA AACGCCGGTG AGACATGGCA TGACATTACC   1800

GGAAACCGTT CGGAGCCGGT TGTCATCAAT TCGGAAGGCT GGGGAGAGTT TCACGTAAAC   1860

GGCGGGTCGG TTTCAATTTA TGTTCAAAGA TAG                                1893

(2) INFORMATION FOR SEQ ID NO:8:

(i) SEQUENCE CHARACTERISTICS:
        (A) LENGTH: 631 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:8:

Met Lys Gln Gln Lys Arg Leu Tyr Ala Arg Leu Leu Thr Leu Leu Phe
1               5                  10                  15

Ala Leu Ile Phe Leu Leu Pro His Ser Ala Ala Ala Ala Asn Leu
            20                  25                  30

Asn Ala Pro Gly Cys Arg Val Asp Tyr Ala Val Thr Asn Gln Trp Pro
        35                  40                  45
```

```
Gly Gly Phe Gly Ala Asn Val Thr Ile Thr Asn Leu Gly Asp Pro Val
     50                  55                  60

Ser Ser Trp Lys Leu Asp Trp Thr Tyr Thr Ala Gly Gln Arg Ile Gln
 65              70                  75                      80

Gln Leu Trp Asn Gly Thr Ala Ser Thr Asn Gly Gly Gln Val Ser Val
                 85                  90                  95

Thr Ser Leu Pro Trp Asn Gly Ser Ile Pro Thr Gly Gly Thr Ala Ser
                100                 105             110

Phe Gly Phe Asn Gly Ser Trp Ala Gly Ser Asn Pro Thr Pro Ala Ser
            115                 120             125

Phe Ser Leu Asn Gly Thr Thr Cys Thr Gly Thr Val Pro Thr Thr Ser
            130                 135             140

Pro Thr Arg Ala Asn Leu Asn Gly Thr Leu Met Gln Tyr Phe Glu Trp
145             150                 155                     160

Tyr Met Pro Asn Asp Gly Gln His Trp Arg Arg Leu Gln Asn Asp Ser
                165                 170                 175

Ala Tyr Leu Ala Glu His Gly Ile Thr Ala Val Trp Ile Pro Pro Ala
            180                 185                 190

Tyr Lys Gly Thr Ser Gln Ala Asp Val Gly Tyr Gly Ala Tyr Asp Leu
            195                 200             205

Tyr Asp Leu Gly Glu Phe His Gln Lys Gly Thr Val Arg Thr Lys Tyr
210                 215                 220

Gly Thr Lys Gly Glu Leu Gln Ser Ala Ile Lys Ser Leu His Ser Arg
225                 230                 235                 240

Asp Ile Asn Val Tyr Gly Asp Val Val Ile Asn His Lys Gly Gly Ala
                245                 250                 255

Asp Ala Thr Glu Asp Val Thr Ala Val Glu Val Asp Pro Ala Asp Arg
                260                 265                 270

Asn Arg Val Ile Ser Gly Glu His Leu Ile Lys Ala Trp Thr His Phe
                275                 280                 285

His Phe Pro Gly Arg Gly Ser Thr Tyr Ser Asp Phe Lys Trp His Trp
            290                 295                 300

Tyr His Phe Asp Gly Thr Asp Trp Asp Glu Ser Arg Lys Leu Asn Arg
305                 310                 315                 320

Ile Tyr Lys Phe Gln Gly Lys Ala Trp Asp Trp Glu Val Ser Asn Glu
                325                 330                 335

Asn Gly Asn Tyr Asp Tyr Leu Met Tyr Ala Asp Ile Asp Tyr Asp His
                340                 345                 350

Pro Asp Val Ala Ala Glu Ile Lys Arg Trp Gly Thr Trp Tyr Ala Asn
            355                 360                 365

Glu Leu Gln Leu Asp Gly Phe Arg Leu Asp Ala Val Lys His Ile Lys
            370                 375                 380

Phe Ser Phe Leu Arg Asp Trp Val Asn His Val Arg Glu Lys Thr Gly
385                 390                 395                 400

Lys Glu Met Phe Thr Val Ala Glu Tyr Trp Gln Asn Asp Leu Gly Ala
                405                 410                 415

Leu Glu Asn Tyr Leu Asn Lys Thr Asn Phe Asn His Ser Val Phe Asp
            420                 425                 430

Val Pro Leu His Tyr Gln Phe His Ala Ala Ser Thr Gln Gly Gly Gly
            435                 440                 445

Tyr Asp Met Arg Lys Leu Leu Asn Gly Thr Val Val Ser Lys His Pro
450                 455                 460

Leu Lys Ser Val Thr Phe Val Asp Asn His Asp Thr Gln Pro Gly Gln
```

```
465                470                475                480
Ser Leu Glu Ser Thr Val Gln Thr Trp Phe Lys Pro Leu Ala Tyr Ala
                485                490                495

Phe Ile Leu Thr Arg Glu Ser Gly Tyr Pro Gln Val Phe Tyr Gly Asp
            500                505                510

Met Tyr Gly Thr Lys Gly Asp Ser Gln Arg Glu Ile Pro Ala Leu Lys
            515                520                525

His Lys Ile Glu Pro Ile Leu Lys Ala Arg Lys Gln Tyr Ala Tyr Gly
        530                535                540

Ala Gln His Asp Tyr Phe Asp His His Asp Ile Val Gly Trp Thr Arg
545                550                555                560

Glu Gly Asp Ser Ser Val Ala Asn Ser Gly Leu Ala Ala Leu Ile Thr
                565                570                575

Asp Gly Pro Gly Gly Ala Lys Arg Met Tyr Val Gly Arg Gln Asn Ala
            580                585                590

Gly Glu Thr Trp His Asp Ile Thr Gly Asn Arg Ser Glu Pro Val Val
            595                600                605

Ile Asn Ser Glu Gly Trp Gly Glu Phe His Val Asn Gly Gly Ser Val
        610                615                620

Ser Ile Tyr Val Gln Arg Glx
625                630
```

(2) INFORMATION FOR SEQ ID NO:9:

(i) SEQUENCE CHARACTERISTICS:
        (A) LENGTH: 5679 base pairs
        (B) TYPE: nucleic acid
        (C) STRANDEDNESS: single
        (D) TOPOLOGY: linear (xi) SEQUENCE DESCRIPTION: SEQ ID NO:9:

```
GCGCCCAATA CGCAAACCGC CTCTCCCCGC GCGTTGGCCG ATTCATTAAT GCAGCTGGCA    60
CGACAGGTTT CCCGACTGGA AAGCGGGCAG TGAGCGCAAC GCAATTAATG TGAGTTAGCT   120
CACTCATTAG GCACCCCAGG CTTTACACTT TATGCTTCCG GCTCGTATGT TGTGTGGAAT   180
TGTGAGCGGA TAACAATTTC ACACAGGAAA CAGCTATGAC CATGATTACG CCAAGCTTGC   240
ATGCCTGCAG GTCGACGCAT TCCGAATACG AGGCCTGATT AATGATTACA TACGCCTCCG   300
GGTAGTAGAC CGAGCAGCCG AGCCAGTTCA GCGCCTAAAA CGCCTTATAC AATTAAGCAG   360
TTAAAGAAGT TAGAATCTAC GCTTAAAAAG CTACTTAAAA ATCGATCTCG CAGTCCGAT   420
TCGCCTATCA AACCAGTTT AAATCAACTG ATTAAGGTG CCGAACGAGC TATAAATGAT    480
ATAACAATAT TAAAGCATTA ATTAGAGCAA TATCAGGCCG CGCACGAAAG GCAACTTAAA   540
AAGCGAAAGC GCTCTACTAA ACAGATTACT TTTGAAAAAG GCACATCAGT ATTTAAAGCC   600
CGAATCCTTA TTAAGCGCCG AAATCAGGCA GATAAAGCCA TACAGGCAGA TAGACCTCTA   660
CCTATTAAAT CGGCTTCTAG GCGCGCTCCA TCTAAATGTT CTGGCTGTGG TGTACAGGGG   720
CATAAAATTA CGCACTACCC GAATCGATAG AACTACTCAT TTTTATATAG AAGTCAGAAT   780
TCATAGTGTT TTGATCATTT TAAATTTTTA TATGGCGGGT GGTGGGCAAC TCGCTTGCGC   840
GGGCAACTCG CTTACCGATT ACGTTAGGGC TGATATTTAC GTGAAAATCG TCAAGGGATG   900
CAAGACCAAA GTAGTAAAAC CCCGGAAGTC AACAGCATCC AAGCCCAAGT CCTTCACGGA   960
GAAACCCCAG CGTCCACATC ACGAGCGAAG GACCACCTCT AGGCATCGGA CGCACCATCC  1020
AATTAGAAGC AGCAAAGCGA AACAGCCCAA GAAAAAGGTC GGCCCGTCGG CCTTTTCTGC  1080
AACGCTGATC ACGGGCAGCG ATCCAACCAA CACCCTCCAG AGTGACTAGG GGCGGAAATT  1140
```

```
TAAAGGGATT AATTTCCACT CAACCACAAA TCACAGTCGT CCCCGGTATT GTCCTGCAGA    1200

ATGCAATTTA AACTCTTCTG CGAATCGCTT GGATTCCCCG CCCCTAGTCG TAGAGCTTAA    1260

AGTATGTCCC TTGTCGATGC GATGATACAC AACATATAAA TACTAGCAAG GGATGCCATG    1320

CTTGGAGGAT AGCAACCGAC AACATCACAT CAAGCTCTCC CTTCTCTGAA CAATAAACCC    1380

CACAGGGGGG ATCCACTAGT AACGGCCGCC AGTGTGCTGG AAAGCGACTT GAAACGCCCC    1440

AAATGAAGTC CTCCATCCTC GCCAGCGTCT TCGCCACGGG CGCCGTGGCT CAAAGTGGTC    1500

CGTGGCAGCA ATGTGGTGGC ATCGGATGGC AAGGATCGAC CGACTGTGTG TCGGGCTACC    1560

ACTGCGTCTA CCAGAACGAT TGGTACAGCC AGTGCGTGCC TGGCGCGGCG TCGACAACGC    1620

TGCAGACATC GACCACGTCC AGGCCCACCG CCACCAGCAC CGCCCCTCCG TCGTCCACCA    1680

CCTCGCCTAG CGTGGCCAGT CCTATTCGTC GAGAGGTCTC GCAGGATCTG TTTAACCAGT    1740

TCAATCTCTT TGCACAGTAT TCTGCAGCCG CATACTGCGG AAAAAACAAT GATGCCCCAG    1800

CTGGTACAAA CATTACGTGC ACGGGAAATG CCTGCCCCGA GGTAGAGAAG GCGGATGCAA    1860

CGTTTCTCTA CTCGTTTGAA GACTCTGGAG TGGGCGATGT CACCGGCTTC CTTGCTCTCG    1920

ACAACACGAA CAAATTGATC GTCCTCTCTT TCCGTGGCTC TCGTTCCATA GAGAACTGGA    1980

TCGGGAATCT TAAGTTCCTC TTGAAAAAAA TAAATGACAT TTGCTCCGGC TGCAGGGGAC    2040

ATGACGGCTT CACTTCGTCC TGGAGGTCTG TAGCCGATAC GTTAAGGCAG AAGGTGGAGG    2100

ATGCTGTGAG GGAGCATCCC GACTATCGCG TGGTGTTTAC CGGACATAGC TTGGGTGGTG    2160

CATTGGCAAC TGTTGCCGGA GCAGACCTGC GTGGAAATGG GTATGATATC GACGTGTTTT    2220

CATATGGCGC CCCCCGAGTC GGAAACAGGG CTTTTGCAGA ATTCCTGACC GTACAGACCG    2280

GCGGAACACT CTACCGCATT ACCCACACCA ATGATATTGT CCCTAGACTC CCGCCGCGCG    2340

AATTCGGTTA CAGCCATTCT AGCCCAGAAT ACTGGATCAA ATCTGGAACC CTTGTCCCCG    2400

TCACCCGAAA CGATATCGTG AAGATAGAAG GCATCGATGC CACCGGCGGC AATAACCGGC    2460

CGAACATTCC GGATATCCCT GCGCACCTAT GGTACTTCGG GTTAATTGGG ACATGTCTTT    2520

AGTGGCCGGC GCGGCTGGGT CGACTCTAGC GAGCTCGAGA TCTAGAGGGT GACTGACACC    2580

TGGCGGTAGA CAATCAATCC ATTTCGCTAT AGTTAAAGGA TGGGGATGAG GGCAATTGGT    2640

TATATGATCA TGTATGTAGT GGGTGTGCAT AATAGTAGTG AAATGGAAGC CAAGTCATGT    2700

GATTGTAATC GACCGACGGA ATTGAGGATA TCCGGAAATA CAGACACCGT GAAAGCCATG    2760

GTCTTTCCTT CGTGTAGAAG ACCAGACAGA CAGTCCCTGA TTTACCCTTG CACAAAGCAC    2820

TAGAAAATTA GCATTCCATC CTTCTCTGCT TGCTCTGCTG ATATCACTGT CATTCAATGC    2880

ATAGCCATGA GCTCATCTTA GATCCAAGCA CGTAATTCCA TAGCCGAGGT CCACAGTGGA    2940

GCAGCAACAT TCCCCATCAT TGCTTTCCCC AGGGGCCTCC CAACGACTAA ATCAAGAGTA    3000

TATCTCTACC GTCCAATAGA TCGTCTTCGC TTCAAAATCT TTGACAATTC CAAGAGGGTC    3060

CCCATCCATC AAACCCAGTT CAATAATAGC CGAGATGCAT GGTGGAGTCA ATTAGGCAGT    3120

ATTGCTGGAA TGTCGGGCCA GTTGGCCGG GTGGTCATTG GCCGCCTGTG ATGCCATCTG    3180

CCACTAAATC CGATCATTGA TCCACCGCCC ACGAGGCGCG TCTTTGCTTT TTGCGCGGCG    3240

TCCAGGTTCA ACTCTCTCGC TCTAGATATC GATGAATTCA CTGGCCGTCG TTTTACAACG    3300

TCGTGACTGG GAAAACCCTG GCGTTACCCA ACTTAATCGC CTTGCAGCAC ATCCCCCTTT    3360

CGCCAGCTGG CGTAATAGCG AAGAGGCCCG CACCGATCGC CCTTCCCAAC AGTTGCGCAG    3420

CCTGAATGGC GAATGGCGCC TGATGCGGTA TTTTCTCCTT ACGCATCTGT GCGGTATTTC    3480

ACACCGCATA TGGTGCACTC TCAGTACAAT CTGCTCTGAT GCCGCATAGT TAAGCCAGCC    3540
```

```
CCGACACCCG CCAACACCCG CTGACGCGCC CTGACGGGCT TGTCTGCTCC CGGCATCCGC    3600

TTACAGACAA GCTGTGACCG TCTCCGGGAG CTGCATGTGT CAGAGGTTTT CACCGTCATC    3660

ACCGAAACGC GCGAGACGAA AGGGCCTCGT GATACGCCTA TTTTTATAGG TTAATGTCAT    3720

GATAATAATG GTTTCTTAGA CGTCAGGTGG CACTTTTCGG GGAAATGTGC GCGGAACCCC    3780

TATTTGTTTA TTTTTCTAAA TACATTCAAA TATGTATCCG CTCATGAGAC AATAACCCTG    3840

ATAAATGCTT CAATAATATT GAAAAAGGAA GAGTATGAGT ATTCAACATT TCCGTGTCGC    3900

CCTTATTCCC TTTTTTGCGG CATTTTGCCT TCCTGTTTTT GCTCACCCAG AAACGCTGGT    3960

GAAAGTAAAA GATGCTGAAG ATCAGTTGGG TGCACGAGTG GGTTACATCG AACTGGATCT    4020

CAACAGCGGT AAGATCCTTG AGAGTTTTCG CCCCGAAGAA CGTTTTCCAA TGATGAGCAC    4080

TTTTAAAGTT CTGCTATGTG GCGCGGTATT ATCCCGTATT GACGCCGGGC AAGAGCAACT    4140

CGGTCGCCGC ATACACTATT CTCAGAATGA CTTGGTTGAC GCGTCACCAG TCACAGAAAA    4200

GCATCTTACG GATGGCATGA CAGTAAGAGA ATTATGCAGT GCTGCCATAA CCATGAGTGA    4260

TAACACTGCG GCCAACTTAC TTCTGACAAC GATCGGAGGA CCGAAGGAGC TAACCGCTTT    4320

TTTGCACAAC ATGGGGGATC ATGTAACTCG CCTTGATCGT TGGGAACCGG AGCTGAATGA    4380

AGCCATACCA AACGACGAGC GTGACACCAC GATGCCTGTA GCAATGGCAA CAACGTTGCG    4440

CAAACTATTA ACTGGCGAAC TACTTACTCT AGCTTCCCGG CAACAATTAA TAGACTGGAT    4500

GGAGGCGGAT AAAGTTGCAG GACCACTTCT GCGCTCGGCC CTTCCGGCTG GCTGGTTTAT    4560

TGCTGATAAA TCTGGAGCCG GTGAGCGTGG GTCTCGCGGT ATCATTGCAG CACTGGGGCC    4620

AGATGGTAAG CCCTCCCGTA TCGTAGTTAT CTACACGACG GGGAGTCAGG CAACTATGGA    4680

TGAACGAAAT AGACAGATCG CTGAGATAGG TGCCTCACTG ATTAAGCATT GGTAACTGTC    4740

AGACCAAGTT TACTCATATA TACTTTAGAT TGATTTAAAA CTTCATTTTT AATTTAAAAG    4800

GATCTAGGTG AAGATCCTTT TTGATAATCT CATGACCAAA ATCCCTTAAC GTGAGTTTTC    4860

GTTCCACTGA GCGTCAGACC CCGTAGAAAA GATCAAAGGA TCTTCTTGAG ATCCTTTTTT    4920

TCTGCGCGTA ATCTGCTGCT TGCAAACAAA AAAACCACCG CTACCAGCGG TGGTTTGTTT    4980

GCCGGATCAA GAGCTACCAA CTCTTTTTCC GAAGGTAACT GGCTTCAGCA GAGCGCAGAT    5040

ACCAAATACT GTCCTTCTAG TGTAGCCGTA GTTAGGCCAC CACTTCAAGA ACTCTGTAGC    5100

ACCGCCTACA TACCTCGCTC TGCTAATCCT GTTACCAGTG GCTGCTGCCA GTGGCGATAA    5160

GTCGTGTCTT ACCGGGTTGG ACTCAAGACG ATAGTTACCG GATAAGGCGC AGCGGTCGGG    5220

CTGAACGGGG GGTTCGTGCA CACAGCCCAG CTTGGAGCGA ACGACCTACA CCGAACTGAG    5280

ATACCTACAG CGTGAGCTAT GAGAAAGCGC CACGCTTCCC GAAGGGAGAA AGGCGGACAG    5340

GTATCCGGTA AGCGGCAGGG TCGGAACAGG AGAGCGCACG AGGGAGCTTC CAGGGGGAAA    5400

CGCCTGGTAT CTTTATAGTC CTGTCGGGTT TCGCCACCTC TGACTTGAGC GTCGATTTTT    5460

GTGATGCTCG TCAGGGGGGC GGAGCCTATG GAAAAACGCC AGCAACGCGG CCTTTTTACG    5520

GTTCCTGGCC TTTTGCTGGC CTTTTGCTCA CATGTTCTTT CCTGCGTTAT CCCCTGATTC    5580

TGTGGATAAC CGTATTACCG CCTTTGAGTG AGCTGATACC GCTCGCCGCA GCCGAACGAC    5640

CGAGCGCAGC GAGTCAGTGA GCGAGGAAGC GGAAGAGAG                           5679
```

(2) INFORMATION FOR SEQ ID NO:10:

(i) SEQUENCE CHARACTERISTICS:
        (A) LENGTH: 5580 base pairs
        (B) TYPE: nucleic acid
        (C) STRANDEDNESS: single (D) TOPOLOGY: linear (xi) SEQUENCE DESCRIPTION: SEQ ID NO:10:

```
GCGCCCAATA CGCAAACCGC CTCTCCCCGC GCGTTGGCCG ATTCATTAAT GCAGCTGGCA      60

CGACAGGTTT CCCGACTGGA AAGCGGGCAG TGAGCGCAAC GCAATTAATG TGAGTTAGCT     120

CACTCATTAG GCACCCCAGG CTTTACACTT TATGCTTCCG GCTCGTATGT TGTGTGGAAT     180

TGTGAGCGGA TAACAATTTC ACACAGGAAA CAGCTATGAC CATGATTACG CCAAGCTTGC     240

ATGCCTGCAG GTCGACGCAT TCCGAATACG AGGCCTGATT AATGATTACA TACGCCTCCG     300

GGTAGTAGAC CGAGCAGCCG AGCCAGTTCA GCGCCTAAAA CGCCTTATAC AATTAAGCAG     360

TTAAAGAAGT TAGAATCTAC GCTTAAAAAG CTACTTAAAA ATCGATCTCG CAGTCCCGAT     420

TCGCCTATCA AAACCAGTTT AAATCAACTG ATTAAAGGTG CCGAACGAGC TATAAATGAT     480

ATAACAATAT TAAAGCATTA ATTAGAGCAA TATCAGGCCG CGCACGAAAG GCAACTTAAA     540

AAGCGAAAGC GCTCTACTAA ACAGATTACT TTTGAAAAAG GCACATCAGT ATTTAAAGCC     600

CGAATCCTTA TTAAGCGCCG AAATCAGGCA GATAAAGCCA TACAGGCAGA TAGACCTCTA     660

CCTATTAAAT CGGCTTCTAG GCGCGCTCCA TCTAAATGTT CTGGCTGTGG TGTACAGGGG     720

CATAAAATTA CGCACTACCC GAATCGATAG AACTACTCAT TTTTATATAG AAGTCAGAAT     780

TCATAGTGTT TTGATCATTT TAAATTTTTA TATGGCGGGT GGTGGGCAAC TCGCTTGCGC     840

GGGCAACTCG CTTACCGATT ACGTTAGGGC TGATATTTAC GTGAAAATCG TCAAGGGATG     900

CAAGACCAAA GTAGTAAAAC CCCGGAAGTC AACAGCATCC AAGCCCAAGT CCTTCACGGA     960

GAAACCCCAG CGTCCACATC ACGAGCGAAG GACCACCTCT AGGCATCGGA CGCACCATCC    1020

AATTAGAAGC AGCAAAGCGA AACAGCCCAA GAAAAAGGTC GGCCCGTCGG CCTTTTCTGC    1080

AACGCTGATC ACGGGCAGCG ATCCAACCAA CACCCTCCAG AGTGACTAGG GGCGGAAATT    1140

TAAAGGGATT AATTTCCACT CAACCACAAA TCACAGTCGT CCCCGGTATT GTCCTGCAGA    1200

ATGCAATTTA AACTCTTCTG CGAATCGCTT GGATTCCCCG CCCCTAGTCG TAGAGCTTAA    1260

AGTATGTCCC TTGTCGATGC GATGATACAC AACATATAAA TACTAGCAAG GGATGCCATG    1320

CTTGGAGGAT AGCAACCGAC AACATCACAT CAAGCTCTCC CTTCTCTGAA CAATAAACCC    1380

CACAGGGGGG ATCCACTAGT AACGGCCGCC AGTGTGCTGG AAAGCGACTT GAAACGCCCC    1440

AAATGAAGTC CTCCATCCTC GCCAGCGTCT TCGCCACGGG CGCCGTGGCT CAAAGTGGTC    1500

CGTGGCAGCA ATGTGGTGGC ATCGGATGGC AAGGATCGAC CGACTGTGTG TCGGGCTACC    1560

ACTGCGTCTA CCAGAACGAT TGGTACAGCC AGTGCGCTAG CCCTCCTCGT CGACCTGTCT    1620

CGCAGGATCT GTTTAACCAG TTCAATCTCT TTGCACAGTA TTCTGCAGCC GCATACTGCG    1680

GAAAAAACAA TGATGCCCCA GCTGGTACAA ACATTACGTG CACGGGAAAT GCCTGCCCCG    1740

AGGTAGAGAA GGCGGATGCA ACGTTTCTCT ACTCGTTTGA AGACTCTGGA GTGGGCGATG    1800

TCACCGGCTT CCTTGCTCTC GACAACACGA ACAAATTGAT CGTCCTCTCT TTCCGTGGCT    1860

CTCGTTCCAT AGAGAACTGG ATCGGGAATC TTAAGTTCCT CTTGAAAAAA ATAAATGACA    1920

TTTGCTCCGG CTGCAGGGGA CATGACGGCT TCACTTCGTC CTGGAGGTCT GTAGCCGATA    1980

CGTTAAGGCA GAAGGTGGAG GATGCTGTGA GGGAGCATCC CGACTATCGC GTGGTGTTTA    2040

CCGGACATAG CTTGGGTGGT GCATTGGCAA CTGTTGCCGG AGCAGACCTG CGTGGAAATG    2100

GGTATGATAT CGACGTGTTT TCATATGGCG CCCCCCGAGT CGGAAACAGG GCTTTTGCAG    2160

AATTCCTGAC CGTACAGACC GGCGGAACAC TCTACCGCAT TACCCACACC AATGATATTG    2220

TCCCTAGACT CCCGCCGCGC GAATTCGGTT ACAGCCATTC TAGCCCAGAA TACTGGATCA    2280
```

```
AATCTGGAAC CCTTGTCCCC GTCACCCGAA ACGATATCGT GAAGATAGAA GGCATCGATG    2340

CCACCGGCGG CAATAACCGG CCGAACATTC CGGATATCCC TGCGCACCTA TGGTACTTCG    2400

GGTTAATTGG GACATGTCTT TAGTGGCCGG CGCGGCTGGG TCGACTCTAG CGAGCTCGAG    2460

ATCTAGAGGG TGACTGACAC CTGGCGGTAG ACAATCAATC CATTTCGCTA TAGTTAAAGG    2520

ATGGGGATGA GGGCAATTGG TTATATGATC ATGTATGTAG TGGGTGTGCA TAATAGTAGT    2580

GAAATGGAAG CCAAGTCATG TGATTGTAAT CGACCGACGG AATTGAGGAT ATCCGGAAAT    2640

ACAGACACCG TGAAAGCCAT GGTCTTTCCT TCGTGTAGAA GACCAGACAG ACAGTCCCTG    2700

ATTTACCCTT GCACAAAGCA CTAGAAAATT AGCATTCCAT CCTTCTCTGC TTGCTCTGCT    2760

GATATCACTG TCATTCAATG CATAGCCATG AGCTCATCTT AGATCCAAGC ACGTAATTCC    2820

ATAGCCGAGG TCCACAGTGG AGCAGCAACA TTCCCCATCA TTGCTTTCCC CAGGGGCCTC    2880

CCAACGACTA AATCAAGAGT ATATCTCTAC CGTCCAATAG ATCGTCTTCG CTTCAAAATC    2940

TTTGACAATT CCAAGAGGGT CCCCATCCAT CAAACCCAGT TCAATAATAG CCGAGATGCA    3000

TGGTGGAGTC AATTAGGCAG TATTGCTGGA ATGTCGGGCC AGTTGGCCCG GGTGGTCATT    3060

GGCCGCCTGT GATGCCATCT GCCACTAAAT CCGATCATTG ATCCACCGCC CACGAGGCGC    3120

GTCTTTGCTT TTTGCGCGGC GTCCAGGTTC AACTCTCTCG CTCTAGATAT CGATGAATTC    3180

ACTGGCCGTC GTTTTACAAC GTCGTGACTG GGAAAACCCT GGCGTTACCC AACTTAATCG    3240

CCTTGCAGCA CATCCCCCTT TCGCCAGCTG GCGTAATAGC GAAGAGGCCC GCACCGATCG    3300

CCCTTCCCAA CAGTTGCGCA GCCTGAATGG CGAATGGCGC CTGATGCGGT ATTTTCTCCT    3360

TACGCATCTG TGCGGTATTT CACACCGCAT ATGGTGCACT CTCAGTACAA TCTGCTCTGA    3420

TGCCGCATAG TTAAGCCAGC CCCGACACCC GCCAACACCC GCTGACGCGC CCTGACGGGC    3480

TTGTCTGCTC CCGGCATCCG CTTACAGACA AGCTGTGACC GTCTCCGGGA GCTGCATGTG    3540

TCAGAGGTTT TCACCGTCAT CACCGAAACG CGCGAGACGA AAGGGCCTCG TGATACGCCT    3600

ATTTTTATAG GTTAATGTCA TGATAATAAT GGTTTCTTAG ACGTCAGGTG GCACTTTTCG    3660

GGGAAATGTG CGCGGAACCC CTATTTGTTT ATTTTTCTAA ATACATTCAA ATATGTATCC    3720

GCTCATGAGA CAATAACCCT GATAAATGCT TCAATAATAT TGAAAAAGGA AGAGTATGAG    3780

TATTCAACAT TTCCGTGTCG CCCTTATTCC CTTTTTTGCG GCATTTTGCC TTCCTGTTTT    3840

TGCTCACCCA GAAACGCTGG TGAAAGTAAA AGATGCTGAA GATCAGTTGG GTGCACGAGT    3900

GGGTTACATC GAACTGGATC TCAACAGCGG TAAGATCCTT GAGAGTTTTC GCCCCGAAGA    3960

ACGTTTTCCA ATGATGAGCA CTTTTAAAGT TCTGCTATGT GGCGCGGTAT TATCCCGTAT    4020

TGACGCCGGG CAAGAGCAAC TCGGTCGCCG CATACACTAT TCTCAGAATG ACTTGGTTGA    4080

GCGCGTCACCA GTCACAGAAA AGCATCTTAC GGATGGCATG ACAGTAAGAG AATTATGCAG    4140

TGCTGCCATA ACCATGAGTG ATAACACTGC GGCCAACTTA CTTCTGACAA CGATCGGAGG    4200

ACCGAAGGAG CTAACCGCTT TTTTGCACAA CATGGGGGAT CATGTAACTC GCCTTGATCG    4260

TTGGGAACCG GAGCTGAATG AAGCCATACC AAACGACGAG CGTGACACCA CGATGCCTGT    4320

AGCAATGGCA ACAACGTTGC GCAAACTATT AACTGGCGAA CTACTTACTC TAGCTTCCCG    4380

GCAACAATTA ATAGACTGGA TGGAGGCGGA TAAAGTTGCA GGACCACTTC TGCGCTCGGC    4440

CCTTCCGGCT GGCTGGTTTA TTGCTGATAA ATCTGGAGCC GGTGAGCGTG GGTCTCGCGG    4500

TATCATTGCA GCACTGGGGC CAGATGGTAA GCCCTCCCGT ATCGTAGTTA TCTACACGAC    4560

GGGGAGTCAG GCAACTATGG ATGAACGAAA TAGACAGATC GCTGAGATAG GTGCCTCACT    4620

GATTAAGCAT TGGTAACTGT CAGACCAAGT TTACTCATAT ATACTTTAGA TTGATTTAAA    4680
```

```
ACTTCATTTT TAATTTAAAA GGATCTAGGT GAAGATCCTT TTTGATAATC TCATGACCAA    4740

AATCCCTTAA CGTGAGTTTT CGTTCCACTG AGCGTCAGAC CCCGTAGAAA AGATCAAAGG    4800

ATCTTCTTGA GATCCTTTTT TTCTGCGCGT AATCTGCTGC TTGCAAACAA AAAAACCACC    4860

GCTACCAGCG GTGGTTTGTT TGCCGGATCA AGAGCTACCA ACTCTTTTTC CGAAGGTAAC    4920

TGGCTTCAGC AGAGCGCAGA TACCAAATAC TGTCCTTCTA GTGTAGCCGT AGTTAGGCCA    4980

CCACTTCAAG AACTCTGTAG CACCGCCTAC ATACCTCGCT CTGCTAATCC TGTTACCAGT    5040

GGCTGCTGCC AGTGGCGATA AGTCGTGTCT TACCGGGTTG GACTCAAGAC GATAGTTACC    5100

GGATAAGGCG CAGCGGTCGG GCTGAACGGG GGGTTCGTGC ACACAGCCCA GCTTGGAGCG    5160

AACGACCTAC ACCGAACTGA GATACCTACA GCGTGAGCTA TGAGAAAGCG CCACGCTTCC    5220

CGAAGGGAGA AAGGCGGACA GGTATCCGGT AAGCGGCAGG GTCGGAACAG GAGAGCGCAC    5280

GAGGGAGCTT CCAGGGGGAA ACGCCTGGTA TCTTTATAGT CCTGTCGGGT TTCGCCACCT    5340

CTGACTTGAG CGTCGATTTT TGTGATGCTC GTCAGGGGGG CGGAGCCTAT GGAAAAACGC    5400

CAGCAACGCG GCCTTTTTAC GGTTCCTGGC CTTTTGCTGG CCTTTTGCTC ACATGTTCTT    5460

TCCTGCGTTA TCCCCTGATT CTGTGGATAA CCGTATTACC GCCTTTGAGT GAGCTGATAC    5520

CGCTCGCCGC AGCCGAACGA CCGAGCGCAG CGAGTCAGTG AGCGAGGAAG CGGAAGAGAG    5580
```

(2) INFORMATION FOR SEQ ID NO:11:

(i) SEQUENCE CHARACTERISTICS:
        (A) LENGTH: 5697 base pairs
        (B) TYPE: nucleic acid
        (C) STRANDEDNESS: single
        (D) TOPOLOGY: linear (xi) SEQUENCE DESCRIPTION: SEQ ID NO:11:

```
GCGCCCAATA CGCAAACCGC CTCTCCCCGC GCGTTGGCCG ATTCATTAAT GCAGCTGGCA      60

CGACAGGTTT CCCGACTGGA AAGCGGGCAG TGAGCGCAAC GCAATTAATG TGAGTTAGCT     120

CACTCATTAG GCACCCCAGG CTTTACACTT TATGCTTCCG GCTCGTATGT TGTGTGGAAT     180

TGTGAGCGGA TAACAATTTC ACACAGGAAA CAGCTATGAC CATGATTACG CCAAGCTTGC     240

ATGCCTGCAG GTCGACGCAT TCCGAATACG AGGCCTGATT AATGATTACA TACGCCTCCG     300

GGTAGTAGAC CGAGCAGCCG AGCCAGTTCA GCGCCTAAAA CGCCTTATAC AATTAAGCAG     360

TTAAAGAAGT TAGAATCTAC GCTTAAAAAG CTACTTAAAA ATCGATCTCG CAGTCCCGAT     420

TCGCCTATCA AAACCAGTTT AAATCAACTG ATTAAAGGTG CCGAACGAGC TATAAATGAT     480

ATAACAATAT TAAAGCATTA ATTAGAGCAA TATCAGGCCG CGCACGAAAG GCAACTTAAA     540

AAGCGAAAGC GCTCTACTAA ACAGATTACT TTTGAAAAAG GCACATCAGT ATTTAAAGCC     600

CGAATCCTTA TTAAGCGCCG AAATCAGGCA GATAAAGCCA TACAGGCAGA TAGACCTCTA     660

CCTATTAAAT CGGCTTCTAG GCGCGCTCCA TCTAAATGTT CTGGCTGTGG TGTACAGGGG     720

CATAAAATTA CGCACTACCC GAATCGATAG AACTACTCAT TTTTATATAG AAGTCAGAAT     780

TCATAGTGTT TTGATCATTT TAAATTTTTA TATGGCGGGT GGTGGGCAAC TCGCTTGCGC     840

GGGCAACTCG CTTACCGATT ACGTTAGGGC TGATATTTAC GTGAAAATCG TCAAGGGATG     900

CAAGACCAAA GTAGTAAAAC CCCGGAAGTC AACAGCATCC AAGCCCAAGT CCTTCACGGA     960

GAAACCCCAG CGTCCACATC ACGAGCGAAG GACCACCTCT AGGCATCGGA CGCACCATCC    1020

AATTAGAAGC AGCAAAGCGA AACAGCCCAA GAAAAAGGTC GGCCCGTCGG CCTTTTCTGC    1080

AACGCTGATC ACGGGCAGCG ATCCAACCAA CACCCTCCAG AGTGACTAGG GGCGGAAATT    1140

TAAAGGGATT AATTTCCACT CAACCACAAA TCACAGTCGT CCCCGGTATT GTCCTGCAGA    1200
```

```
ATGCAATTTA AACTCTTCTG CGAATCGCTT GGATTCCCCG CCCCTAGTCG TAGAGCTTAA      1260
AGTATGTCCC TTGTCGATGC GATGATACAC AACATATAAA TACTAGCAAG GGATGCCATG      1320
CTTGGAGGAT AGCAACCGAC AACATCACAT CAAGCTCTCC CTTCTCTGAA CAATAAACCC      1380
CACAGGGGGG ATCCACTAGT AACGGCCGCC AGTGTGCTGG AAAGCGACTT GAAACGCCCC      1440
AAATGAAGTC CTCCATCCTC GCCAGCGTCT TCGCCACGGG CGCCGTGGCT CAAAGTGGTC      1500
CGTGGCAGCA ATGTGGTGGC ATCGGATGGC AAGGATCGAC CGACTGTGTG TCGGGCTACC      1560
ACTGCGTCTA CCAGAACGAT TGGTACAGCC AGTGCGCTAG CGTCCAGATC CCCTCCAGCA      1620
GCACCAGCTC TCCGGTCAAC CAGCCTACCA GCACCAGCAC CACGTCCACC TCCACCACCT      1680
CGAGCCCGCC AGTCCAGCCT ACGACTCCCA GCGCTAGCCC TCCTCGTCGA CCTGTCTCGC      1740
AGGATCTGTT TAACCAGTTC AATCTCTTTG CACAGTATTC TGCAGCCGCA TACTGCGGAA      1800
AAAACAATGA TGCCCCAGCT GGTACAAACA TTACGTGCAC GGGAAATGCC TGCCCCGAGG      1860
TAGAGAAGGC GGATGCAACG TTTCTCTACT CGTTTGAAGA CTCTGGAGTG GGCGATGTCA      1920
CCGGCTTCCT TGCTCTCGAC AACACGAACA AATTGATCGT CCTCTCTTTC CGTGGCTCTC      1980
GTTCCATAGA GAACTGGATC GGGAATCTTA AGTTCCTCTT GAAAAAAATA AATGACATTT      2040
GCTCCGGCTG CAGGGGACAT GACGGCTTCA CTTCGTCCTG GAGGTCTGTA GCCGATACGT      2100
TAAGGCAGAA GGTGGAGGAT GCTGTGAGGG AGCATCCCGA CTATCGCGTG GTGTTTACCG      2160
GACATAGCTT GGGTGGTGCA TTGGCAACTG TTGCCGGAGC AGACCTGCGT GGAAATGGGT      2220
ATGATATCGA CGTGTTTTCA TATGGCGCCC CCCGAGTCGG AAACAGGGCT TTTGCAGAAT      2280
TCCTGACCGT ACAGACCGGC GGAACACTCT ACCGCATTAC CCACACCAAT GATATTGTCC      2340
CTAGACTCCC GCCGCGCGAA TTCGGTTACA GCCATTCTAG CCCAGAATAC TGGATCAAAT      2400
CTGGAACCCT TGTCCCCGTC ACCCGAAACG ATATCGTGAA GATAGAAGGC ATCGATGCCA      2460
CCGGCGGCAA TAACCGGCCG AACATTCCGG ATATCCCTGC GCACCTATGG TACTTCGGGT      2520
TAATTGGGAC ATGTCTTTAG TGGCCGGCGC GGCTGGGTCG ACTCTAGCGA GCTCGAGATC      2580
TAGAGGGTGA CTGACACCTG GCGGTAGACA ATCAATCCAT TTCGCTATAG TTAAAGGATG      2640
GGGATGAGGG CAATTGGTTA TATGATCATG TATGTAGTGG GTGTGCATAA TAGTAGTGAA      2700
ATGGAAGCCA AGTCATGTGA TTGTAATCGA CCGACGGAAT TGAGGATATC CGGAAATACA      2760
GACACCGTGA AAGCCATGGT CTTTCCTTCG TGTAGAAGAC CAGACAGACA GTCCCTGATT      2820
TACCCTTGCA CAAAGCACTA GAAAATTAGC ATTCCATCCT TCTCTGCTTG CTCTGCTGAT      2880
ATCACTGTCA TTCAATGCAT AGCCATGAGC TCATCTTAGA TCCAAGCACG TAATTCCATA      2940
GCCGAGGTCC ACAGTGGAGC AGCAACATTC CCCATCATTG CTTTCCCCAG GGGCCTCCCA      3000
ACGACTAAAT CAAGAGTATA TCTCTACCGT CCAATAGATC GTCTTCGCTT CAAAATCTTT      3060
GACAATTCCA AGAGGGTCCC CATCCATCAA ACCCAGTTCA ATAATAGCCG AGATGCATGG      3120
TGGAGTCAAT TAGGCAGTAT TGCTGGAATG TCGGGCCAGT TGGCCCGGGT GGTCATTGGC      3180
CGCCTGTGAT GCCATCTGCC ACTAAATCCG ATCATTGATC CACCGCCCAC GAGGCGCGTC      3240
TTTGCTTTTT GCGCGGCGTC CAGGTTCAAC TCTCTCGCTC TAGATATCGA TGAATTCACT      3300
GGCCGTCGTT TTACAACGTC GTGACTGGGA AAACCCTGGC GTTACCCAAC TTAATCGCCT      3360
TGCAGCACAT CCCCCTTTCG CCAGCTGGCG TAATAGCGAA GAGGCCCGCA CCGATCGCCC      3420
TTCCCAACAG TTGCGCAGCC TGAATGGCGA ATGGCGCCTG ATGCGGTATT TTCTCCTTAC      3480
GCATCTGTGC GGTATTTCAC ACCGCATATG GTGCACTCTC AGTACAATCT GCTCTGATGC      3540
CGCATAGTTA AGCCAGCCCC GACACCCGCC AACACCCGCT GACGCGCCCT GACGGGCTTG      3600
```

```
TCTGCTCCCG GCATCCGCTT ACAGACAAGC TGTGACCGTC TCCGGGAGCT GCATGTGTCA    3660

GAGGTTTTCA CCGTCATCAC CGAAACGCGC GAGACGAAAG GGCCTCGTGA TACGCCTATT    3720

TTTATAGGTT AATGTCATGA TAATAATGGT TTCTTAGACG TCAGGTGGCA CTTTTCGGGG    3780

AAATGTGCGC GGAACCCCTA TTTGTTTATT TTTCTAAATA CATTCAAATA TGTATCCGCT    3840

CATGAGACAA TAACCCTGAT AAATGCTTCA ATAATATTGA AAAAGGAAGA GTATGAGTAT    3900

TCAACATTTC CGTGTCGCCC TTATTCCCTT TTTTGCGGCA TTTTGCCTTC CTGTTTTTGC    3960

TCACCCAGAA ACGCTGGTGA AAGTAAAAGA TGCTGAAGAT CAGTTGGGTG CACGAGTGGG    4020

TTACATCGAA CTGGATCTCA ACAGCGGTAA GATCCTTGAG AGTTTTCGCC CCGAAGAACG    4080

TTTTCCAATG ATGAGCACTT TTAAAGTTCT GCTATGTGGC GCGGTATTAT CCCGTATTGA    4140

CGCCGGGCAA GAGCAACTCG GTCGCCGCAT ACACTATTCT CAGAATGACT TGGTTGACGC    4200

GTCACCAGTC ACAGAAAAGC ATCTTACGGA TGGCATGACA GTAAGAGAAT TATGCAGTGC    4260

TGCCATAACC ATGAGTGATA ACACTGCGGC CAACTTACTT CTGACAACGA TCGGAGGACC    4320

GAAGGAGCTA ACCGCTTTTT TGCACAACAT GGGGGATCAT GTAACTCGCC TTGATCGTTG    4380

GGAACCGGAG CTGAATGAAG CCATACCAAA CGACGAGCGT GACACCACGA TGCCTGTAGC    4440

AATGGCAACA ACGTTGCGCA AACTATTAAC TGGCGAACTA CTTACTCTAG CTTCCCGGCA    4500

ACAATTAATA GACTGGATGG AGGCGGATAA AGTTGCAGGA CCACTTCTGC GCTCGGCCCT    4560

TCCGGCTGGC TGGTTTATTG CTGATAAATC TGGAGCCGGT GAGCGTGGGT CTCGCGGTAT    4620

CATTGCAGCA CTGGGGCCAG ATGGTAAGCC CTCCCGTATC GTAGTTATCT ACACGACGGG    4680

GAGTCAGGCA ACTATGGATG AACGAAATAG ACAGATCGCT GAGATAGGTG CCTCACTGAT    4740

TAAGCATTGG TAACTGTCAG ACCAAGTTTA CTCATATATA CTTTAGATTG ATTTAAAACT    4800

TCATTTTTAA TTTAAAAGGA TCTAGGTGAA GATCCTTTTT GATAATCTCA TGACCAAAAT    4860

CCCTTAACGT GAGTTTTCGT TCCACTGAGC GTCAGACCCC GTAGAAAAGA TCAAAGGATC    4920

TTCTTGAGAT CCTTTTTTTC TGCGCGTAAT CTGCTGCTTG CAAACAAAAA AACCACCGCT    4980

ACCAGCGGTG GTTTGTTTGC CGGATCAAGA GCTACCAACT CTTTTTCCGA AGGTAACTGG    5040

CTTCAGCAGA GCGCAGATAC CAAATACTGT CCTTCTAGTG TAGCCGTAGT TAGGCCACCA    5100

CTTCAAGAAC TCTGTAGCAC CGCCTACATA CCTCGCTCTG CTAATCCTGT TACCAGTGGC    5160

TGCTGCCAGT GGCGATAAGT CGTGTCTTAC CGGGTTGGAC TCAAGACGAT AGTTACCGGA    5220

TAAGGCGCAG CGGTCGGGCT GAACGGGGGG TTCGTGCACA CAGCCCAGCT TGGAGCGAAC    5280

GACCTACACC GAACTGAGAT ACCTACAGCG TGAGCTATGA GAAAGCGCCA CGCTTCCCGA    5340

AGGGAGAAAG GCGGACAGGT ATCCGGTAAG CGGCAGGGTC GGAACAGGAG AGCGCACGAG    5400

GGAGCTTCCA GGGGGAAACG CCTGGTATCT TTATAGTCCT GTCGGGTTTC GCCACCTCTG    5460

ACTTGAGCGT CGATTTTTGT GATGCTCGTC AGGGGGGCGG AGCCTATGGA AAAACGCCAG    5520

CAACGCGGCC TTTTTACGGT TCCTGGCCTT TTGCTGGCCT TTTGCTCACA TGTTCTTTCC    5580

TGCGTTATCC CCTGATTCTG TGGATAACCG TATTACCGCC TTTGAGTGAG CTGATACCGC    5640

TCGCCGCAGC CGAACGACCG AGCGCAGCGA GTCAGTGAGC GAGGAAGCGG AAGAGAG      5697
```

(2) INFORMATION FOR SEQ ID NO:12:

(i) SEQUENCE CHARACTERISTICS:
        (A) LENGTH: 1620 base pairs
        (B) TYPE: nucleic acid
        (C) STRANDEDNESS: single
        (D) TOPOLOGY: linear (xi) SEQUENCE DESCRIPTION: SEQ ID NO:12:

```
GAGAAAAAAC TATAGGATCC ACTAGTAACG GCCGCCAGTG TGCTCTAAAG ACTATGAAGC      60

TCTCGCTTTT GTCCACCTTC GCTGCTGTCA TCATCGGTGC CCTCGCTCTA CCCCAGGGTT     120

GCACTGCTGA GAGGTGGGCT CAGTGCGGCG GCAATGGCTG GAGCGGCTGC ACCACCTGCG     180

TCGCTGGCAG CACTTGCACG AAGATTAATG ACTGGTACCA TCAGTGCCTG CCCTCCAGCA     240

GCACCAGCTC TCCGGTCAAC CAGCCTACCA GCACCAGCAC CACGTCCACC TCCACCACCT     300

CGAGCCCGCC AGTCCAGCCT ACGACTCCCA GCGGCCAGGG TCCTGGAGGA GGCGGGTCAG     360

TCACTTGCCC CGGTGGACAG TCCACTTCGA ACAGCCAGTG CTGCGTCTGG TTCGACGTTC     420

TAGACGATCT TCAGACCAAC TTCTACCAAG GGTCCAAGTG TGAGAGCCCT GTTCGCAAGA     480

TTCTTAGAAT TGTTTTCCAT GACGCGATCG GATTTTCGCC GGCGTTGACT GCTGCTGGTC     540

AATTCGGTGG TGGAGGAGCT GATGGCTCCA TCATTGCGCA TTCGAACATC GAATTGGCCT     600

TCCCGGCTAA TGGCGGCCTC ACCGACACCG TCGAAGCCCT CCGCGCGGTC GGTATCAACC     660

ACGGTGTCTC TTTCGGCGAT CTCATCCAAT TCGCCACTGC CGTCGGCATG TCCAACTGCC     720

CTGGCTCTCC CCGACTTGAG TTCTTGACGG GCAGGAGCAA CAGTTCCCAA CCCTCCCCTC     780

CTTCGTTGAT CCCCGGTCCC GGAAACACGG TCACCGCTAT CTTGGATCGT ATGGGCGATG     840

CAGGCTTCAG CCCTGATGAA GTAGTCGACT TGCTTGCTGC GCATAGTTTG GCTTCTCAGG     900

AGGGTTTGAA CTCGGCCATC TTCAGATCTC CTTTGGACTC GACCCCTCAA GTTTTCGATA     960

CCCAGTTCTA CATTGAGACC TTGCTCAAGG GTACCACTCA GCCTGGCCCT TCTCTCGGCT    1020

TTGCAGAGGA GCTCTCCCCC TTCCCTGGCG AATTCCGCAT GAGGTCCGAT GCTCTCTTGG    1080

CTCGCGACTC CCGAACCGCC TGCCGATGGC AATCCATGAC CAGCAGCAAT GAAGTTATGG    1140

GCCAGCGATA CCGCGCCGCC ATGGCCAAGA TGTCTGTTCT CGGCTTCGAC AGGAACGCCC    1200

TCACCGATTG CTCTGACGTT ATTCCTTCTG CTGTGTCCAA CAACGCTGCT CCTGTTATCC    1260

CTGGTGGCCT TACTGTCGAT GATATCGAGG TTTCGTGCCC GAGCGAGCCT TTCCCTGAAA    1320

TTGCTACCGC CTCAGGCCCT CTCCCCTCCC TCGCTCCTGC TCCTTGATCT GGTGAAGATG    1380

GTACATCCTG CTCTCTCATC ATCCCTCTTA GCTATTTATC CAATCTATCT ACCTATCTAT    1440

GCAGTTTCTG TTCTATCACC ACAGGAAGCA AGAAAGAAAA ACAACAATGC AACGTGAGCA    1500

GAAATCAGCA AAAAAATAAA TCAGTATACT ACAGTAATGA GGCCAGTTTG CGTGGTGTCA    1560

GAAGTAAGTA CGACTCGGCT TTACACACTG GCGGCCGCTC GAGCATGCAT CTAGAGGGCC    1620
```

(2) INFORMATION FOR SEQ ID NO:13:

(i) SEQUENCE CHARACTERISTICS:
(A) LENGTH: 1620 base pairs
(B) TYPE: nucleic acid
(C) STRANDEDNESS: single
(D) TOPOLOGY: linear (xi) SEQUENCE DESCRIPTION: SEQ ID NO:13:

```
GAGAAAAAAC TATAGGATCC ACTAGTAACG GCCGCCAGTG TGCTCTAAAG ACTATGAAGC      60

TCTCGCTTTT GTCCACCTTC GCTGCTGTCA TCATCGGTGC CCTCGCTCTA CCCCAAGGTT     120

GCACTGCTGA GAGGTGGGCT CAGTGCGGCG GCAATGGCTG GAGCGGCTGC ACCACCTGCG     180

TCGCTGGCAG CACTTGCACG AAGATTAATG ACTGGTATCA TCAGTGCCTG CCCTCCAGCA     240

GCACCAGCTC TCCGGTCAAC CAGCCTACCA GCACCAGCAC CACGTCCACC TCCACCACCT     300

CGAGCCCGCC AGTCCAGCCT ACGACTCCGA GCGGTCAGGG TCCTGGAGGA GGCGGGTCAG     360

TCACTTGCCC CGGTGGACAG TCCACTTCGA ACAGCCAGTG CTGCGTCTGG TTCGACGTTC     420
```

```
TAGACGATCT TCAGACCAAC TTCTACCAAG GGTCCAAGTG TGAGAGCCCT GTTCGCAAGA      480

TTCTTAGAAT TGTTTTCCAT GACGCGATCG GATTTTCGCC GGCGTTGACT GCTGCTGGTC      540

AATTCGGTGG TGGAGGAGCT GATGGCTCCA TCATTGCGCA TTCGAACATC GAATTGGCCT      600

TCCCGGCTAA TGGCGGCCTC ACCGACACCG TCGAAGCCCT CCGCGCGGTC GGTATCAACC      660

ACGGTGTCTC TTTCGGCGAT CTCATCCAAT TCGCCACTGC CGTCGGCATG TCCAACTGCC      720

CTGGCTCTCC CCGACTTGAG TTCTTGACGG GCAGGAGCAA CAGTTCCCAA CCCTCCCCTC      780

CTTCGTTGAT CCCCGGTCCC GGAAACACGG TCACCGCTAT CTTGGATCGT ATGGGCGATG      840

CAGGCTTCAG CCCTGATGAA GTAGTCGACT TGCTTGCTGC GCATAGTTTG GCTTCTCAGG      900

AGGGTTTGAA CTCGGCCATC TTCAGATCTC CTTTGGACTC GACCCCTCAA GTTTTCGATA      960

CCCAGTTCTA CATTGAGACC TTGCTCAAGG GTACCACTCA GCCTGGCCCT TCTCTCGGCT     1020

TTGCAGAGGA GCTCTCCCCC TTCCCTGGCG AATTCCGCAT GAGGTCCGAT GCTCTCTTGG     1080

CTCGCGACTC CCGAACCGCC TGCCGATGGC AATCCATGAC CAGCAGCAAT GAAGTTATGG     1140

GCCAGCGATA CCGCGCCGCC ATGGCCAAGA TGTCTGTTCT CGGCTTCGAC AGGAACGCCC     1200

TCACCGATTG CTCTGACGTT ATTCCTTCTG CTGTGTCCAA CAACGCTGCT CCTGTTATCC     1260

CTGGTGGCCT TACTGTCGAT GATATCGAGG TTTCGTGCCC GAGCGAGCCT TTCCCTGAAA     1320

TTGCTACCGC CTCAGGCCCT CTCCCCTCCC TCGCTCCTGC TCCTTGATCT GGTGAAGATG     1380

GTACATCCTG CTCTCTCATC ATCCCTCTTA GCTATTTATC CAATCTATCT ACCTATCTAT     1440

GCAGTTTCTG TTCTATCACC ACAGGAAGCA AGAAAGAAAA ACAACAATGC AACGTGAGCA     1500

GAAATCAGCA AAAAAATAAA TCAGTATACT ACAGTAATGA GGCCAGTTTG CGTGGTGTCA     1560

GAAGTAAGTA CGACTCGGCT TTACACACTG GCGGCCGCTC GAGCATGCAT CTAGAGGGCC     1620

(2) INFORMATION FOR SEQ ID NO:14:

(i) SEQUENCE CHARACTERISTICS:
         (A) LENGTH: 480 base pairs
         (B) TYPE: nucleic acid
         (C) STRANDEDNESS: single
         (D) TOPOLOGY: linear (xi) SEQUENCE DESCRIPTION: SEQ ID NO:14:

GAGAAAAAAC TATAGGATCC ACTAGTAACG GCCGCCAGTG TGCTCTAAAG ACTATGAAGC       60

TCTCGCTTTT GTCCACCTTC GCTGCTGTCA TCATCGGTGC CCTCGCTCTA CCCCAAGGTT      120

GCACTGCTGA GAGGTGGGCT CAGTGCGGCG GCAATGGCTG GAGCGGCTGC ACCACCTGCG      180

TCGCTGGCAG CACTTGCACG AAGATTAATG ACTGGTACCA TCAGTGCCTG CCCTCCTCCA      240

GCACCAGCTC TCCGGTCAAC CAGCCTACCA GCACCAGCTC CAGCCCTCCA GTCCAGCCTA      300

CGACTCCTAG CGGACAAGGT CCTGGAGGAG GCGGGTCAGT CACTTGCCCC GGTGGACAGT      360

CCACTTCGAA CAGCCAGTGC TGCGTCTGGT TCGACGTTCT AGACGATCTT CAGACCAACT      420

TCTACCAAGG GTCCAAGTGT GAGAGCCCTG TTCGCAAGAT CTTAGAATT GTTTTCCATG       480

(2) INFORMATION FOR SEQ ID NO:15:

(i) SEQUENCE CHARACTERISTICS:
         (A) LENGTH: 480 base pairs
         (B) TYPE: nucleic acid
         (C) STRANDEDNESS: single
         (D) TOPOLOGY: linear (xi) SEQUENCE DESCRIPTION: SEQ ID NO:15:

GAGAAAAAAC TATAGGATCC ACTAGTAACG GCCGCCAGTG TGCTCTAAAG ACTATGAAGC       60
```

```
TCTCGCTTTT GTCCACCTTC GCTGCTGTCA TCATCGGTGC CCTCGCTCTA CCCCAAGGTT      120

GCACTGCTGA GAGGTGGGCT CAGTGCGGCG GCAATGGCTG GAGCGGCTGC ACCACCTGCG      180

TCGCTGGCAG CACTTGCACG AAGATTAATG ACTGGTACCA TCAGTGCCTC GCCCCCGTCG      240

TCGCCCCCGC CCCCGCCCCC GCCCCCCAAG GTCCTGGAGG AGGCGGGTCA GTCACTTGCC      300

CCGGTGGACA GTCCACTTCG AACAGCCAGT GCTGCGTCTG GTTCGACGTT CTAGACGATC      360

TTCAGACCAA CTTCTACCAA GGGTCCAAGT GTGAGAGCCC TGTTCGCAAG ATTCTTAGAA      420

TTGTTTTCCA TGACGCGATC GGATTTTCGC CGGCGTTGAC TGCTGCTGGT CAATTCGGTG      480

(2) INFORMATION FOR SEQ ID NO:16:

(i) SEQUENCE CHARACTERISTICS:
        (A) LENGTH: 480 base pairs
        (B) TYPE: nucleic acid
        (C) STRANDEDNESS: single
        (D) TOPOLOGY: linear (xi) SEQUENCE DESCRIPTION: SEQ ID NO:16:

GAGAAAAAAC TATAGGATCC ACTAGTAACG GCCGCCAGTG TGCTCTAAAG ACTATGAAGC       60

TCTCGCTTTT GTCCACCTTC GCTGCTGTCA TCATCGGTGC CCTCGCTCTA CCCCAAGGTT      120

GCACTGCTGA GAGGTGGGCT CAGTGCGGCG GCAATGGCTG GAGCGGCTGC ACCACCTGCG      180

TCGCTGGCAG CACTTGCACG AAGATTAATG ACTGGTACCA TCAGTGCCTG CAAGCCCCCC      240

AACAGAGCCC CCGCATCGAA CGTCCACGCG CTCAGGGTCC TGGAGGAGGC GGGTCAGTCA      300

CTTGCCCCGG TGGACAGTCC ACTTCGAACA GCCAGTGCTG CGTCTGGTTC GACGTTCTAG      360

ACGATCTTCA GACCAACTTC TACCAAGGGT CCAAGTGTGA GAGCCCTGTT CGCAAGATTC      420

TTAGAATTGT TTTCCATGAC GCGATCGGAT TTTCGCCGGC GTTGACTGCT GCTGGTCAAT      480

(2) INFORMATION FOR SEQ ID NO:17:

(i) SEQUENCE CHARACTERISTICS:
        (A) LENGTH: 2279 base pairs
        (B) TYPE: nucleic acid
        (C) STRANDEDNESS: single
        (D) TOPOLOGY: linear (xi) SEQUENCE DESCRIPTION: SEQ ID NO:17:

CTGGGGTAAT TAATCAGCGA AGCGATGATT TTTGATCTAT TAACAGATAT ATAAATGCAA       60

AAACTGCATA ACCACTTTAA CTAATACTTT CAACATTTTC GGTTTGTATT ACTTCTTATT      120

CAAATGTAAT AAAAGTATCA ACAAAAAATT GTTAATATAC CTCTATACTT TAACGTCAAG      180

GAGAAAAAAC TATAGGATCC ACTAGTAACG GCCGCCAGTG TGCTCTAAAG ACTATGAAGC      240

TCTCGCTTTT GTCCACCTTC GCTGCTGTCA TCATCGGTGC CCTCGCTCTA CCCCAGGGTT      300

GCACTGCTGA GAGGTGGGCT CAGTGCGGCG GCAATGGCTG GAGCGGCTGC ACCACCTGCG      360

TCGCTGGCAG CACTTGCACG AAGATTAATG ACTGGTACCA TCAGTGCCTG CAAGCCCCCC      420

AACAGAGCCC CCGCATCGAA CGTCCACGCG CTCAGCAGAG CTGCAACACC CCAGCAACC      480

GGGCGTGCTG GACTGACGGA TACGACATCA ACACCGACTA CGAAGTGGAC AGCCCGGACA      540

CGGGTGTTGT TCGGCCTTAT ACTCTGACTC TCACCGAAGT CGACAACTGG ACCGGACCTG      600

ATGGCGTCGT CAAGGAGAAG GTCATGCTGG TTAACAATAG TATAATCGGA CCAACAATCT      660

TTGCGGACTG GGGCGACACG ATCCAGGTAA CGGTCATCAA CAACCTCGAG ACCAACGGCA      720

CGTCGATCCA CTGGCACGGA CTGCACCAGA AGGGCACCAA CCTGCACGAC GGCGCCAACG      780

GTATCACCGA GTGCCCGATC CCGCCCAAGG GAGGGAGGAA GGTGTACCGG TTCAAGGCTC      840
```

```
AGCAGTACGG GACGAGCTGG TACCACTCGC ACTTCTCGGC CCAGTACGGC AACGGCGTGG     900

TCGGGGCCAT TCAGATCAAC GGGCCGGCCT CGCTGCCGTA CGACACCGAC CTGGGCGTGT     960

TCCCCATCAG CGACTACTAC TACAGCTCGG CCGACGAGCT GGTGGAACTC ACCAAGAACT    1020

CGGGCGCGCC CTTCAGCGAC AACGTCCTGT TCAACGGCAC GGCCAAGCAC CCGGAGACGG    1080

GCGAGGGCGA GTACGCCAAC GTGACGCTCA CCCCGGGCCG GCGGCACCGC CTGCGCCTGA    1140

TCAACACGTC GGTCGAGAAC CACTTCCAGG TCTCGCTCGT CAACCACACC ATGACCATCA    1200

TCGCCGCCGA CATGGTGCCC GTCAACGCCA TGACGGTCGA CAGCCTCTTC CTCGGCGTCG    1260

GCCAGCGCTA CGATGTCGTC ATCGAAGCCA GCCGAACGCC CGGGAACTAC TGGTTTAACG    1320

TCACATTTGG CGGCGGCCTG CTCTGCGGCG GCTCCAGGAA TCCCTACCCG GCCGCCATCT    1380

TCCACTACGC CGGCGCCCCC GGCGGCCCGC CCACGGACGA GGGCAAGGCC CCGGTCGACC    1440

ACAACTGCCT GGACCTCCCC AACCTCAAGC CCGTCGTGGC CCGCGACGTG CCCCTGAGCG    1500

GCTTCGCCAA GCGGCCCGAC AACACGCTCG ACGTCACCCT CGACACCACG GGCACGCCCC    1560

TGTTCGTCTG GAAGGTCAAC GGCAGCGCCA TCAACATCGA CTGGGGCAGG CCCGTCGTCG    1620

ACTACGTCCT CACGCAGAAC ACCAGCTTCC CACCCGGGTA CAACATTGTC GAGGTGAACG    1680

GAGCTGATCA GTGGTCGTAC TGGTTGATCG AGAATGATCC CGGCGCACCT TTCACCCTAC    1740

CGCATCCGAT GCACCTGCAC GGCCACGACT TTTACGTGCT GGGCCGCTCG CCCGACGAGT    1800

CGCCGGCATC CAACGAGCGG CACGTGTTCG ATCCGGCGCG GGACGCGGGC CTGCTGAGCG    1860

GGGCCAACCC TGTGCGGCGG GACGTGACGA TGCTGCCGGC GTTCGGGTGG GTGGTGCTGG    1920

CCTTCCGGGC CGACAACCCG GGCGCCTGGC TGTTCCACTG CCACATCGCC TGGCACGTCT    1980

CGGGCGGCCT GGGCGTCGTC TACCTCGAGC GCGCCGACGA CCTGCGCGGG GCCGTCTCGG    2040

ACGCCGACGC CGACGACCTC GACCGCCTCT GCGCCGACTG GCGCCGCTAC TGGCCTACCA    2100

ACCCCTACCC CAAGTCCGAC TCGGGCCTCA AGCACCGCTG GGTCGAGGAG GGCGAGTGGC    2160

TGGTCAAGGC GTGAGCGAAG GAGGAAAAAG GCGGCCGCAT AGTATAGGCC GCTCGAGCAT    2220

GCATCTAGAG GGCCGCATCA TGTAATTAGT TATGTCACGC TTACATTCAC GCCCTCCCC     2279

(2) INFORMATION FOR SEQ ID NO:18:

(i) SEQUENCE CHARACTERISTICS:
        (A) LENGTH: 2300 base pairs
        (B) TYPE: nucleic acid
        (C) STRANDEDNESS: single
        (D) TOPOLOGY: linear (xi) SEQUENCE DESCRIPTION: SEQ ID NO:18:

CTGGGGTAAT TAATCAGCGA AGCGATGATT TTTGATCTAT TAACAGATAT ATAAATGCAA      60

AAACTGCATA ACCACTTTAA CTAATACTTT CAACATTTTC GGTTTGTATT ACTTCTTATT     120

CAAATGTAAT AAAAGTATCA ACAAAAAATT GTTAATATAC CTCTATACTT TAACGTCAAG     180

GAGAAAAAAC TATAGGATCC CCAACATGAG GTCCTTCATC AGCGCCGCGA CGCTTTTGGT     240

GGGCATTCTC ACCCCTAGCG TTGCTGCTGC CCCTCCATCC ACCCCTGAGC AGCGCGACCT     300

GCTCGTCCCG ATCACGGAGA GGGAGGAGGC AGCCGTGAAG GCTCGCCAGC AGAGCTGCAA     360

CACCCCCAGC AACCGGGCGT GCTGGACTGA CGGATACGAC ATCAACACCG ACTACGAAGT     420

GGACAGCCCG GACACGGGTG TTGTTCGGCC TTATACTCTG ACTCTCACCG AAGTCGACAA     480

CTGGACCGGA CCTGATGGCG TCGTCAAGGA GAAGGTCATG CTGGTTAACA ATAGTATAAT     540

CGGACCAACA ATCTTTGCGG ACTGGGGCGA CACGATCCAG GTAACGGTCA TCAACAACCT     600
```

```
CGAGACCAAC GGCACGTCGA TCCACTGGCA CGGACTGCAC CAGAAGGGCA CCAACCTGCA        660

CGACGGCGCC AACGGTATCA CCGAGTGCCC GATCCCGCCC AAGGGAGGGA GGAAGGTGTA        720

CCGGTTCAAG GCTCAGCAGT ACGGGACGAG CTGGTACCAC TCGCACTTCT CGGCCCAGTA        780

CGGCAACGGC GTGGTCGGGG CCATTCAGAT CAACGGGCCG GCCTCGCTGC CGTACGACAC        840

CGACCTGGGC GTGTTCCCCA TCAGCGACTA CTACTACAGC TCGGCCGACG AGCTGGTGGA        900

ACTCACCAAG AACTCGGGCG CGCCCTTCAG CGACAACGTC CTGTTCAACG GCACGGCCAA        960

GCACCCGGAG ACGGGCGAGG GCGAGTACGC CAACGTGACG CTCACCCCGG GCCGGCGGCA       1020

CCGCCTGCGC CTGATCAACA CGTCGGTCGA GAACCACTTC CAGGTCTCGC TCGTCAACCA       1080

CACCATGACC ATCATCGCCG CCGACATGGT GCCCGTCAAC GCCATGACGG TCGACAGCCT       1140

CTTCCTCGGC GTCGGCCAGC GCTACGATGT CGTCATCGAA GCCAGCCGAA CGCCCGGGAA       1200

CTACTGGTTT AACGTCACAT TTGGCGGCGG CCTGCTCTGC GGCGGCTCCA GGAATCCCTA       1260

CCCGGCCGCC ATCTTCCACT ACGCCGGCGC CCCCGGCGGC CGCCCACGG ACGAGGGCAA        1320

GGCCCCGGTC GACCACAACT GCCTGGACCT CCCCAACCTC AAGCCCGTCG TGGCCCGCGA       1380

CGTGCCCCTG AGCGGCTTCG CCAAGCGGCC CGACAACACG CTCGACGTCA CCCTCGACAC       1440

CACGGGCACG CCCCTGTTCG TCTGGAAGGT CAACGGCAGC GCCATCAACA TCGACTGGGG       1500

CAGGCCCGTC GTCGACTACG TCCTCACGCA GAACACCAGC TTCCCACCCG GGTACAACAT       1560

TGTCGAGGTG AACGGAGCTG ATCAGTGGTC GTACTGGTTG ATCGAGAATG ATCCCGGCGC       1620

ACCTTTCACC CTACCGCATC CGATGCACCT GCACGGCCAC GACTTTTACG TGCTGGGCCG       1680

CTCGCCCGAC GAGTCGCCGG CATCCAACGA GCGGCACGTG TTCGATCCGG CGCGGGACGC       1740

GGGCCTGCTG AGCGGGGCCA ACCCTGTGCG GCGGGACGTG ACGATGCTGC CGGCGTTCGG       1800

GTGGGTGGTG CTGGCCTTCC GGGCCGACAA CCCGGGCGCC TGGCTGTTCC ACTGCCACAT       1860

CGCCTGGCAC GTCTCGGGCG GCCTGGGCGT CGTCTACCTC GAGCGCGCCG ACGACCTGCG       1920

CGGGGCCGTC TCGGACGCCG ACGCCGACGA CCTCGACCGC CTCTGCGCCG ACTGGCGCCG       1980

CTACTGGCCT ACCAACCCCT ACCCCAAGTC CGACTCGGGC CTCAAGCACC GCTGGGTCGA       2040

GGAGGGCGAG TGGCTGGTCA AGGCGCCCTC CAGCAGCACC AGCTCTCCGG TCAACCAGCC       2100

TACCAGCACC AGCACCACGT CCACCTCCAC CACCTCGAGC CCGCCAGTCC AGCCTACGAC       2160

TCCCAGCGGC TGCACTGCTG AGAGGTGGGC TCAGTGCGGC GGCAATGGCT GGAGCGGCTG       2220

CACCACCTGC GTCGCTGGCA GCACTTGCAC GAAGATTAAT GACTGGTACC ATCAGTGCCT       2280

GTAGGCGGCC GCATTCTTAT                                                  2300

(2) INFORMATION FOR SEQ ID NO:19:

(i) SEQUENCE CHARACTERISTICS:
            (A) LENGTH: 2249 base pairs
            (B) TYPE: nucleic acid
            (C) STRANDEDNESS: single
            (D) TOPOLOGY: linear (xi) SEQUENCE DESCRIPTION: SEQ ID NO:19:

CTGGGGTAAT TAATCAGCGA AGCGATGATT TTTGATCTAT TAACAGATAT ATAAATGCAA         60

AAACTGCATA ACCACTTTAA CTAATACTTT CAACATTTTC GGTTTGTATT ACTTCTTATT        120

CAAATGTAAT AAAAGTATCA ACAAAAAATT GTTAATATAC CTCTATACTT TAACGTCAAG        180

GAGAAAAAAC TATAGGATCC CCAACATGAG GTCCTTCATC AGCGCCGCGA CGCTTTTGGT        240

GGGCATTCTC ACCCCTAGCG TTGCTGCTGC CCCTCCATCC ACCCCTGAGC AGCGCGACCT        300

GCTCGTCCCG ATCACGGAGA GGGAGGAGGC AGCCGTGAAG GCTCGCCAGC AGAGCTGCAA        360
```

```
CACCCCCAGC AACCGGGCGT GCTGGACTGA CGGATACGAC ATCAACACCG ACTACGAAGT      420

GGACAGCCCG GACACGGGTG TTGTTCGGCC TTATACTCTG ACTCTCACCG AAGTCGACAA      480

CTGGACCGGA CCTGATGGCG TCGTCAAGGA GAAGGTCATG CTGGTTAACA ATAGTATAAT      540

CGGACCAACA ATCTTTGCGG ACTGGGGCGA CACGATCCAG GTAACGGTCA TCAACAACCT      600

CGAGACCAAC GGCACGTCGA TCCACTGGCA CGGACTGCAC CAGAAGGGCA CCAACCTGCA      660

CGACGGCGCC AACGGTATCA CCGAGTGCCC GATCCCGCCC AAGGGAGGGA GGAAGGTGTA      720

CCGGTTCAAG GCTCAGCAGT ACGGGACGAG CTGGTACCAC TCGCACTTCT CGGCCCAGTA      780

CGGCAACGGC GTGGTCGGGG CCATTCAGAT CAACGGCCG GCCTCGCTGC CGTACGACAC      840

CGACCTGGGC GTGTTCCCCA TCAGCGACTA CTACTACAGAC TCGGCCGACG AGCTGGTGGA      900

ACTCACCAAG AACTCGGGCG CGCCCTTCAG CGACAACGTC CTGTTCAACG GCACGGCCAA      960

GCACCCGGAG ACGGGCGAGG GCGAGTACGC CAACGTGACG CTCACCCCGG GCCGGCGGCA     1020

CCGCCTGCGC CTGATCAACA CGTCGGTCGA GAACCACTTC CAGGTCTCGC TCGTCAACCA     1080

CACCATGACC ATCATCGCCG CCGACATGGT GCCCGTCAAC GCCATGACGG TCGACAGCCT     1140

CTTCCTCGGC GTCGGCCAGC GCTACGATGT CGTCATCGAA GCCAGCCGAA CGCCCGGGAA     1200

CTACTGGTTT AACGTCACAT TTGGCGGCGG CCTGCTCTGC GGCGGCTCCA GGAATCCCTA     1260

CCCGGCCGCC ATCTTCCACT ACGCCGGCGC CCCCGGCGGC CCGCCCACGG ACGAGGGCAA     1320

GGCCCCGGTC GACCACAACT GCCTGGACCT CCCCAACCTC AAGCCCGTCG TGGCCCGCGA     1380

CGTGCCCCTG AGCGGCTTCG CCAAGCGGCC CGACAACACG CTCGACGTCA CCCTCGACAC     1440

CACGGGCACG CCCCTGTTCG TCTGGAAGGT CAACGGCAGC GCCATCAACA TCGACTGGGG     1500

CAGGCCCGTC GTCGACTACG TCCTCACGCA GAACACCAGC TTCCCACCCG GGTACAACAT     1560

TGTCGAGGTG AACGGAGCTG ATCAGTGGTC GTACTGGTTG ATCGAGAATG ATCCCGGCGC     1620

ACCTTTCACC CTACCGCATC CGATGCACCT GCACGGCCAC GACTTTTACG TGCTGGGCCG     1680

CTCGCCCGAC GAGTCGCCGG CATCCAACGA GCGGCACGTG TTCGATCCGG CGCGGGACGC     1740

GGGCCTGCTG AGCGGGGCCA ACCCTGTGCG GCGGGACGTG ACGATGCTGC CGGCGTTCGG     1800

GTGGGTGGTG CTGGCCTTCC GGGCCGACAA CCCGGGCGCC TGGCTGTTCC ACTGCCACAT     1860

CGCCTGGCAC GTCTCGGGCG GCCTGGGCGT CGTCTACCTC GAGCGCGCCG ACGACCTGCG     1920

CGGGGCCGTC TCGGACGCCG ACGCCGACGA CCTCGACCGC CTCTGCGCCG ACTGGCGCCG     1980

CTACTGGCCT ACCAACCCCT ACCCCAAGTC CGACCCCTCC AGCAGCACCA GCTCTCCGGT     2040

CAACCAGCCT ACCAGCACCA GCACCACGTC CACCTCCACC ACCTCGAGCC CGCCAGTCCA     2100

GCCTACGACT CCCAGCGGCT GCACTGCTGA GAGGTGGGCT CAGTGCGGCG GCAATGGCTG     2160

GAGCGGCTGC ACCACCTGCG TCGCTGGCAG CACTTGCACG AAGATTAATG ACTGGTACCA     2220

TCAGTGCCTG TAGGCGGCCG CATTCTTAT                                      2249
```

(2) INFORMATION FOR SEQ ID NO:20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:20:

```
GCTTTACGCC CGATTGCTGA CGCTG                                            25
```

(2) INFORMATION FOR SEQ ID NO:21:

(i) SEQUENCE CHARACTERISTICS:
    (A) LENGTH: 51 base pairs
    (B) TYPE: nucleic acid
    (C) STRANDEDNESS: single
    (D) TOPOLOGY: linear (xi) SEQUENCE DESCRIPTION: SEQ ID NO:21:

GCGATGAGAC GCGCGGCCGC CTATCTTTGA ACATAAATTG AAACGGATCC G           51

(2) INFORMATION FOR SEQ ID NO:22:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO:22:

GCTGCAGGAT CCGTTTCAAT TTATGTTCAA AGATCTGGCG GACCTGGAAC GCCAAATAAT    60

GGAAGAGG                                                            68

(2) INFORMATION FOR SEQ ID NO:23:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:23:

GCACTAGCTA GACGGCCGCT ACCAGTCAAC ATTAACAGGA CCTGAG                  46

(2) INFORMATION FOR SEQ ID NO:24:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:24:

GTAGGCTCAG TCATATGTTA CACATTGAAA GGGGAGGAGA ATCATGAAAA AGATAACTAC    60

TATTTTTGTC G                                                        71

(2) INFORMATION FOR SEQ ID NO:25:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:25:

GTACCTCGCG GGTACCAAGC GGCCGCTTAA TTGAGTGGTT CCCACGGACC G            51

(2) INFORMATION FOR SEQ ID NO:26:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO:26:

GCTGCAGGAT CCGTTTCAAT TTATGTTCAA AGATCTCCTG GAGAGTATCC AGCATGGGAC    60

CCAA    64

(2) INFORMATION FOR SEQ ID NO:27:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:27:

GCACAAGCTT GCGGCCGCTA ATTGAGTGGT TCCCACGGAC CG    42

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:28:

CTCGTCCCAA TCGGTTCCGT C    21

(2) INFORMATION FOR SEQ ID NO:29:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:29:

TGCACTGGTA CAGTTCCTAC AACTAGTCCT ACACGTGCAA ATCTTAATGG GACGCTG    57

(2) INFORMATION FOR SEQ ID NO:30:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:30:

CTGCCTCATT CTGCAGCAGC GGCGGCAAAT CTTAATGCTC CCGGCTGCCG CGTCGACTAC    60

(2) INFORMATION FOR SEQ ID NO:31:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:31:

TGTAGGAACT GTACCAGTGC ACGTGGTGCC GTTGAGC    37

(2) INFORMATION FOR SEQ ID NO:32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:32:

ACGTAGTGGC CACGCTAGGC GAGGTGGTGG        30

(2) INFORMATION FOR SEQ ID NO:33:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

CCACACTTCT CTTCCTTCCT C        21

(2) INFORMATION FOR SEQ ID NO:34:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO:34:

Asn Asn Asn Pro Gln Gln Gly Asn Pro Asn Gln Gly Gly Asn Asn Gly
1               5                   10                  15

Gly Gly Asn Gln Gly Gly Gly Asn Gly Gly
            20                  25

(2) INFORMATION FOR SEQ ID NO:35:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:35:

GATCTAGCTA GCAACAATAA CCCCCAGCAG GGCAACCCCA ACCAGGGCGG GAACAACGGC        60

(2) INFORMATION FOR SEQ ID NO:36:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

GATCTAGCTA GCGCCGCCGT TGCCGCCGCC CTGGTTGCCG CCGCCGTTGT TCCCGCCCTG        60

(2) INFORMATION FOR SEQ ID NO:37:

(i) SEQUENCE CHARACTERISTICS:
        (A) LENGTH: 37 amino acids
        (B) TYPE: amino acid
        (C) STRANDEDNESS: single
        (D) TOPOLOGY: linear (xi) SEQUENCE DESCRIPTION: SEQ ID NO:37:

Val Gln Ile Pro Ser Ser Ser Thr Ser Ser Pro Val Asn Gln Pro Thr
1               5                   10                  15

Ser Thr Ser Thr Thr Ser Thr Ser Thr Thr Ser Ser Pro Pro Val Gln
            20                  25                  30

Pro Thr Thr Pro Ser
         35

(2) INFORMATION FOR SEQ ID NO:38:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:38:

GATACTGCTA GCGTCCAGAT CCCCTCCAGC                                            30

(2) INFORMATION FOR SEQ ID NO:39:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:39:

GATACTGCTA GCGCTGGGAG TCGTAGGCTG                                            30

(2) INFORMATION FOR SEQ ID NO:40:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:40:

CCCCCTTCCC TGGCGAATTC CGCATGAGG                                             29

(2) INFORMATION FOR SEQ ID NO:41:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:41:

ACCTTGGGGT AGAGCGAGGG CACCGATG                                              28

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:42:

TGCACTGCTG AGAGGTGGGC                                                       20

(2) INFORMATION FOR SEQ ID NO:43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:43:

```
CAGGCACTGA TGATACCAGT                                                    20

(2) INFORMATION FOR SEQ ID NO:44:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (xi) SEQUENCE DESCRIPTION: SEQ ID NO:44:

CCCTCCAGCA GCACCAGCTC T                                                  21

(2) INFORMATION FOR SEQ ID NO:45:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (xi) SEQUENCE DESCRIPTION: SEQ ID NO:45:

TCCTCCAGGA CCCTGACCGC TCGGAGTCGT AGGCTG                                  36

(2) INFORMATION FOR SEQ ID NO:46:

(i) SEQUENCE CHARACTERISTICS:
         (A) LENGTH: 37 base pairs
         (B) TYPE: nucleic acid
         (C) STRANDEDNESS: single
         (D) TOPOLOGY: linear (xi) SEQUENCE DESCRIPTION: SEQ ID NO:46:

TACGACTCCG AGCGGTCAGG GTCCTGGAGG AGGCGGG                                 37

(2) INFORMATION FOR SEQ ID NO:47:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (xi) SEQUENCE DESCRIPTION: SEQ ID NO:47:

GGGAGGGCGT GAATGTAAG                                                     19

(2) INFORMATION FOR SEQ ID NO:48:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (xi) SEQUENCE DESCRIPTION: SEQ ID NO:48:

CTGGGGTAAT TAATCAGCGA AGCGATG                                            27

(2) INFORMATION FOR SEQ ID NO:49:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (xi) SEQUENCE DESCRIPTION: SEQ ID NO:49:

AGCGCGTGGA CGTTCGATGC                                                    20
```

(2) INFORMATION FOR SEQ ID NO:50:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:50:

CAGCAGAGCT GCAACACCCC CAG        23

(2) INFORMATION FOR SEQ ID NO:51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:51:

GGGGAGGGCG TGAATGTAAG        20

(2) INFORMATION FOR SEQ ID NO:52:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:52:

CTGGGGTAAT TAATCAGCGA AGCGATG        27

(2) INFORMATION FOR SEQ ID NO:53:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:53:

CGCCTTGACC AGCCACTCGC CCTCCTCG        28

(2) INFORMATION FOR SEQ ID NO:54:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:54:

CCCTCCAGCA GCACCAGCTC TC        22

(2) INFORMATION FOR SEQ ID NO:55:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:55:

ATAAGAATGC GGCCGCCTAC AGGCACTGAT GGTACCAGT        39

PROCESS FOR REMOVAL OR BLEACHING OF SOILING OR STAINS FROM CELLULOSIC FABRIC

CROSS-REFERENCE TO RELATED APPLICATIONS

This application is a continuation of application Ser. No. PCT/DK97/00042 filed Jan. 29, 1997 and claims priority under 35 U.S.C. 119 of Danish application serial no. 0094/96 filed Jan. 29, 1996, the contents of which are fully incorporated herein by reference.

FIELD OF THE INVENTION

The present invention relates to an improved enzymatic process for cleaning fabric or textile, notably cellulosic fabric or textile, particularly for removing or bleaching stains present on cellulosic fabric.

BACKGROUND OF THE INVENTION

Enzymatic processes for washing clothes (laundry washing) and other types of fabric or textile have been known for many years.

Certain types of soiling or stains have generally been found to be problematical to remove in such washing procedures. These are typically stains originating from starch, proteins, fats, red wine, fruit (such as blackcurrant, cherry, strawberry or tomato), vegetables (such as carrot or beetroot), tea, coffee, spices (such as curry or paprika), body fluids, grass, or ink (e.g. from ball-point pens or fountain pens).

It is an object of the present invention to improve the performance of a washing enzyme under conventional washing conditions by modifying the enzyme so as to alter (increase) the affinity of the enzyme for cellulosic fabric, whereby the modified enzyme is believed to be able to come into closer contact, and/or more lasting contact, with the soiling or stain in question.

SUMMARY OF THE INVENTION

It has now surprisingly been found possible to achieve improved cleaning of cellulosic fabric or textile, particularly improved removal or bleaching of stains present thereon, by means of an enzymatic process wherein the fabric or textile is contacted with an enzyme which has been modified so as to have increased affinity (relative to the unmodified enzyme) for binding to a cellulosic fabric or textile.

DETAILED DESCRIPTION OF THE INVENTION

The present invention thus relates, inter alia, to a process for removal or bleaching of soiling or stains present on cellulosic fabric or textile, wherein the fabric or textile is contacted in aqueous medium with a modified enzyme (enzyme hybrid) which comprises a catalytically (enzymatically) active amino acid sequence of a non-cellulolytic enzyme linked to an amino acid sequence comprising a cellulose-binding domain.

Stains

Soiling or stains which may be removed according to the present invention include those already mentioned above, i.e. soiling or stains originating from, for example, starch, proteins, fats, red wine, fruit [such as blackcurrant, cherry, strawberry or tomato (in particular tomato in ketchup or spaghetti sauce)], vegetables (such as carrot or beetroot), tea, coffee, spices (such as curry or paprika), body fluids, grass, or ink (e.g. from ball-point pens or fountain pens). Other types of soiling or stains which are appropriate targets for removal or bleaching in accordance with the invention include sebum, soil (i.e. earth), clay, oil and paint.

Cellulosic fabric

The term "cellulosic fabric" is intended to indicate any type of fabric, in particular woven fabric, prepared from a cellulose-containing material, such as cotton, or from a cellulose-derived material (prepared, e.g., from wood pulp or from cotton).

In the present context, the term "fabric" is intended to include garments and other types of processed fabrics, and is used interchangeably with the term "textile".

Examples of cellulosic fabric manufactured from naturally occurring cellulosic fibre are cotton, ramie, jute and flax (linen) fabrics. Examples of cellulosic fabrics made from man-made cellulosic fibre are viscose (rayon) and lyocell (e.g. Tencel™) fabric; also of relevance in the context of the invention are all blends of cellulosic fibres (such as viscose, lyocell, cotton, ramie, jute or flax) with other fibres, e.g. with animal hair fibres such as wool, alpaca or camel hair, or with polymer fibres such as polyester, polyacrylic, polyamide or polyacetate fibres.

Specific examples of blended cellulosic fabric are viscose/cotton blends, lyocell/cotton blends (e.g. Tencel™/cotton blends), viscose/wool blends, lyocell/wool blends, cotton/wool blends, cotton/polyester blends, viscose/cotton/polyester blends, wool/cotton/polyester blends, and flax/cotton blends.

Cellulose-binding domains

Although a number of types of carbohydrate-binding domains have been described in the patent and scientific literature, the majority thereof—many of which derive from cellulolytic enzymes (cellulases)—are commonly referred to as "cellulose-binding domains"; a typical cellulose-binding domain (CBD) will thus be one which occurs in a cellulase and which binds preferentially to cellulose and/or to poly- or oligosaccharide fragments thereof.

Cellulose-binding (and other carbohydrate-binding) domains are polypeptide amino acid sequences which occur as integral parts of large polypeptides or proteins consisting of two or more polypeptide amino acid sequence regions, especially in hydrolytic enzymes (hydrolases) which typically comprise a catalytic domain containing the active site for substrate hydrolysis and a carbohydrate-binding domain for binding to the carbohydrate substrate in question. Such enzymes can comprise more than one catalytic domain and one, two or three carbohydrate-binding domains, and they may further comprise one or more polypeptide amino acid sequence regions linking the carbohydrate-binding domain(s) with the catalytic domain(s), a region of the latter type usually being denoted a "linker".

Examples of hydrolytic enzymes comprising a cellulose-binding domain are cellulases, xylanases, mannanases, arabinofuranosidases, acetylesterases and chitinases. "Cellulose-binding domains" have also been found in algae, e.g. in the red alga *Porphyra purpurea* in the form of a non-hydrolytic polysaccharide-binding protein [see P. Tomme et al., *Cellulose-Binding Domains—Classification and Properties* in *Enzymatic Degradation of Insoluble Carbohydrates*, John N. Saddler and Michael H. Penner (Eds.), ACS Symposium Series, No. 618 (1996)]. However, most of the known CBDs [which are classified and referred to by P. Tomme et al. (op cit.) as "cellulose-binding domains"] derive from cellulases and xylanases.

In the present context, the term "cellulose-binding domain" is intended to be understood in the same manner as in the latter reference (P. Tomme et al., op. cit). The P. Tomme et al. reference classifies more than 120 "cellulose-binding domains" into 10 families (I-X) which may have different functions or roles in connection with the mechanism of substrate binding. However, it is to be anticipated that new family representatives and additional families will appear in the future, and in connection with the present invention a representative of one such new CBD family has in fact been identified (see Example 2 herein).

In proteins/polypeptides in which CBDs occur (e.g. enzymes, typically hydrolytic enzymes such as cellulases), a CBD may be located at the N or C terminus or at an internal position.

That part of a polypeptide or protein (e.g. hydrolytic enzyme) which constitutes a CBD per se typically consists of more than about 30 and less than about 250 amino acid residues. For example: those CBDs listed and classified in Family I in accordance with P. Tomme et al. (op. cit.) consist of 33–37 amino acid residues, those listed and classified in Family IIa consist of 95–108 amino acid residues, those listed and classified in Family VI consist of 85–92 amino acid residues, whilst one CBD (derived from a cellulase from *Clostridium thertnocellum*) listed and classified in Family VII consists of 240 amino acid residues. Accordingly, the molecular weight of an amino acid sequence constituting a CBD per se will typically be in the range of from about 4 kD to about 40 kD, and usually below about 35 kD.

Enzyme hybrids

Enzyme classification numbers (EC numbers) referred to in the present specification with claims are in accordance with the *Recommendations* (1992) *of the Nomenclature Committee of the International Union of Biochemistry and Molecular Biology*, Academic Press Inc., 1992.

A modified enzyme (enzyme hybrid) for use in accordance with the invention comprises a catalytically active (enzymatically active) amino acid sequence (in general a polypeptide amino acid sequence) of a non-cellulolytic enzyme (i.e. a catalytically active amino acid sequence of an enzyme other than a cellulase) useful in relation to the cleaning of fabric or textile (typically the removal or bleaching of soiling or stains from fabrics or textiles in washing processes), in particular of an enzyme selected from the group consisting of amylases (e.g. α-amylases, EC 3.2.1.1), proteases (i.e. peptidases, EC 3.4), lipases (e.g. triacylglycerol lipases, EC 3.1.1.3) and oxidoreductases (e.g. peroxidases, EC 1.11.1, such as those classified under EC 1.11.1.7; or phenol-oxidizing oxidases, such as laccases, EC 1.10.3.2, or other enzymes classified under EC 1.10.3), fused (linked) to an amino acid sequence comprising a cellulose-binding domain. The catalytically active amino acid sequence in question may comprise or consist of the whole of—or substantially the whole of—the full amino acid sequence of the mature enzyme in question, or it may consist of a portion of the full sequence which retains substantially the same catalytic (enzymatic) properties as the full sequence.

Modified enzymes (enzyme hybrids) of the type in question, as well as detailed descriptions of the preparation and purification thereof, are known in the art [see, e.g., WO 90/00609, WO 94/24158 and WO 95/16782, as well as Greenwood et al., *Biotechnology and Bioengineering* 44 (1994) pp. 1295–1305]. They may, e.g., be prepared by transforming into a host cell a DNA construct comprising at least a fragment of DNA encoding the cellulose-binding domain ligated, with or without a linker, to a DNA sequence encoding the enzyme of interest, and growing the transformed host cell to express the fused gene. One relevant, but non-limiting, type of recombinant product (enzyme hybrid) obtainable in this manner—often referred to in the art as a "fusion protein"—may be described by one of the following general formulae:

A-CBD-MR-X-B

A-X-MR-CBD-B

In the latter formulae, CBD is an amino acid sequence comprising at least the cellulose-binding domain (CBD) per se.

MR (the middle region; a linker) may be a bond, or a linking group comprising from 1 to about 100 amino acid residues, in particular of from 2 to 40 amino acid residues, e.g. from 2 to 15 amino acid residues. MR may, in principle, alternatively be a non-amino-acid linker.

X is an amino acid sequence comprising the above-mentioned, catalytically (enzymatically) active sequence of amino acid residues of a polypeptide encoded by a DNA sequence encoding the non-cellulolytic enzyme of interest.

The moieties A and B are independently optional. When present, a moiety A or B constitutes a terminal extension of a CBD or X moiety, and normally comprises one or more amino acid residues.

It will thus, inter alia, be apparent from the above that a CBD in an enzyme hybrid of the type in question may be positioned C-terminally, N-terminally or internally in the enzyme hybrid. Correspondingly, an X moiety in an enzyme hybrid of the type in question may be positioned N-terminally, C-terminally or internally in the enzyme hybrid.

Enzyme hybrids of interest in the context of the invention include enzyme hybrids which comprise more than one CBD, e.g. such that two or more CBDs are linked directly to each other, or are separated from one another by means of spacer or linker sequences (consisting typically of a sequence of amino acid residues of appropriate length). Two CBDs in an enzyme hybrid of the type in question may, for example, also be separated from one another by means of an -MR-X- moiety as defined above.

A very important issue in the construction of enzyme hybrids of the type in question is the stability towards proteolytic degradation. Two- and multi-domain proteins are particularly susceptible towards proteolytic cleavage of linker regions connecting the domains. Proteases causing such cleavage may, for example, be subtilisins, which are known to often exhibit broad substrate specificities [see, e.g.: Grøn et al., *Biochemistry* 31 (1992), pp. 6011–6018; Teplyakov et al., *Protein Engineering* 5 (1992), pp. 413–420].

Glycosylation of linker residues in eukaryotes is one of Nature's ways of preventing proteolytic degradation. Another is to employ amino acids which are less favoured by the surrounding proteases. The length of the linker also plays a role in relation to accessibility by proteases. Which "solution" is optimal depends on the environment in which the enzyme hybrid is to function.

When constructing new enzyme hybrid molecules, linker stability thus becomes an issue of great importance. The various linkers described in examples presented herein (vide infra) in the context of the present invention are intended to take account of this issue.

Cellulases (cellulase genes) useful for preparation of CBDs

Techniques suitable for isolating a cellulase gene are well known in the art. In the present context, the terms "cellulase" and "cellulolytic enzyme" refer to an enzyme which catalyses the degradation of cellulose to glucose, cellobiose, triose and/or other cello-oligosaccharides.

Preferred cellulases (i.e. cellulases comprising preferred CBDs) in the present context are microbial cellulases, particularly bacterial or fungal cellulases. Endoglucanases, notably endo-1,4-β-glucanases (EC 3.2.1.4), particularly monocomponent (recombinant) endo-1,4-β-glucanases, are a preferred class of cellulases,.

Useful examples of bacterial cellulases are cellulases derived from or producible by bacteria from the group consisting of Pseudomonas, Bacillus, Cellulomonas, Clostridium, Microspora, Thermotoga, Caldocellum and Actinomycets such as Streptomyces, Termomonospora and Acidothemus, in particular from the group consisting of *Pseudomonas cellulolyticus, Bacillus lautus, Cellulomonas fimi, Clostridium thermocellum, Microspora bispora, Termomonospora fusca, Termomonospora cellulolyticum* and *Acidothemus cellulolyticus.*

The cellulase may be an acid, a neutral or an alkaline cellulase, i.e. exhibiting maximum cellulolytic activity in the acid, neutral or alkaline range, respectively.

A useful cellulase is an acid cellulase, preferably a fungal acid cellulase, which is derived from or producible by fungi from the group of genera consisting of Trichoderma, Myrothecium, Aspergillus, Phanaerochaete, Neurospora, Neocallimastix and Botrytis.

A preferred useful acid cellulase is one derived from or producible by fungi from the group of species consisting of *Trichoderma viride, Trichoderma reesei, Trichoderma longibrachiatum, Myrothecium verrucaria, Aspergillus niger, Aspergillus oryzae, Phanaerochaete chrysosporium, Neurospora crassa, Neocallimastix partriciarum* and *Botrytis cinerea.*

Another useful cellulase is a neutral or alkaline cellulase, preferably a fungal neutral or alkaline cellulase, which is derived from or producible by fungi from the group of genera consisting of Aspergillus, Penicillium, Myceliophthora, Humicola, Irpex, Fusarium, Stachybotrys, Scopulariopsis, Chaetomium, Mycogone, Verticillium, Myrothecium, Papulospora, Gliocladium, Cephalosporium and Acremonium.

A preferred alkaline cellulase is one derived from or producible by fungi from the group of species consisting of *Humicola insolens, Fusarium oxysporum, Myceliopthora thermophila, Penicillium janthinellum* and Cephalosporium sp., preferably from the group of species consisting of *Humicola insolens* DSM 1800, *Fusarium oxysporum* DSM 2672, *Myceliopthora thermophila* CBS 117.65, and Cephalosporium sp. RYM-202.

A preferred cellulase is an alkaline endoglucanase which is immunologically reactive with an antibody raised against a highly purified ~43 kD endoglucanase derived from *Humicola insolens* DSM 1800, or which is a derivative of the latter ~43 kD endoglucanase and exhibits cellulase activity.

Other examples of useful cellulases are variants of parent cellulases of fungal or bacterial origin, e.g. variants of a parent cellulase derivable from a strain of a species within one of the fungal genera Humicola, Trichoderma or Fusarium.

Isolation of a cellulose-binding domain

In order to isolate a cellulose-binding domain of, e.g., a cellulase, several genetic engineering approaches may be used. One method uses restriction enzymes to remove a portion of the gene and then to fuse the remaining gene-vector fragment in frame to obtain a mutated gene that encodes a protein truncated for a particular gene fragment. Another method involves the use of exonucleases such as Bal31 to systematically delete nucleotides either externally from the 5' and the 3' ends of the DNA or internally from a restricted gap within the gene. These gene-deletion methods result in a mutated gene encoding a shortened gene molecule whose expression product may then be evaluated for substrate-binding (e.g. cellulose-binding) ability. Appropriate substrates for evaluating the binding ability include cellulosic materials such as Avicel™ and cotton fibres. Other methods include the use of a selective or specific protease capable of cleaving a CBD, e.g. a terminal CBD, from the remainder of the polypeptide chain of the protein in question As already indicated (vide supra), once a nucleotide sequence encoding the substrate-binding (carbohydrate-binding) region has been identified, either as cDNA or chromosomal DNA, it may then be manipulated in a variety of ways to fuse it to a DNA sequence encoding the enzyme or enzymatically active amino acid sequence of interest. The DNA fragment encoding the carbohydrate-binding amino acid sequence, and the DNA encoding the enzyme or enzymatically active amino acid sequence of interest are then ligated with or without a linker. The resulting ligated DNA may then be manipulated in a variety of ways to achieve expression. Preferred microbial expression hosts include certain Aspergillus species (e.g. *A. niger* or *A. oryzae*), Bacillus species, and organisms such as *Escherichia coli* or *Saccharomyces cerevisiae.*

Amylolytic enzymes

Amylases (e.g. α- or β-amylases) which are appropriate as the basis for enzyme hybrids of the types employed in the context of the present invention include those of bacterial or fungal origin. Chemically or genetically modified mutants of such amylases are included in this connection. Relevant α-amylases include, for example, α-amylases obtainable from Bacillus species, in particular a special strain of *B. licheniformis*, described in more detail in GB 1296839. Relevant commercially available amylases include Duramyl™, Termamyl™, Fungamyl™ and BAN™ (all available from Novo Nordisk A/S, Bagsvaerd, Denmark), and Rapidase™ and Maxamyl™ P (available from Gist-Brocades, Holland).

Other useful amylolytic enzymes are CGTases (cyclodextrin glucanotransferases, EC 2.4.1.19), e.g. those obtainable from species of Bacillus, Thermoanaerobactor or Thermoanaerobacterium.

Proteolytic enzymes

Proteases (peptidases) which are appropriate as the basis for enzyme hybrids of the types employed in the context of the present invention include those of animal, vegetable or microbial origin. Proteases of microbial origin are preferred. Chemically or genetically modified mutants of such proteases are included in this connection. The protease may be a serine protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270.

Relevant commercially available protease enzymes include Alcalase™, Savinase™, Primase, Durazym™ and Esperase™ (all available from Novo Nordisk A/S, Bagsvaerd, Denmark), Maxatase™, Maxacal™, Maxapem™ and Properase™ (available from Gist-Brocades, Holland), Purafect™ and Purafect™ OXP (available from Genencor International), and Opticlean™ and Optimase™ (available from by Solvay Enzymes).

Lipolytic enzymes

Lipolytic enzymes (lipases) which are appropriate as the basis for enzyme hybrids of the types employed in the context of the present invention include those of bacterial or fungal origin. Chemically or genetically modified mutants of such lipases are included in this connection.

Examples of useful lipases include a *Humicola lanuginosa* lipase, e.g. as described in EP 258 068 and EP 305 216; a *Rhizomucor miehei* lipase, e.g. as described in EP 238 023; a Candida lipase, such as a *C. antarctica* lipase, e.g. the *C. antarctica* lipase A or B described in EP 214 761; a Pseudomonas lipase, such as one of those described in EP 721 981 (e.g. a lipase obtainable from a Pseudomonas sp. SD705 strain having deposit accession number FERM BP-4772), in PCT/JP96/00426, in PCT/JP96/00454 (e.g. a *P. solanacearum* lipase), in EP 571 982 or in WO 95/14783 (e.g. a *P. mendocina* lipase), a *P. alcaligenes* or *P. pseudoalcaligenes* lipase, e.g. as described in EP 218 272, a *P. cepacia* lipase, e.g. as described in EP 331 376, a *P. stutzeri* lipase, e.g. as disclosed in GB 1,372,034, or a *P. fluorescens* lipase; a Bacillus lipase, e.g. a *B. subtilis* lipase [Dartois et al., *Biochemica et Biophysica Acta* 1131 (1993) pp. 253–260], a *B. stearothermophilus* lipase (JP 64/744992) and a *B. pumilus* lipase (WO 91/16422).

Furthermore, a number of cloned lipases may be useful, including the *Penicillium camembertii* lipase described by Yamaguchi et al. in *Gene* 103 (1991), pp. 61–67, the *Geotricum candidum* lipase [Y. Schimada et al., *J. Biochem.* 106 (1989), pp. 383–388], and various Rhizopus lipases such as an *R. delemar* lipase [M. J. Hass et al., *Gene* 109 (1991) pp. 117–113], an *R. niveus* lipase [Kugimiya et al., *Biosci. Biotech. Biochem.* 56 (1992), pp. 716–719] and a *R. oryzae* lipase.

Other potentially useful types of lipolytic enzymes include cutinases, e.g. a cutinase derived from *Pseudomonas mendocina* as described in WO 88/09367, or a cutinase derived from *Fusarium solani* f. pisi (described, e.g., in WO 90/09446).

Suitable commercially available lipases include Lipolase™ and Lipolase Ultra™ (available from Novo Nordisk A/S), M1 Lipase™, Lumafast™ and Lipomax™ (available from Gist-Brocades) and Lipase P "Amano" (available from Amano Pharmaceutical Co. Ltd.).

Oxidoreductases

Oxidoreductases which are appropriate as the basis for enzyme hybrids of the types employed in the context of the present invention include peroxidases (EC 1.11.1) and oxidases, such as laccases (EC 1.10.3.2) and certain related enzymes.

Peroxidases

Peroxidases (EC 1.11.1) are enzymes acting on a peroxide (e.g. hydrogen peroxide) as acceptor. Very suitable peroxidases are those classified under EC 1.11.1.7, or any fragment derived therefrom, exhibiting peroxidase activity. Synthetic or semisynthetic derivatives thereof (e.g. with porphyrin ring systems, or microperoxidases, cf., for example, U.S. Pat. No. 4,077,768, EP 537 381, WO 91/05858 and WO 92/16634) may also be of value in the context of the invention.

Very suitable peroxidases are peroxidases obtainable from plants (e.g. horseradish peroxidase or soy bean peroxidase) or from microorganisms, such as fungi or bacteria. In this respect, some preferred fungi include strains belonging to the subdivision Deuteromycotina, class Hyphomycetes, e.g. Fusarium, Humicola, Tricoderma, Myrothecium, Verticillum, Arthromyces, Caldariomyces, Ulocladium, Embellisia, Cladosporium or Dreschlera, in particular *Fusarium oxysporum* (DSM 2672), *Humicola insolens*, *Trichoderma resii*, *Myrothecium verrucana* (IFO 6113), *Verticillum alboatrum*, *Verticillum dahlie*, *Arthromyces ramosus* (FERM P-7754), *Caldariomyces fumago*, *Ulocladium chartarum*, *Embellisia alli* or *Dreschlera halodes*.

Other preferred fungi include strains belonging to the subdivision Basidiomycotina, class Basidiomycetes, e.g. Coprinus, Phanerochaete, Coriolus or Trametes, in particular *Coprinus cinereus* f. *microsporus* (IFO 8371), *Coprinus macrorhizus*, *Phanerochaete chrysosporium* (e.g. NA-12) or *Trametes versicolor* (e.g. PR4 28-A).

Further preferred fungi include strains belonging to the subdivision Zygomycotina, class Mycoraceae, e.g. Rhizopus or Mucor, in particular *Mucor hiemalis*.

Some preferred bacteria include strains of the order Actinomycetales, e.g. *Streptomyces spheroides* (ATTC 23965), *Streptomyces thermoviolaceus* (IFO 12382) or *Streptoverticillum verticillium* ssp. *verticillium*.

Other preferred bacteria include *Bacillus pumilus* (ATCC 12905), *Bacillus stearothermophilus*, *Rhodobacter sphaeroides*, *Rhodomonas palustri*, *Streptococcus lactis*, *Pseudomonas purrocinia* (ATCC 15958) or *Pseudomonas fluorescens* (NRRL B-11).

Further preferred bacteria include strains belonging to Myxococcus, e.g. *M. virescens*.

Other potential sources of useful particular peroxidases are listed in B. C. Saunders et al., *Peroxidase*, London 1964, pp. 41–43.

The peroxidase may furthermore be one which is producible by a method comprising cultivating a host cell—transformed with a recombinant DNA vector which carries a DNA sequence encoding said peroxidase as well as DNA sequences encoding functions permitting the expression of the DNA sequence encoding the peroxidase—in a culture medium under conditions permitting the expression of the peroxidase, and recovering the peroxidase from the culture.

A suitable recombinantly produced peroxidase is a peroxidase derived from a Coprinus sp., in particular *C. macrorhizus* or *C. cinereus* according to WO 92/16634, or a variant thereof, e.g. a variant as described in WO 94/12621.

Oxidases and related enzymes

Preferred oxidases in the context of the present invention are oxidases classified under EC 1.10.3, which are oxidases employing molecular oxygen as acceptor (i.e. enzymes catalyzing oxidation reactions in which molecular oxygen functions as oxidizing agent).

As indicated above, laccases (EC 1.10.3.2) are very suitable oxidases in the context of the invention. Examples of other useful oxidases in the context of the invention include the catechol oxidases (EC 1.10.3.1) and bilirubin oxidases (EC 1.3.3.5). Further useful, related enzymes include monophenol monooxygenases (EC 1.14.18.1).

Laccases are obtainable from a variety of plant and microbial sources, notably from bacteria and fungi (including filamentous fungi and yeasts), and suitable examples of laccases are to found among those obtainable from fungi, including laccases obtainable from strains of Aspergillus, Neurospora (e.g. *N. crassa*), Podospora, Botrytis, Collybia, Fomes, Lentinus, Pleurotus, Trametes (e.g. *T. villosa* or *T. versicolor* [some species/strains of Trametes being known by various names and/or having previously been classified within other genera; e.g. *Trametes villosa*=*T. pinsitus*=*Polyporus pinsitis* (also known as *P. pinsitus* or *P. villosus*)=*Coriolus pinsitus*], Polyporus, Rhizoctonia (e.g. *R. solani*), Coprinus (e.g. *C. plicatilis* or *C. cinereus*), Psatyrella, Myceliophthora (e.g. *M. thermophila*), Schytalidium, Phlebia (e.g. *P. radita*; see WO 92/01046), Coriolus (e.g. *C.hirsutus*; see JP 2-238885), Pyricularia or Rigidoporus.

Preferred laccases in the context of the invention include laccase obtainable from species/strains of Trametes (e.g. *T. villosa*), Myceliophthora (e.g. *M. thermophila*), Schytalidium or Polyporus.

Other enzymes

Further classes of enzymes which are appropriate as the basis for enzyme hybrids of the types employed in the context of the present invention include pectinases (polygalacturonases; EC 3.2.1.15).

Plasmids

Preparation of plasmids capable of expressing fusion proteins having the amino acid sequences derived from fragments of more than one polypeptide is well known in the art (see, for example, WO 90/00609 and WO 95/16782). The expression cassette may be included within a replication system for episomal maintenance in an appropriate cellular host or may be provided without a replication system, where it may become integrated into the host genome. The DNA may be introduced into the host in accordance with known techniques such as transformation, microinjection or the like.

Once the fused gene has been introduced into the appropriate host, the host may be grown to express the fused gene. Normally it is desirable additionally to add a signal sequence which provides for secretion of the fused gene. Typical examples of useful fused genes are:

Signal sequence—(pro-peptide)—carbohydrate-binding domain—linker—enzyme sequence of interest, or Signal sequence—(pro-peptide)—enzyme sequence of interest—linker—carbohydrate-binding domain, in which the pro-peptide sequence normally contains 5–100, e.g. 5–25, amino acid residues.

The recombinant product may be glycosylated or non-glycosylated.

Detergent compositions

Surfactant system

The detergent compositions according to the present invention comprise a surfactant system, wherein the surfactant can be selected from nonionic and/or anionic and/or cationic and/or ampholytic and/or zwitterionic and/or semi-polar surfactants.

The surfactant is typically present at a level from 0.1% to 60% by weight. The surfactant is preferably formulated to be compatible with enzyme hybrid and enzyme components present in the composition. In liquid or gel compositions the surfactant is most preferably formulated in such a way that it promotes, or at least does not degrade, the stability of any enzyme hybrid or enzyme in these compositions.

Suitable systems for use according to the present invention comprise as a surfactant one or more of the nonionic and/or anionic surfactants described herein.

Polyethylene, polypropylene, and polybutylene oxide conden-sates of alkyl phenols are suitable for use as the nonionic surfactant of the surfactant systems of the present invention, with the polyethylene oxide condensates being pre-ferred. These compounds include the condensation products of alkyl phenols having an alkyl group containing from about 6 to about 14 carbon atoms, preferably from about 8 to about 14 carbon atoms, in either a straight chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available nonionic surfactants of this type include Igepal™ CO-630, marketed by the GAF Corporation; and Triton™ X-45, X-114, X-100, and X-102, all marketed by the Rohm & Haas Company. These surfactants are commonly referred to as alkylphenol alkoxylates (e.g., alkyl phenol ethoxylates).

The condensation products of primary and secondary aliphatic alcohols with about 1 to about 25 moles of ethylene oxide are suitable for use as the nonionic surfactant of the nonionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available nonionic surfactants of this type include Tergitol™ 15-S-9 (The condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3.0 moles of ethylene oxide), Neodol™ 45-7 (the condensation product of $C_{14}$–$C_{15}$ linear alcohol with 7 moles of ethylene oxide), Neodol™ 45-5 (the condensation product of $C_{14}$–$C_{15}$ linear alcohol with 5 moles of ethylene oxide) marketed by Shell Chemical Company, Kyro™ EOB (the condensation product of $C_{13}$–$C_{15}$ alcohol with 9 moles ethylene oxide), marketed by The Procter & Gamble Company, and Genapol LA 050 (the condensation product of $C_{12}$–$C_{14}$ alcohol with 5 moles of ethylene oxide) marketed by Hoechst. Preferred range of HLB in these products is from 8–11 and most preferred from 8–10.

Also useful as the nonionic surfactant of the surfactant systems of the present invention are alkylpolysaccharides disclosed in U.S. Pat. No. 4,565,647, having a hydrophobic group containing from about 6 to about 30 carbon atoms, preferably from about 10 to about 16 carbon atoms and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6-positions on the preceding saccharide units.

The preferred alkylpolyglycosides have the formula

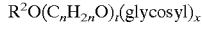

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, pre-ferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4-, and/or 6-position, preferably predominantly the 2-position.

The condensation products of ethylene oxide with a hydrophobic base formed by the condensation of propylene oxide with propylene glycol are also suitable for use as the additional nonionic surfactant systems of the present invention. The hydrophobic portion of these compounds will preferably have a molecular weight from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic™ compounds, marketed by BASF.

Preferred for use as the nonionic surfactant of the surfactant systems of the present invention are polyethylene oxide condensates of alkyl phenols, condensation products of primary and secondary aliphatic alcohols with from about 1 to about 25 moles of ethyleneoxide, alkylpolysaccharides, and mixtures hereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Highly preferred nonionic surfactants are polyhydroxy fatty acid amide surfactants of the formula

wherein $R^1$ is H, or $R^1$ is $C_{1-4}$ hydrocarbyl, 2-hydroxyethyl, 2-hydroxypropyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is straight $C_{11-15}$ alkyl or $C_{16-18}$ alkyl or alkenyl chain such as coconut alkyl or mixtures thereof, and Z is derived from a reducing sugar such as glucose, fructose, maltose or lactose, in a reductive amination reaction.

Highly preferred anionic surfactants include alkyl alkoxylated sulfate surfactants. Examples hereof are water soluble salts or acids of the formula $RO(A)_mSO_3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydro-xyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, trimethyl-ammonium cations and quaternary ammonium cations such as tetramethyl-ammonium and dimethyl piperdinium cations and those derived from alkylamines such as ethylamine, diethylamine, triethylamine, mixtures thereof, and the like. Exemplary surfactants are $C_{12}$–$C_{18}$ alkyl polyethoxylate (1.0) sulfate ($C_{12}$–$C_{18}$E(1.0)M), $C_{12}$–$C_{18}$ alkyl polyethoxylate (2.25) sulfate ($C_{12}$–$C_{18}$(2.25)M, and $C_{12}$–$C_{18}$ alkyl polyethoxylate (3.0) sulfate ($C_{12}$–$C_{18}$E(3.0)M), and $C_{12}$–$C_{18}$ alkyl polyethoxylate (4.0) sulfate ($C_{12}$–$C_{18}$E(4.0)M), wherein M is conveniently selected from sodium and potassium.

Suitable anionic surfactants to be used are alkyl ester sulfonate surfactants including linear esters of $C_8$–$C_{20}$ carboxylic acids (i.e., fatty acids) which are sulfonated with gaseous $SO_3$ according to "The Journal of the American Oil Chemists Society", 52 (1975), pp. 323–329. Suitable starting materials would include natural fatty substances as derived from tallow, palm oil, etc.

The preferred alkyl ester sulfonate surfactant, especially for laundry applications, comprise alkyl ester sulfonate surfactants of the structural formula:

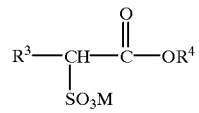

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethonolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other suitable anionic surfactants include the alkyl sulfate surfactants which are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of $C_{12}$–$C_{16}$ are preferred for lower wash temperatures (e.g. below about 50° C.) and $C_{16}$–$C_{18}$ alkyl chains are preferred for higher wash temperatures (e.g. above about 50° C.).

Other anionic surfactants useful for detersive purposes can also be included in the laundry detergent compositions of the present invention. Theses can include salts (including, for example, sodium, potassium, ammonium, and substituted ammonium salts such as mono- di- and triethanolamine salts) of soap, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{8}$ monoesters) and diesters of sulfosuccinates (especially saturated and unsaturated $C_6$–$C_{12}$ diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the formula $RO(CH_2CH_2O)_k$—$CH_2COO$—M+ wherein R is a $C_8$–$C_{22}$ alkyl, k is an integer from 1 to 10, and M is a soluble salt forming cation. Resin acids and hydrogenated resin acids are also suitable, such as rosin, hydrogenated rosin, and resin acids and hydrogenated resin acids present in or derived from tall oil.

Alkylbenzene sulfonates are highly preferred. Especially preferred are linear (straight-chain) alkyl benzene sulfonates (LAS) wherein the alkyl group preferably contains from 10 to 18 carbon atoms.

Further examples are described in "Surface Active Agents and Detergents" (Vol. I and II by Schwartz, Perrry and Berch). A variety of such surfactants are also generally disclosed in U.S. Pat. No. 3,929,678, (Column 23, line 58 through Column 29, line 23, herein incorporated by reference).

When included therein, the laundry detergent compositions of the present invention typically comprise from about 1% to about 40%, preferably from about 3% to about 20% by weight of such anionic surfactants.

The laundry detergent compositions of the present invention may also contain cationic, ampholytic, zwitterionic, and semi-polar surfactants, as well as the nonionic and/or anionic surfactants other than those already described herein.

Cationic detersive surfactants suitable for use in the laundry detergent compositions of the present invention are those having one long-chain hydrocarbyl group. Examples of such cationic surfactants include the ammonium surfactants such as alkyltrimethylammonium halogenides, and those surfactants having the formula:

$$[R^2(OR^3)_y][R^4(OR^3)_y]_2R^5N+X—$$

wherein $R^2$ is an alkyl or alkyl benzyl group having from about 8 to about 18 carbon atoms in the alkyl chain, each $R^3$ is selected form the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$–$C_4$ alkyl, $C_1$–$C_4$ hydroxyalkyl, benzyl ring structures formed by joining the two $R^4$ groups, —$CH_2CHOHCHOHCOR^6CHOHCH_2OH$, wherein $R^6$ is any hexose or hexose polymer having a molecular weight less than about 1000, and hydrogen when y is not 0; $R^5$ is the same as $R^4$ or is an alkyl chain, wherein the total number of carbon atoms or $R^2$ plus $R^5$ is not more than about 18; each y is from 0 to about 10,and the sum of the y values is from 0 to about 15; and X is any compatible anion.

Highly preferred cationic surfactants are the water soluble quaternary ammonium compounds useful in the present composition having the formula:

  (i)

wherein $R_1$ is $C_8$–$C_{16}$ alkyl, each of $R_2$, $R_3$ and $R_4$ is independently $C_1$–$C_4$ alkyl, $C_1$–$C_4$ hydroxy alkyl, benzyl, and —$(C_2H_{40})_xH$ where x has a value from 2 to 5, and X is an anion. Not more than one of $R_2$, $R_3$ or $R_4$ should be benzyl.

The preferred alkyl chain length for $R_1$ is $C_{12}$–$C_{15}$, particularly where the alkyl group is a mixture of chain lengths derived from coconut or palm kernel fat or is derived synthetically by olefin build up or OXO alcohols synthesis.

Preferred groups for $R_2R_3$ and $R_4$ are methyl and hydroxyethyl groups and the anion X may be selected from halide, methosulphate, acetate and phosphate ions.

Examples of suitable quaternary ammonium compounds of formulae (i) for use herein are:

coconut trimethyl ammonium chloride or bromide;

coconut methyl dihydroxyethyl ammonium chloride or bromide;

decyl triethyl ammonium chloride;

decyl dimethyl hydroxyethyl ammonium chloride or bromide;

$C_{12-15}$ dimethyl hydroxyethyl ammonium chloride or bromide;

coconut dimethyl hydroxyethyl ammonium chloride or bromide;

myristyl trimethyl ammonium methyl sulphate;

lauryl dimethyl benzyl ammonium chloride or bromide;

lauryl dimethyl (ethenoxy)$_4$ ammonium chloride or bromide;

choline esters (compounds of formula (i) wherein $R_1$ is

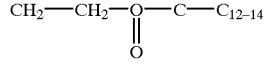

alkyl and $R_2R_3R_4$ are methyl).

di-alkyl imidazolines [compounds of formula (i)].

Other cationic surfactants useful herein are also described in U.S. Pat. No. 4,228,044 and in EP 000 224.

When included therein, the laundry detergent compositions of the present invention typically comprise from 0.2% to about 25%, preferably from about 1% to about 8% by weight of such cationic surfactants.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. pat. No. 3,929,678 (column 19, lines 18–35) for examples of ampholytic surfactants.

When included therein, the laundry detergent compositions of the present invention typically comprise from 0.2% to about 15%, preferably from about 1% to about 10% by weight of such ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 (column 19, line 38 through column 22, line 48) for examples of zwitterionic surfactants.

When included therein, the laundry detergent compositions of the present invention typically comprise from 0.2% to about 15%, preferably from about 1% to about 10% by weight of such zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula:

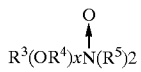

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3: and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

When included therein, the laundry detergent compositions of the present invention typically comprise from 0.2% to about 15%, preferably from about 1% to about 10% by weight of such semi-polar nonionic surfactants.

Builder system

The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g. SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenle-enschrift 2,446,686 and 2,446,487, U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2,-ethane tetracarboxylates, 1,1,3,3-propane tetracarboxylates containing sulfo substituents include the sulfosuccinate derivatives disclosed in British Patent Nos. 1,398,421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis-cis-tetracarboxylates, cyclopentadienide pentacarboxylates, 2,3,4,5-tetrahydro-furan—cis, cis, cis-tetracarboxylates, 2,5-tetrahydro-furan-cis, discarboxylates, 2,2,5,5,-tetrahydrofuran—tetracarboxylates, 1,2,3,4,5,6-hexane—hexacarboxylates and carboxymethyl derivatives of polyhydric alcohols such as sorbitol, mannitol and xylitol. Aromatic polycarboxylates include mellitic acid, pyromellitic acid and the phthalic acid derivatives disclosed in British Patent No. 1,425,343.

Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

A suitable chelant for inclusion in the detergent compositions in accordance with the invention is ethylenediamine-N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include $Na_2EDDS$ and $Na_4EDDS$. Examples of such preferred magnesium salts of EDDS include MgEDDS and $Mg_2EDDS$. The magnesium salts are the most preferred for inclusion in compositions in accordance with the invention.

Preferred builder systems include a mixture of a water-insoluble aluminosilicate builder such as zeolite A, and a water soluble carboxylate chelating agent such as citric acid.

Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated form each other by not more than two carbon atoms.

Polymers of this type are disclosed in GB-A-1,596,756. Examples of such salts are polyacrylates of MW 2000–5000 and their copolymers with maleic anhydride, such copolymers having a molecular weight of from 20,000 to 70,000, especially about 40,000.

Detergency builder salts are normally included in amounts of from 5% to 80% by weight of the composition. Preferred levels of builder for liquid detergents are from 5% to 30%.

Enzymes

In addition to the enzyme hybrid(s) in question, detergent compositions of the invention may comprise other enzymes which provide cleaning performance and/or fabric care benefits. Such enzymes include proteases, lipases, cutinases, amylases, cellulases, peroxidases and oxidases (e.g. laccases).

Proteases: Any protease suitable for use in alkaline solutions may, for example, be used. Suitable proteases include those of animal, vegetable or microbial origin. Microbial origin is preferred. Chemically or genetically modified mutants are included. The protease may be a serine protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270.

Preferred commercially available protease enzymes include those sold under the trade names Alcalase, Savinase, Primase, Durazym, and Esperase by Novo Nordisk A/S (Denmark), those sold under the tradename Maxatase, Maxacal, Maxapem, Properase, Purafect and Purafect OXP by Genencor International, and those sold under the tradename Opticlean and Optimase by Solvay Enzymes. Protease enzymes may be incorporated into the compositions in accordance with the invention at a level of from 0.00001% to 2% of enzyme protein by weight of the composition, suitably at a level of from 0.0001% to 1% of enzyme protein by weight of the composition, such as at a level of from 0.001% to 0.5% of enzyme protein by weight of the composition, appropriately at a level of from 0.01% to 0.2% of enzyme protein by weight of the composition.

Lipases: Any lipase suitable for use in alkaline solutions may, for example, be used. Suitable lipases include those of bacterial or fungal origin. Chemically or genetically modified mutants are included.

Examples of useful lipases include a *Humicola lanuginosa* lipase, e.g., as described in EP 258 068 and EP 305 216, a *Rhizomucor miehei* lipase, e.g., as described in EP 238 023, a Candida lipase, such as a *C. antarctica* lipase, e.g., the *C. antarctica* lipase A or B described in EP 214 761, a Pseudomonas lipase such as a *P. alcaligenes* and *P. pseudoalcaligenes* lipase, e.g. as described in EP 218 272, a *P. cepacia* lipase, e.g., as described in EP 331 376, a *P. stutzeri* lipase, e.g., as disclosed in GB 1,372,034, a *P. fluorescens* lipase, a Bacillus lipase, e.g., a *B. subtilis* lipase (Dartois et al., (1993), Biochemica et Biophysica acta 1131, 253–260), a *B. stearothermophilus* lipase (JP 64/744992) and a *B. pumilus* lipase (WO 91/16422).

Furthermore, a number of cloned lipases may be useful, including the *Penicillium camembertii* lipase described by Yamaguchi et al., (1991), Gene 103, 61–67), the *Geotricum candidum* lipase (Schimada, Y. et al., (1989), J. Biochem., 106, 383–388), and various Rhizopuslipases such as a *R. delemarlipase* (Hass, M. J et al., (1991), Gene 109, 117–113), a *R. niveus* lipase (Kugimiya et al., (1992), Biosci. Biotech. Biochem. 56, 716–719) and a *R. oryzae* lipase.

Other types of lipolytic enzymes such as cutinases may also be useful, e.g., a cutinase derived from *Pseudomonas mendocina* as described in WO 88/09367, or a cutinase derived from *Fusarium solani pisi* (e.g. described in WO 90/09446).

Especially suitable lipases are lipases such as M1 Lipase™, Luma fast™ and Lipomax™ (Genencor), Lipolase™ and Lipolase Ultra™ (Novo Nordisk A/S), and Lipase P "Amano" (Amano Pharmaceutical Co. Ltd.).

The lipases are normally incorporated in the detergent composition at a level of from 0.00001% to 2% of enzyme protein by weight of the composition, such as at a level of from 0.0001% to 1% of enzyme protein by weight of the composition, e.g. at a level of from 0.001% to 0.5% of enzyme protein by weight of the composition, appropriately at a level of from 0.01% to 0.2% of enzyme protein by weight of the composition.

Amylases: Any amylase (e.g. α- and/or β-) suitable for use in alkaline solutions may, for example, be used. Suitable amylases include those of bacterial or fungal origin. Chemically or genetically modified mutants are included. Amylases include, for example, α-amylases obtained from a special strain of *B. licheniformis*, described in more detail in GB 1,296,839. Commercially available amylases are Duramyl™, Termamyl™, Fungamyl™ and BAN™ (available from Novo Nordisk A/S) and Rapidase™ and Maxamyl P™ (available from Genencor).

The amylases are normally incorporated in the detergent composition at a level of from 0.00001% to 2% of enzyme protein by weight of the composition, such as at a level of from 0.0001% to 1% of enzyme protein by weight of the composition, e.g. at a level of from 0.001% to 0.5% of enzyme protein by weight of the composition, appopriately at a level of from 0.01% to 0.2% of enzyme protein by weight of the composition.

Cellulases: Any cellulase suitable for use in alkaline solutions may, for example, be used. Suitable cellulases include those of bacterial or fungal origin. Chemically or genetically modified mutants are included. Suitable cellulases are disclosed in U.S. Pat No. 4,435,307, which discloses fungal cellulases produced from *Humicola insolens*. Especially suitable cellulases are the cellulases having colour care benefits. Examples of such cellulases are cellulases described in European patent application No. 0 495 257.

Commercially available cellulases include Celluzyme™ produced by a strain of *Humicola insolens*, (Novo Nordisk A/S), and KAC-500(B)™ (Kao Corporation).

Cellulases are normally incorporated in the detergent composition at a level of from 0.00001% to 2% of enzyme protein by weight of the composition, such as at a level of from 0.0001% to 1% of enzyme protein by weight of the composition, e.g. at a level of from 0.001% to 0.5% of enzyme protein by weight of the composition, appropriately at a level of from 0.01% to 0.2% of enzyme protein by weight of the composition.

Peroxidases/oxidases: Peroxidase enzymes are normally used in combination with hydrogen peroxide or a source thereof (e.g. a percarbonate, perborate or persulfate). Oxidase enzymes are used in combination with oxygen. Both types of enzymes are used for "solution bleaching", i.e. to prevent transfer of a textile dye from a dyed fabric to another fabric when said fabrics are washed together in a wash liquor, preferably together with an enhancing agent as described in e.g. WO 94/12621 and WO 95/01426. Suitable peroxidases/oxidases include those of plant, bacterial or fungal origin. Chemically or genetically modified mutants are included.

Peroxidase and/or oxidase enzymes are normally incorporated in the detergent composition at a level of from 0.00001% to 2% of enzyme protein by weight of the composition, such as at a level of from 0.0001% to 1% of enzyme protein by weight of the composition, e.g. at a level of from 0.001% to 0.5% of enzyme protein by weight of the composition, appropriately at a level of from 0.01% to 0.2% of enzyme protein by weight of the composition.

Mixtures of the above-mentioned enzymes may also be included in detergent compositions of the invention, e.g. a mixture of a protease, an amylase, a lipase and/or a cellulase.

The enzyme hybrid, or any other enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, such as at a level of from 0.001% to 0.5% of enzyme protein by weight of the composition, e.g. at a level of from 0.01% to 0.2% of enzyme protein by weight of the composition.

Bleaching agents: Additional optional detergent ingredients that can be included in the detergent compositions of the present invention include bleaching agents such as PB1, PB4 and percarbonate with a particle size of 400–800 microns. These bleaching agent components can include one or more oxygen bleaching agents and, depending upon the bleaching agent chosen, one or more bleach activators. When present oxygen bleaching compounds will typically be present at levels of from about 1% to about 25%. In general, bleaching compounds are optional added components in non-liquid formulations, e.g. granular detergents.

A bleaching agent component for use herein can be any of the bleaching agents useful for detergent compositions including oxygen bleaches, as well as others known in the art.

A bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. No. 4,483,781, U.S. Pat. No. 740,446, EP 0 133 354 and U.S. Pat. No. 4,412,934. Highly preferred bleaching agents also include 6-nonylamino-6-oxoperoxycaproic acid as described in U.S. Pat. No. 4,634,551.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

The hydrogen peroxide releasing agents can be used in combination with bleach activators such as tetraacetylethylenediamine (TAED), nonanoyloxybenzenesulfonate (NOBS, described in U.S. Pat. No. 4,412,934), 3,5-trimethyl-hexsanoloxybenzenesulfonate (ISONOBS, described in EP 120 591) or pentaacetylglucose (PAG), which are perhydrolyzed to form a peracid as the active bleaching species, leading to improved bleaching effect. In addition, very suitable are the bleach activators C8(6-octanamido-caproyl) oxybenzene-sulfonate, C9(6-nonanamido caproyl) oxybenzenesulfonate and C10 (6-decanamido caproyl) oxybenzenesulfonate or mixtures thereof. Also suitable activators are acylated citrate esters such as disclosed in European Patent Application No. 91870207.7.

Useful bleaching agents, including peroxyacids and bleaching systems comprising bleach activators and peroxygen bleaching compounds for use in cleaning compositions according to the invention are described in application U.S. Ser. No. 08/136,626.

The hydrogen peroxide may also be present by adding an enzymatic system (i.e. an enzyme and a substrate therefore) which is capable of generation of hydrogen peroxide at the beginning or during the washing and/or rinsing process. Such enzymatic systems are disclosed in European Patent Application EP 0 537 381.

Bleaching agents other than oxygen bleaching agents are also known in the art and can be utilized herein. One type of non-oxygen bleaching agent of particular interest includes photoactivated bleaching agents such as the sulfonated zinc and/or aluminium phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent composition will contain about 0.025% to about 1.25%, by weight, of sulfonated zinc phthalocyanine.

Bleaching agents may also comprise a manganese catalyst. The manganese catalyst may, e.g., be one of the compounds described in "Efficient manganese catalysts for low-temperature bleaching", *Nature* 369, 1994, pp. 637–639.

Suds suppressors: Another optional ingredient is a suds suppressor, exemplified by silicones, and silica-silicone mixtures. Silicones can generally be represented by alkylated polysiloxane materials, while silica is normally used in finely divided forms exemplified by silica aerogels and xerogels and hydrophobic silicas of various types. Theses materials can be incorporated as particulates, in which the suds suppressor is advantageously releasably incorporated in a water-soluble or water-dispersible, substantially non surface-active detergent impermeable carrier. Alternatively the suds suppressor can be dissolved or dispersed in a liquid carrier and applied by spraying on to one or more of the other components.

A preferred silicone suds controlling agent is disclosed in U.S. Pat. No. 3,933,672. Other particularly useful suds suppressors are the self-emulsifying silicone suds suppressors, described in German Patent Application DTOS 2,646,126. An example of such a compound is DC-544, commercially available form Dow Corning, which is a siloxane-glycol copolymer. Especially preferred suds controlling agent are the suds suppressor system comprising a mixture of silicone oils and 2-alkyl-alkanols. Suitable 2-alkyl-alkanols are 2-butyl-octanol which are commercially available under the trade name Isofol 12 R.

Such suds suppressor system are described in European Patent Application EP 0 593 841.

Especially preferred silicone suds controlling agents are described in European Patent Application No. 92201649.8. Said compositions can comprise a silicone/ silica mixture in combination with fumed nonporous silica such as Aerosil$^R$.

The suds suppressors described above are normally employed at levels of from 0.001% to 2% by weight of the composition, preferably from 0.01% to 1% by weight.

Other components: Other components used in detergent compositions may be employed, such as soil-suspending agents, soil-releasing agents, optical brighteners, abrasives, bactericides, tarnish inhibitors, coloring agents, and/or encapsulated or nonencapsulated perfumes.

Especially suitable encapsulating materials are water soluble capsules which consist of a matrix of polysaccharide and polyhydroxy compounds such as described in GB 1,464,616.

Other suitable water soluble encapsulating materials comprise dextrins derived from ungelatinized starch acid esters of substituted dicarboxylic acids such as described in U.S. Pat. No. 3,455,838. These acid-ester dextrins are, preferably, prepared from such starches as waxy maize, waxy sorghum, sago, tapioca and potato. Suitable examples of said encapsulation materials include N-Lok manufactured by National Starch. The N-Lok encapsulating material consists of a modified maize starch and glucose. The starch is modified by adding monofunctional substituted groups such as octenyl succinic acid anhydride.

Antiredeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably form 0.75% to 8%, most preferably from 1% to 6% by weight of the composition.

Preferred optical brighteners are anionic in character, examples of which are disodium 4,4'-bis-(2-diethanolamino-4-anilino -s- triazin-6-ylamino)stilbene-2:2'-disulphonate, disodium 4,-4'-bis-(2-morpholino-4-anilino-s-triazin-6-ylamino-stilbene-2:2'-disulphonate, disodium 4,4'-bis-(2,4-dianilino-s-triazin-6-ylamino)stilbene-2:2'-disulphonate, monosodium 4',4"-bis-(2,4-dianilino-s-tri-azin-6-ylamino) stilbene-2-sulphonate, disodium 4,4'-bis-(2-anilino-4-(N-methyl-N- 2-hydroxyethylamino)-s-triazin-6-ylamino) stilbene-2,2'-disulphonate, disodium 4,4'-bis-(4-phenyl-2,1, 3-triazol-2-yl)-stilbene-2,2'disulphonate, disodium 4,4'bis (2-anilino-4-(1-methyl-2-hydroxyethylamino)-s-triazin-6-ylami-no)stilbene-2,2'disulphonate, sodium 2(stilbyl-4"-(naphtho-1',2':4,5)-1,2, 3,-triazole-2"-sulphonate and 4,4'-bis(2-sulphostyryl)biphenyl.

Other useful polymeric materials are the polyethylene glycols, particularly those of molecular weight 1000–10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in U.S. Pat. No. 4,116,885 and 4,711,730 and EP 0 272 033. A particular preferred polymer in accordance with EP 0 272 033 has the formula:

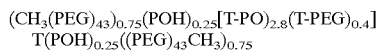

where PEG is —(OC$_2$H$_4$)0-, PO is (OC$_3$H$_6$O) and T is (pOOC$_6$H$_4$CO).

Also very useful are modified polyesters as random copolymers of dimethyl terephthalate, dimethyl sulfoisophthalate, ethylene glycol and 1,2-propanediol, the end groups consisting primarily of sulphobenzoate and secondarily of mono esters of ethylene glycol and/or 1,2-propanediol. The target is to obtain a polymer capped at both end by sulphobenzoate groups, "primarily", in the present context most of said copolymers herein will be endcapped by sulphobenzoate groups. However, some copolymers will be less than fully capped, and therefore their end groups may consist of monoester of ethylene glycol and/or 1,2-propanediol, thereof consist "secondarily" of such species.

The selected polyesters herein contain about 46% by weight of dimethyl terephthalic acid, about 16% by weight of 1,2-propanediol, about 10% by weight ethylene glycol, about 13% by weight of dimethyl sulfobenzoic acid and about 15% by weight of sulfoisophthalic acid, and have a molecular weight of about 3.000. The polyesters and their method of preparation are described in detail in EP 311 342.

Softening agents: Fabric softening agents can also be incorporated into laundry detergent compositions in accordance with the present invention. These agents may be inorganic or organic in type. Inorganic softening agents are exemplified by the smectite clays disclosed in GB-A-1 400898 and in U.S. Pat. No. 5,019,292. Organic fabric softening agents include the water insoluble tertiary amines as disclosed in GB-A1 514 276 and EP 0 011 340 and their combination with mono C$_2$–C$_{14}$ quaternary ammonium salts are disclosed in EP-B-0 026 528 and di-long-chain amides as disclosed in EP 0 242 919. Other useful organic ingredients of fabric softening systems include high molecular weight polyethylene oxide materials as disclosed in EP 0 299 575 and 0 313 146.

Levels of smectite clay are normally in the range from 5% to 15%, more preferably from 8% to 12% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Polymeric dye-transfer inhibiting agents: The detergent compositions according to the present invention may also comprise from 0.001% to 10%, preferably from 0.01% to 2%, more preferably form 0.05% to 1% by weight of polymeric dye- transfer inhibiting agents. Said polymeric dye-transfer inhibiting agents are normally incorporated into detergent compositions in order to inhibit the transfer of dyes from colored fabrics onto fabrics washed therewith. These polymers have the ability of complexing or adsorbing the fugitive dyes washed out of dyed fabrics before the dyes have the opportunity to become attached to other articles in the wash.

Especially suitable polymeric dye-transfer inhibiting agents are polyamine N-oxide polymers, copolymers of N-vinyl-pyrrolidone and N-vinylimidazole, polyvinylpyrrolidone polymers, polyvinyloxazolidones and polyvinylimidazoles or mixtures thereof.

Addition of such polymers also enhances the performance of the enzymes according the invention.

The detergent composition according to the invention can be in the form of a liquid, paste, gel, bar or granulate (i.e. in granular form).

Non-dusting granulates may be produced, e.g., as disclosed in U.S. Pat. No. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

Granular compositions according to the present invention can also be in "compact form", i.e. they may have a relatively higher density than conventional granular detergents, i.e. form 550 to 950 g/l; in such case, the granular detergent compositions according to the present invention will contain a lower amount of "Inorganic filler salt", compared to conventional granular detergents; typical filler salts are alkaline earth metal salts of sulphates and chlorides, typically sodium sulphate; "Compact" detergent typically comprise not more than 10% filler salt. The liquid compositions according to the present invention can also be in "concentrated form", in such case, the liquid detergent compositions according to the present invention will contain a lower amount of water, compared to conventional liquid detergents. Typically, the water content of the concentrated liquid detergent is less than 30%, more preferably less than 20%, most preferably less than 10% by weight of the detergent compositions.

The compositions of the invention may, for example, be formulated as hand and machine laundry detergent compositions including laundry additive compositions and compositions suitable for use in the pretreatment of stained fabrics.

The following examples are intended to exemplify compositions within the scope of the present invention, but are not intended to limit or otherwise define the scope of the invention. In the detergent compositions, the abbreviated component identifications have the following meanings:

LAS: Sodium linear $C_{12}$ alkyl benzene sulphonate
TAS: Sodium tallow alkyl sulphate
XYAS: Sodium $C_{1X}$–$C_{1Y}$ alkyl sulfate
SS: Secondary soap surfactant of formula 2-butyl octanoic acid
25EY: A $C_{12}$–$C_{15}$ predominantly linear primary alcohol condensed with an average of Y moles of ethylene oxide
45EY: A $C_{14}$–$C_5$ predominantly linear primary alcohol condensed with an average of Y moles of ethylene oxide
XYEZS: $C_{1X}$–$C_{1Y}$ sodium alkyl sulfate condensed with an average of Z moles of ethylene oxide per mole
Nonionic: $C_{13}$–$C_{15}$ mixed ethoxylated/propoxylated fatty alcohol with an average degree of ethoxylation of 3.8 and an average degree of propoxylation of 4.5 sold under the tradename Plurafax LF404 by BASF Gmbh
CFAA: $C_{12}$–$C_{14}$ alkyl N-methyl glucamide
TFAA: $C_{16}$–$C_{18}$ alkyl N-methyl glucamide
Silicate: Amorphous Sodium Silicate ($SiO_2$:$Na_2O$ ratio=2.0)
NaSKS-6: Crystalline layered silicate of formula $\delta$-$Na_2Si_2O_5$
Carbonate: Anhydrous sodium carbonate
Phosphate: Sodium tripolyphosphate
MA/AA: Copolymer of 1:4 maleic/acrylic acid, average molecular weight about 80,000
Polyacrylate: Polyacrylate homopolymer with an average molecular weight of 8,000 sold under the tradename PA30 by BASF Gmbh
Zeolite A: Hydrated Sodium Aluminosilicate of formula $Na_{12}(AlO_2SiO_2)_{12}.27H_2O$ having a primary particle size in the range from 1 to 10 micrometers
Citrate: Tri-sodium citrate dihydrate
Citric: Citric Acid
Perborate: Anhydrous sodium perborate monohydrate bleach, empirical formula $NaBO_2.H_2O_2$
PB4: Anhydrous sodium perborate tetrahydrate
Percarbonate: Anhydrous sodium percarbonate bleach of empirical formula $2Na_2CO_3.3H_2O_2$
TAED: Tetraacetyl ethylene diamine
CMC: Sodium carboxymethyl cellulose
DETPMP: Diethylene triamine penta (methylene phosphonic acid), marketed by Monsanto under the Tradename Dequest 2060
PVP: Polyvinylpyrrolidone polymer
EDDS: Ethylenediamine-N,N'-disuccinic acid, [S,S] isomer in the form of the sodium salt
Suds 25% paraffin wax Mpt 50° C., 17% hydrophobic silica, 58%
Suppressor: paraffin oil
Granular Suds 12% Silicone/silica, 18% stearyl alcohol, 70%
suppressor: starch in granular form
Sulphate: Anhydrous sodium sulphate
HMWPEO: High molecular weight polyethylene oxide
TAE 25: Tallow alcohol ethoxylate (25)

In the following compositions, "Enzyme" refers to enzyme hybrid(s) and any added enzyme(s):

Detergent Example I

A granular fabric cleaning composition in accordance with the invention may be prepared as follows:

| | |
|---|---|
| Sodium linear $C_{12}$ alkyl benzene sulfonate | 6.5 |
| Sodium sulfate | 15.0 |
| Zeolite A | 26.0 |
| Sodium nitrilotriacetate | 5.0 |
| Enzyme | 0.1 |
| PVP | 0.5 |
| TAED | 3.0 |
| Boric acid | 4.0 |
| Perborate | 18.0 |
| Phenol sulphonate | 0.1 |
| Minors | Up to 100 |

Detergent Example II

A compact granular fabric cleaning composition (density 800 g/l) in accord with the invention may be prepared as follows:

| | |
|---|---|
| 45AS | 8.0 |
| 25E3S | 2.0 |
| 25E5 | 3.0 |
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |

-continued

| | |
|---|---|
| Enzyme | 0.1 |
| TAED | 6.0 |
| Percarbonate | 22.0 |
| EDDS | 0.3 |
| Granular suds suppressor | 3.5 |
| water/minors | Up to 100% |

Detergent Example III

Granular fabric cleaning compositions in accordance with the invention which are useful in the laundering of coloured fabrics may be prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10 |
| Citric acid | 2.5 | 3.0 |
| Zeolite A | 32.1 | 25.0 |
| Na-SKS-6 | — | 9.0 |
| MA/AA | 5.0 | 5.0 |
| DETPMP | 0.2 | 0.8 |
| Enzyme | 0.10 | 0.05 |
| Silicate | 2.5 | — |
| Sulphate | 5.2 | 3.0 |
| PVP | 0.5 | — |
| Poly (4-vinylpyridine)-N-Oxide/copolymer of vinyl-imidazole and vinyl-pyrrolidone | — | 0.2 |
| Perborate | 1.0 | — |
| Phenol sulfonate | 0.2 | — |
| Water/Minors | Up to 100% | |

Detergent Example IV

Granular fabric cleaning compositions in accordance with the invention which provide "Softening through the wash" capability may be prepared as follows:

| | | |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

Detergent Example V

Heavy duty liquid fabric cleaning compositions in accordance with the invention may be prepared as follows:

| | I | II |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme | 0.10 | 0.05 |
| Coco-alkyl dimethyl hydroxy ethyl ammonium chloride | — | 3.0 |
| Smectite clay | — | 5.0 |
| PVP | 2.0 | — |
| Water/Minors | Up to 100% | |

The enzyme hybrid may be incorporated in concentrations conventionally employed in detergents. It is at present contemplated that, in the detergent composition of the invention, the enzyme hybrid may suitably be added in an amount corresponding to 0.00001–1 mg (calculated as pure enzymatic protein) of enzyme hybrid per liter of wash liquor.

Reaction time

The reaction time for removing or bleaching the soiling or stain(s) from fabric may vary; the fabric may be soaked for one or two days, or the washing may be performed within a shorter period, typically machine-washed for a period of 1 to 90 minutes, preferably for a period of 1 to 30 minutes.

A further aspect of the invention relates to a DNA construct disclosed herein which encodes, or which comprises a sequence which encodes, an enzyme hybrid as disclosed in the present specification.

A still further aspect of the invention relates to a polypeptide (fusion protein or enzyme hybrid) which is encoded by such a DNA construct or sequence, and/or which is disclosed in the present specification. Thus, the invention encompasses an enzyme hybrid encoded by a hybrid-encoding DNA sequence comprised within the DNA sequences of SEQ ID No.1, SEQ ID No.3, SEQ ID No.5, SEQ ID No.7, SEQ ID No.9, SEQ ID No.10, SEQ ID No. 11, SEQ ID No. 12, SEQ ID No. 13, SEQ ID No. 14, SEQ ID No. 15, SEQ ID No. 16, SEQ ID No. 17, SEQ ID No. 18 or SEQ ID No. 19, or an enzyme hybrid having an amino acid sequence comprised within the amino acid sequences of SEQ ID No. 2, SEQ ID No. 4, SEQ ID No. 6 or SEQ ID No. 8.

The invention is further illustrated in the following example, which are not intended to be in any way limiting to the scope of the invention as claimed.

MATERIALS AND METHODS

Strains:

*Bacillus agaradherens* NCIMB No. 40482: comprises the endoglucanase enzyme encoding DNA sequence of Example 2, below.

*Escherichia coli* SJ2 [Diderichsen et al., *J. Bacteriol.* 172 (1990), pp. 4315–4321].

Electrocompetent cells prepared and transformed using a Bio-Rad GenePulser™ as recommended by the manufacturer.

*Bacillus subtilis* PL2306: this strain is the *B. subtilis* DN1885 with disrupted apr and npr genes [Diderichsen et al., *J. Bacteriol.* 172 (1990), pp. 4315–4321] disrupted in the transcriptional unit of the known *Bacillus subtilis* cellulase gene, resulting in cellulase-negative cells. The disruption was performed essentially as described in Sonenshein et al. (Eds.), *Bacillus subtilis and other Gram-Positive Bacteria*, American Society for Microbiology (1993), p.618.
Plasmids:

pDN1528 [Jorgensen et al., *J. Bacteriol.* 173 (1991), p.559–567].

pBluescriptKSII- (Stratagene, USA).

pDN1981 [Jorgensen et al., Gene 96 (1990), p. 37–41].
Solutions/Media

TY and LB agar [as described in Ausubel et al. (Eds.), *Current Protocols in Molecular Biology*, John Wiley and Sons (1995)].

SB: 32 g Tryptone, 20 g yeast extract, 5 g sodium chloride and 5 ml 1 N sodium hydroxide are mixed in sterile water to a final volume of 1 litre. The solution is sterilised by autoclaving for 20 minutes at 121° C.

10% Avicel™: 100 g of Avicel™ (FLUKA, Switzerland) is mixed with sterile water to a final volume of 1 litre, and the resulting 10% Avicel™ is sterilised by autoclaving for 20 minutes at 121° C.

Buffer: 0.05 M potassium phosphate, pH 7.5.
General molecular biology methods

DNA manipulations and transformations were performed using standard methods of molecular biology [Sambrook et al., *Molecular Cloning: A Laboratory Manual*, Cold Spring Harbor lab., Cold Spring Harbor, N.Y. (1989); Ausubel et al. (Eds.), *Current Protocols in Molecular Biology*, John Wiley and Sons (1995); C. R. Harwood and S. M. Cutting (Eds.) *Molecular Biological Methods for Bacillus*, John Wiley and Sons (1990)].

Enzymes for DNA manipulations were used according to the specifications of the suppliers.

EXAMPLE 1

Subcloning of a partial Termamyl sequence.

The alpha-amylase gene encoded on pDN1528 was PCR amplified for introduction of a BamHI site in the 3'-end of the coding region. The PCR and the cloning were carried out as follows:

Approximately 10–20 ng of plasmid pDN 1528 was PCR amplified in HiFidelity™ PCR buffer (Boehringer Mannheim, Germany) supplemented with 200 µM of each dNTP, 2.6 units of HiFidelity™ Expand enzyme mix, and 300 pmol of each primer:

```
#5289

5'-GCT TTA CGC CCG ATT GCT GAC GCT G -3'                                            (SEQ ID No. 20)

#26748

5'-GCG ATG AGA CGC GCG GCC GCC TAT CTT TGA ACA TAA ATT GAA ACG GAT CCG -3'   (SEQ ID No. 21)

(BamHI restriction site underlined].
```

The PCR reactions were performed using a DNA thermal cycler (Landgraf, Germany). One incubation at 94° C. for 2 min, 60° C. for 30 sec and 72° C. for 45 sec was followed by ten cycles of PCR performed using a cycle profile of denaturation at 94° C. for 30 sec, annealing at 60° C. for 30 sec, and extension at 72° C. for 45 sec and twenty cycles of denaturation at 94° C. for 30 sec, 60° C. for 30 sec and 72° C. for 45 sec (at this elongation step, 20 sec are added every cycle). 10 µl aliquots of amplification product were analyzed by electrophoresis in 1.0% agarose gels (NuSieve™, FMC) with ReadyLoad™ 100 bp DNA ladder (GibcoBRL, Denmark) as a size marker.

40 µl aliquots of PCR product generated as described above were purified using QIAquick™ PCR purification kit (Qiagen, USA) according to the manufacturer's instructions. The purified DNA was eluted in 50 µl of 10 mM Tris-HCl, pH 8.5. 25 µl of the purified PCR fragment was digested with BamHI and PstI, subjected to electrophoresis in 1.0% low gelling temperature agarose (SeaPlaque™ GTG, FMC) gels, and the relevant fragment was excised from the gel and purified using QIAquick™ Gel extraction Kit (Qiagen, USA) according to the manufacturer's instructions. The isolated DNA fragment was then ligated to BamHI-PstI digested pBluescriptll KS-, and the ligation mixture was used to transform *E. coli* SJ2.

Cells were plated on LB agar plates containing Ampicillin (200 µg/ml) and supplemented with X-gal (5-bromo-4-chloro-3-indolyl-α-D-galactopyranoside, 50 µg/ml), and incubated at 37° C. overnight. The next day, white colonies were restreaked onto fresh LB-Ampicillin agar plates and incubated at 37° C. overnight. The following day, single colonies were transferred to liquid LB medium containing Ampicillin (200 µg/ml) and incubated overnight at 37° C. with shaking at 250 rpm.

Plasmids were extracted from the liquid cultures using QIAgen Plasmid Purification mini kit (Qiagen, USA) according to the manufacturer's instructions. 5 µl samples of the plasmids were digested with PstI and BamHI. The digestions were checked by gel electrophoresis on a 1.0% agarose gel (NuSieve™, FMC). One positive clone, containing the PstI-BamHI fragment containing part of the α-amylase gene, was designated pMB335. This plasmid was then used in the construction of α-amylase-CBD hybrid.
Isolation of genomic DNA

*Clostridium stercorarium* NCIMB 11754 was grown anaerobically at 60° C. in specified media as recommended by The National Collections of Industrial and Marine Bacteria Ltd. (NCIMB), Scotland. Cells were harvested by centrifugation.

Genomic DNA was isolated as described by Pitcher et al, *Lett. Appl. Microbiol.* 8 (1989), pp. 151–156.

In vitro amplification of the CBD-dimer of *Clostridium stercorarium* (NCIMB 11754) XynA Approximately 100–200 ng of genomic DNA was PCR amplified in HiFidelity™ PCR buffer (Boehringer Mannheim, Germany) supplemented with 200 µM of each dNTP, 2.6 units of HiFidelity™ Expand enzyme mix, and 300 pmol of each primer:

```
#27183

5'-GCT GCA GGA TCC GTT TCA ATT TAT GTT CAA AGA TCT GGC GGA CCT GGA ACG CCA AAT    (SEQ ID No. 22)
```

-continued

AAT GGA AGA GG -3'

27182

5'-GCA CTA GCT AGA <u>CGG CCG</u> CTA CCA GTC AAC ATT AAC AGG ACC TGA G -3'  (SEQ ID No. 23)

(BamHI and EagI restriction sites underlined).

The primers were designed to amplify the DNA encoding the cellulose-binding domain of the XynA-encoding gene of *Clostridium stercorarium* NCIMB 11754; the DNA sequence was extracted from the database GenBank under the accession number D13325.

The PCR reactions were performed using a DNA thermal cycler (Landgraf, Germany). One incubation at 94° C. for 2 min, 60° C. for 30 sec and 72° C. for 45 sec was followed by ten cycles of PCR performed using a cycle profile of denaturation at 94° C. for 30 sec, annealing at 60° C. for 30 sec, and extension at 72° C. for 45 sec and twenty cycles of denaturation at 94° C. for 30 sec, 60° C. for 30 sec and 72° C. for 45 sec (at this elongation step, 20 sec are added every cycle). 10 μl aliquots of amplification product were analyzed by electrophoresis in 1.0% agarose gels (NuSieve™, FMC) with ReadyLoad™ 100 bp DNA ladder (GibcoBRL, Denmark) as a size marker.

Cloning by polymerase chain reaction (PCR):

Subcloning of PCR fragments.

40 μl aliquots of PCR product generated as described above were purified using QIAquick™ PCR purification kit (Qiagen, USA) according to the manufacturer's instructions. The purified DNA was eluted in 50 μl of 10 mM Tris-HCl, pH 8.5. 25 μl of the purified PCR fragment was digested with BamHI and EagI, subjected to electrophoresis in 1.0% low gelling temperature agarose (SeaPlaque™ GTG, FMC) gels, and the relevant fragment was excised from the gels and purified using QIAquick™ Gel extraction Kit (Qiagen, USA) according to the manufacturer's instructions. The isolated DNA fragment was then ligated to BamHI-NotI digested pMB335 and the ligation mixture was used to transform *E. coli* SJ2.

Identification and characterization of positive clones

Cells were plated on LB agar plates containing Ampicillin (200 μg/ml) and incubated at 37° C. overnight. The next day, colonies were restreaked onto fresh LB-Ampicillin agar plates and incubated at 37° C. overnight. The following day, single colonies were transferred to liquid LB medium containing Ampicillin (200 μg/ml) and incubated overnight at 37° C. with shaking at 250 rpm.

Plasmids were extracted from the liquid cultures using QIAgen Plasmid Purification mini kit (Qiagen, USA) according to the manufacturer's instructions. 5 μl samples of the plasmids were digested with BamHI and NotII. The digestions were checked by gel electrophoresis on a 1.0% agarose gel (NuSieve™, FMC). The appearance of a DNA fragment of the same size as seen from the PCR amplification indicated a positive clone.

One positive clone, containing the fusion construct of the α-amylase gene and the CBD-dimer of *Clostridium stercorarium* (NCIMB 11754) XynA, was designated MBamyX.

Cloning of the fusion construct into a Bacillus-based expression vector

The pDN1528 vector contains the amyL gene of *B. licheniformis*; this gene is actively expressed in *B. subtilis*, resulting in the production of active α-amylase appearing in the supernatant. For expression purposes, the DNA encoding the fusion protein as constructed above was introduced to pDN1528.

This was done by digesting pMBamyX and pDN1528 with SalI-NotI, purifying the fragments and ligating the 4.7 kb pDN1528 SalI-NotI fragment with the 1.0 kb pMBamyX SalI-NotI fragment. This created an inframe fusion of the hybrid construction with the Termamyl™ (*B. licheniformis* α-amylase) gene. The DNA sequence of the fusion construction of pMB206, and the corresponding amino acid sequence, are shown in SEQ ID No. 1 and SEQ ID No. 2, respectively.

The ligation mixture was used to transform competent cells of *B. subtilis* PL2306. Cells were plated on LB agar plates containing chloramphenicol (6 μg/ml), 0.4% glucose and 10 mM potassium hydrogen phosphate, and incubated at 37° C. overnight. The next day, colonies were restreaked onto fresh LBPG (LB plates with 0.4% glucose and 10 mM potassium phosphate, pH 10) chloramphenicol agar plates and incubated at 37° C. overnight. The following day, single colonies of each clone were transferred to liquid LB medium containing chloramphenicol (6 μg/ml) and incubated overnight at 37° C. with shaking at 250 rpm.

Plasmids were extracted from the liquid cultures using QIAgen Plasmid Purification mini kit (Qiagen, USA) according to the manufacturer's instructions. However, the resuspension buffer was supplemented with 1 mg/ml of chicken egg white lysozyme (SIGMA, USA) prior to lysing the cells at 37° C. for 15 minutes. 5 μl samples of the plasmids were digested with BamHI and NotI. The digestions were checked by gel electrophoresis on a 1.5% agarose gel (NuSieve™, FMC). The appearance of a DNA fragment of the same size as seen from the PCR amplification indicated a positive clone. One positive clone was designated MB-BSamyx.

Expression, secretion and functional analysis of the fusion protein

The clone MB-BSamyx (expressing Termamyl™ fused to *C. stercorarium* XynA dimer CBD) was incubated for 20 hours in SB medium at 37° C. with shaking at 250 rpm. 1 ml of cell-free supernatant was mixed with 200 μl of 10% Avicel™. The mixture was incubated for 1 hour at 0° C. and then centrifuged for 5 minutes at 5000× g. The pellet was resuspended in 100 μl of SDS-PAGE buffer, and the suspension was boiled at 95° C. for 5 minutes, centrifuged at 5000× g for 5 minutes, and 25 μl was loaded onto a 4–20% Laemmli Tris-Glycine, SDS-PAGE NOVEX™ gel (Novex, USA). The samples were subjected to electrophoresis in an Xcell™ Mini-Cell (NOVEX, USA) as recommended by the manufacturer. All subsequent handling of gels, including staining (Coomassie), destaining and drying, were performed as described by the manufacturer.

The appearance of a protein band of molecular weight approx. 85 kDa indicated expression in *B. subtilis* of the Termamyl-CBD fusion amyx.

EXAMPLE 2

Identification of a novel CBD representing a new CBD family

The alkaline cellulase cloned in *Bacillus subtilis* as described below was expressed by incubating the clone for 20 hours in SB medium at 37° C. with shaking at 250 rpm.

The expressed cellulase was shown to contain a CBD by its ability to specifically bind to Avicel™.

When left to incubate for a further 20 hours, the cellulase was proteolytically cleaved and two specific protein bands appeared in SDS-PAGE, one corresponding to the catalytic part of the cellulase, approximate molecular weight (MW) 35 kD, and the other corresponding to a proposed linker and CBD of approximate MW 8 kD.

The CBD was found to be the C-terminal part of the cellulase, and did not match any of the CBD families described previously [Tomme et al., *Cellulose-Binding Domains: Classification and Properties*, In: J. N. Saddler and M. H. Penner (Eds.), *Enzymatic Degradation of Insoluble Carbohydrates*, ACS Symposium Series No. 618 (1996)]. Accordingly, this CBD appears to be the first member of a new family.

Cloning of the alkaline cellulase (endoglucanase) from *Bacillus agaradherens* and expression of the alkaline cellulase in *Bacillus subtilis*

The nucleotide sequence encoding the alkaline cellulase from *Bacillus agaradherens* (deposited under accession No. NCIMB 40482) was cloned by PCR for introduction in an expression plasmid pDN1981. PCR was performed essentially as described above on 500 ng of genomic DNA, using the following two primers containing NdeI and KpnI restriction sites for introducing the endoglucanase-encoding DNA sequence to pDN1981 for expression:

hours. Endoglucanase-positive colonies were identified as colonies surrounded by a blue halo.

Each of the positive transformants was inoculated in 10 ml TY medium containing Kanamycin (10 mg/ml). After 1 day of incubation at 37° C. with shaking at 250 rpm, 50 ml of supernatant was removed. The endoglucanase activity was identified by adding 50 ml of supernatant to holes punctured in the agar of LB agar plates containing 0.1% AZCL HE-cellulose.

After 16 hours incubation at 37° C., blue halos surrounding holes indicated expression of the endoglucanase in *B. subtilis*. One such clone was designated MB208. The encoding DNA sequence and amino acid sequence of the endoglucanase are shown in SEQ ID No. 3 and SEQ ID No. 4, respectively.

The DNA sequence was determined as follows: Qiagen purified plasmid DNA was sequenced with the Taq deoxy terminal cycle sequencing kit (Perkin Elmer, USA) using the primers #21318 and #20887 (vide supra) and employing an Applied Biosystems 373A automated sequencer operated according to the manufacturer's instructions. Analysis of the sequence data is performed according to Devereux et al.,

```
#20887

5'-GTA GGC TCA GTC ATA TGT TAC ACA TTG AAA GGG GAG GAG AAT CAT GAA AAA GAT AAC     (SEQ ID No. 24)

TAC TAT TTT TGT CG-3'

#21318

5'-GTA CCT CGC GGG TAC CAA GCG GCC GCT TAA TTG AGT GGT TCC CAC GGA CCG-3'          (SEQ ID No. 25)
```

After PCR cycling, the PCR fragment was purified using QIAquick™ PCR column kit (Qiagen, USA) according to the manufacturer's instructions. The purified DNA was eluted in 50 μl of 10 mM Tris-HCl, pH 8.5, digested with NdeI and KpnI, purified and ligated to digested pDN1981. The ligation mixture was used to transform *B. subtilis* PL2306. Competent cells were prepared and transformed as described by Yasbin et al., *J. Bacteriol.* 121 (1975), pp. 296–304.

*Carcinogenesis* 14 (1993), pp. 795–801.

In vitro amplification of the CBD of *Bacillus agaradherens* NCIMB 40482 endoglucanase Approximately 10–20 ng of plasmid pMB208 was PCR amplified in HiFidelity™ PCR buffer (Boehringer Mannheim, Germany) supplemented with 200 μM of each dNTP, 2.6 units of HiFidelity™ Expand enzyme mix and 300 pmol of each primer:

```
#27184

5'-GCT GCA GGA TCC GTT TCA ATT TAT GTT CAA AGA TCT CCT GGA GAG TAT CCA GCA TGG     (SEQ ID No. 26)

GAC CCA A-3'

#28495

5'-GC ACA AGC TTG CGG CCG CTA ATT GAG TGG TTC CCA CGG ACC G -3'                    (SEQ ID No. 27)

(BamHI and NotI restriction sites underlined).
```

Isolation and testing of *B. subtilis* transformants

The transformed cells were plated on LB agar plates containing Kanamycin (10 mg/ml), 0.4% glucose, 10 mM potassium phosphate and 0.1% AZCL HE-cellulose (Megazyme, Australia), and incubated at 37° C. for 18

The primers were designed to amplify the CBD-encoding DNA of the cellulase-encoding gene of *Bacillus agaradherens* NCIMB 40482.

The PCR reaction was performed using a DNA thermal cycler (Landgraf, Germany). One incubation at 94° C. for 2 min, 60° C. for 30 sec and 72° C. for 45 sec was followed by ten cycles of PCR performed using a cycle profile of denaturation at 94° C. for 30 sec, annealing at 60° C. for 30 sec, and extension at 72° C. for 45 sec and twenty cycles of denaturation at 94° C. for 30 sec, 60° C. for 30 sec and 72° C. for 45 sec (at this elongation step, 20 sec are added every cycle). 10 μl aliquots of amplification product were analyzed by electrophoresis in 1.5% agarose gels (NuSieve™, FMC) with ReadyLoad™ 100 bp DNA ladder (GibcoBRL, Denmark) as a size marker.

Cloning by polymerase chain reaction (PCR):

Subcloning of PCR fragments

40 μl aliquots of PCR products generated as described above were purified using QIAquick™ PCR purification kit (Qiagen, USA) according to the manufacturer's instructions. The purified DNA was eluted in 50 μl of 10 mM Tris-HCl, pH 8.5. 25 μl of the purified PCR fragment was digested with BamHI and NotI, subjected to electrophoresis in 1.5% low gelling temperature agarose (SeaPlaque™ GTG, FMC) gels, and the relevant fragment was excised from the gels and purified using QIAquick™ Gel extraction kit (Qiagen, USA) according to the manufacturer's instructions. The isolated DNA fragment was then ligated to BamHI-NotI digested pMB335, and the ligation mixture was used to transform *E. coli* SJ2.

Identification and characterization of positive clones

Cells were plated on LB agar plates containing Ampicillin (200 μg/ml) and incubated at 37° C. overnight. The next day, colonies were restreaked onto fresh LB-Ampicillin agar plates and incubated at 37° C. overnight. The following day, single colonies were transferred to liquid LB medium containing Ampicillin (200 μg/ml) and incubated overnight at 37° C. with shaking at 250 rpm.

Plasmids were extracted from the liquid cultures using QIAgen Plasmid Purification mini kit (Qiagen, USA) according to the manufacturer's instructions. 5 μl samples of the plasmids were digested with BamHI and NotI. The digestions were checked by gel electrophoresis on a 1.5% agarose gel (NuSieve™, FMC). The appearance of a DNA fragment of the same size as seen from the PCR amplification indicated a positive clone.

One positive clone, containing the fusion construct of the Termamyl™ α-amylase gene and the CBD of *Bacillus agaradherens* NCIMB 40482 alkaline cellulase Cel5A, was designated MBamyC5A.

Cloning of the fusion construct into a Bacillus-based expression vector

As mentioned previously, the amyL gene of *B. licheniformis* (contained in the pDN1528 vector) is actively expressed in *B. subtilis*, resulting in the production of active α-amylase appearing in the supernatant. For expression purposes, the DNA encoding the fusion protein as constructed above was introduced to pDN1528. This was done by digesting pMBamyC5A and pDN1528 with SalI-NotI, purifying the fragments and ligating the 4.7 kb pDN1528 SalI-NotI fragment with the 0.5 kb pMBamyC5A SalI-NotI fragment. This created an inframe fusion of the hybrid construction with the Termamyl™ gene. The DNA sequence of the fusion construction of pMB378, and the corresponding amino acid sequence, are shown in SEQ ID No. 5 and SEQ ID No. 6, respectively.

The ligation mixture was used to transform competent cells of *B. subtilis* PL2306. Cells were plated on LB agar plates containing chloramphenicol (6 μg/ml), 0.4% glucose and 10 mM potassium hydrogen phosphate, and incubated at 37° C. overnight. The next day, colonies were restreaked onto fresh LBPG chloramphenicol agar plates and incubated at 37 ° C. overnight. The following day, single colonies of each clone were transferred to liquid LB medium containing chloramphenicol (6 μg/ml) and incubated overnight at 37° C. with shaking at 250 rpm.

Plasmids were extracted from the liquid cultures using QIAgen Plasmid Purification mini kit (Qiagen, USA) according to the manufacturer's instructions. However, the resuspension buffer was supplemented with 1 mg/ml of chicken egg white lysozyme (SIGMA, USA) prior to lysing the cells at 37° C. for 15 minutes. 5 μl samples of the plasmids were digested with BamHI and NotI. The digestions were checked by gel electrophoresis on a 1.5% agarose gel (NuSieve™, FMC). The appearance of a DNA fragment of the same size as seen from the PCR amplification indicated a positive clone. One positive clone was designated MB378.

Expression, secretion and functional analysis of the fusion protein

The clone MB378 (expressing Termamyl™ fused to *Bacillus agaradherens* Cel5A CBD) was incubated for 20 hours in SB medium at 37° C. with shaking at 250 rpm. 1 ml of cell-free supernatant was mixed with 200 μl of 10% Avicel™. The mixture was incubated for 1 hour at 0° C. and then centrifuged for 5 minutes at 5000× g. The pellet was resuspended in 100 μl of SDS-PAGE buffer, and the suspension was boiled at 95° C. for 5 minutes, centrifuged at 5000× g for 5 minutes, and 25 μl was loaded onto a 4–20% Laemmli Tris-Glycine, SDS-PAGE NOVEX™ gel (Novex, USA). The samples were subjected to electrophoresis in an Xcell™ Mini-Cell (NOVEX, USA) as recommended by the manufacturer. All subsequent handling of gels, including staining (Coomassie), destaining and drying, were performed as described by the manufacturer.

The appearance of a protein band of molecular weight approx. 60 kDa indicated expression in *B. subtilis* of the Termamyl™-CBD fusion encoded on the plasmid pMB378.

EXAMPLE 3

This example describes fusion of Termamyl™ and the CBD from *Cellulomonas fimi* (ATCC 484) cenA gene using the sequence overlap extension (SOE) procedure [see, e.g., Sambrook et al., Ausubel et al., or C. R. Harwood and S. M. Cutting (loc. cit.)]. The final construction is as follows: Termamyl™ promoter—Termamyl™ signal peptide—cenA CBD—linker—mature Termamyl™.

Amplification of the Termamyl™ fragment for SOE

Approximately 10–20 ng of plasmid pDN1528 was PCR amplified in HiFidelity™ PCR buffer (Boehringer Mannheim, Germany) supplemented with 200 μM of each dNTP, 2.6 units of HiFidelity™ Expand enzyme mix, and 100 pmol of each primer:

4576

5'-CTC GTC CCA ATC GGT TCC GTC -3'    (SEQ ID No. 28)

28403

5'-TGC ACT GGT ACA GTT CCT ACA ACT AGT CCT ACA CGT <u>GCA AAT CTT AAT GGG ACG</u>    (SEQ ID No. 29)

<u>CTG</u>-3'

The part of the primer #28403 constituting a fragment of the Termamyl™ sequence is underlined. The sequence on the 5' side of this underlined sequence is that coding for the linker region to the CBD.

The PCR reaction was performed using a DNA thermal cycler (Landgraf, Germany). One incubation at 94° C. for 2 min, 55° C. for 30 sec and 72° C. for 45 sec was followed by twenty cycles of PCR performed using a cycle profile of denaturation at 96° C. for 10 sec, annealing at 55° C. for 30 sec, and extension at 72° C. for 45 sec. 10 μl aliquots of the amplification product were analyzed by electrophoresis in 1.0% agarose gels (NuSieve™, FMC) with ReadyLoad™ 100 bp DNA ladder (GibcoBRL, Denmark) as a size marker.

40 μl aliquots of the PCR product generated as described above were purified using QIAquick™ PCR purification kit (Qiagen, USA) according to the manufacturer's instructions. The purified DNA was eluted in 50 μl of 10 mM Tris-HCl, pH 8.5.

Isolation of genomic DNA

*Cellulomonas fimi* ATCC 484 was grown in TY medium at 30° C. with shaking at 250 rpm for 24 hours. Cells were harvested by centrifugation.

Genomic DNA was isolated as described by Pitcher et al., *Lett. Appl. Microbiol.* 8 (1989), pp. 151–156.

In vitro amplification of the CBD of *Cellulomonas fimi* (ATCC 484) cenA gene for SOE procedure Approximately 100–200 ng of genomic DNA was PCR amplified in HiFidelity™ PCR buffer (Boehringer Mannheim, Germany) supplemented with 200 μM of each dNTP, 2.6 units of HiFidelity™ Expand enzyme mix, and 100 pmol of each primer:

SOE of the CBD from Cellulomonas fimi (ATCC 484) cenA gene and the Termamyl™ gene Approximately 100–200 ng of the PCR amplified Termamyl™ fragment and the PCR amplified cenA CBD fragment were used in a second round of PCR. SOE of the two fragments was performed in HiFidelity™ PCR buffer (Boehringer Mannheim, Germany) supplemented with 200 μM of each dNTP, 2.6 units of HiFidelity™ Expand enzyme mix.

A touch-down PCR cycling was performed as follows: One incubation at 96° C. for 2 min, 60° C. for 2 min and 72° C. for 45 sec. This cycle was repeated ten times with a 1° C. decrease of the annealing temperature at each cycle.

A third PCR reaction was started by adding 100 pmol of the two flanking primers #8828 and #4576 (vide supra) to amplify the hybrid DNA. PCR was performed by incubating the SOE reaction mixture at 96° C. for 2 min, 55° C. for 30 sec and 72° C. for 45 sec. This was followed by twenty cycles of PCR performed using a cycle profile of denaturation at 96° C. for 10 sec, annealing at 55° C. for 30 sec, and extension at 72° C. for 45 sec. 10 μl aliquots of the amplification product were analyzed by electrophoresis in 1.0% agarose gels (NuSieve™, FMC) with ReadyLoad™ 100 bp DNA ladder (GibcoBRL, Denmark) as a size marker. The SOE fragment had the expected size of 879 bp.

Subcloning of the SOE fragment coding for the CBD-Termamyl hybrid

40 μl of the SOE-PCR product generated as described above was purified using QIAquick™ PCR purification kit (Qiagen, USA) according to the manufacturer's instructions. The purified DNA was eluted in 50 μl of 10 mM Tris-HCl,

8828

5'-CTG CCT CAT <u>TCT GCA G</u>CA GCG GCG GCA AAT CTT AAT GCT CCC GGC TGC CGC GTC GAC    (SEQ ID No. 30)

TAC -3'

28404

5'-TGT AGG AAC TGT ACC AGT GCA CGT GGT GCC GTT GAG C -3'    (SEQ ID No. 31)

(PstI restriction site underlined).

The primers were designed to amplify the DNA encoding the cellulose-binding domain of the CenA-encoding gene of *Cellulomonas fimi* (ATCC 484). The DNA sequence was extracted from the database GenBank under the accession number M15823.

PCR cycling was performed as follows: One incubation at 94° C. for 2 min, 55° C. for 30 sec and 72° C. for 45 sec was followed by thirty cycles of PCR performed using a cycle profile of denaturation at 96° C. for 10 sec, annealing at 55° C. for 30 sec, and extension at 72° C. for 45 sec. 10 μl aliquots of the amplification product were analyzed by electrophoresis in 1.0% agarose gels (NuSieve™, FMC) with ReadyLoad™ 100 bp DNA ladder (GibcoBRL, Denmark) as a size marker.

40 μl aliquots of the PCR product generated as described above were purified using QIAquick™ PCR purification kit (Qiagen, USA) according to the manufacturer's instructions. The purified DNA was eluted in 50 μl of 10 mM Tris-HCl, pH 8.5.

pH 8.5. 25 μl of the purified PCR fragment was digested with PstI and KpnI, subjected to electrophoresis in 1.0% low gelling temperature agarose (SeaPlaque™ GTG, FMC) gels, and a fragment of 837 bp was excised from the gel and purified using QIAquick™ Gel extraction Kit (Qiagen, USA) according to the manufacturer's instructions. The isolated DNA fragment was then ligated to PstI- and KpnI-digested pDN1981, and the ligation mixture was used to transform competent cells of *B. subtilis* PL2306. Cells were plated on LB agar plates containing Kanamycin (10 μg/ml), 0.4% glucose and 10 mM potassium hydrogen phosphate, and incubated at 37° C. overnight. The next day, colonies were restreaked onto fresh LBPG Kanamycin agar plates and incubated at 37° C. overnight. The following day, single colonies of each clone were transferred to liquid LB medium containing Kanamycin (10 μg/ml) and incubated overnight at 37° C. with shaking at 250 rpm.

Plasmids were extracted from the liquid cultures using QIAgen Plasmid Purification mini kit (Qiagen, USA)

according to the manufacturer's instructions. However, the resuspension buffer was supplemented with 1 mg/ml of chicken egg white lysozyme (SIGMA, USA) prior to lysing the cells at 37° C. for 15 minutes. 5 μl samples of the plasmids were digested with PstI and KpnI. The digestions were checked by gel electrophoresis on a 1.5% agarose gel (NuSieve™, FMC). The appearance of a DNA fragment of 837 bp, the same size as seen from the PCR amplification, indicated a positive clone. One positive clone was designated MOL1297.

Expression, secretion and functional analysis of the fusion protein

The clone MOL1297 (expressing C. fimi cenA CBD fused to the N-terminal of TermamylT) was incubated for 20 hours in SB medium at 37° C. with shaking at 250 rpm. 1 ml of cell-free supernatant was mixed with 200 μl of 10% Avicel™. The mixture was incubated for 1 hour at 0° C. and then centrifuged for 5 min at 5000× g. The pellet was resuspended in 100 μl of SDS-PAGE buffer, boiled at 95° C. for 5 minutes, centrifuged at 5000× g for 5 minutes, and 25 μl was loaded on a 4–20% Laemmli Tris-Glycine, SDS-PAGE NOVEX gel (Novex, USA). The samples were subjected to electrophoresis in an Xcell™ Mini-Cell (NOVEX, USA) as recommended by the manufacturer. All subsequent handling of gels including staining (Coomassie), destaining and drying, was performed as described by the manufacturer.

The appearance of a protein band of MW approx. 85 kDa indicated expression in B. subtilis of the CBD-Termamyl™ fusion.

The encoding sequence for the C. fimi cenA CBD-Termamyl hybrid is shown in SEQ ID No. 7 (in which nucleotides 100–441 are the CBD-encoding part of the sequence). The corresponding amino acid sequence of the hybrid is shown in SEQ ID No. 8 (in which amino acid residues 30–147 are the CBD amino acid sequence).

19672

(SEQ ID No. 33)
5' CCACACTTCTCTTCCTTCCTC 3'

The PCR fragment was cut with BamHI and BalI, and cloned into pAHL which was also cut with BamHI and BalI just upstream of the presumed signal peptide processing site. The cloning was verified by sequencing (see SEQ ID No. 9).

Removing linker between CBD and lipase

This construct is made so that any linker of interest can be inserted between the CBD and the lipase in order to find an optimal linker.

An NheI site is introduced by the USE technique (Stratagene catalogue No. 200509) between the CBD and linker region in pIVI450, creating pIVI450+NheI site. pIVI450+NheI site is cut with XhoI and NheI, isolating the vector containing the CBD part.

The plasmid pIVI392 is cut with XhoI and NheI, and the fragment containing the Lipolase™ gene (minus signal peptide encoding sequence) is isolated.

The DNA fragments are ligated, generating pIVI450 CBD-NheI site-Lipolase™ containing an NheI site between the CBD and the lipase gene. In this NheI site different linkers can be introduced.

Introduction of non-glycosylated linker

The protein expressed from the construct described here contains a construction of the type: CBD-nonglycosylated linker-lipase.

The amino acid sequence of the linker is as follows:

(SEQ ID No. 34)
NNNPQQGNPNQGGNNGGGNQGGGNGG

PCR is performed with the following primers:

29315

5' GATCTAGCTAGCAACAATAACCCCCAGCAGGGCAACCCCAACCAGGGCGGGAACAACGGC 3'    (SEQ ID No. 35)

29316

5' GATCTAGCTAGCGCCGCCGTTGCCGCCGCCCTGGTTGCCGCCGCCGTTGTTCCCGCCCTG 3'    (SEQ ID No. 36)

EXAMPLE 4

This example describes the construction of fusion proteins (enzyme hybrid) from a lipase (Lipolase™; Humicola lanuginosa lipase) and a CBD. A construction with an N-terminal CBD was chosen, since the N-terminal of the enzyme is far from the active site, whereas the C-terminal is in relatively close proximity to the active site.

pIVI450 construction (CBD-linker-lipase)

This construct was made in order to express a protein having the Myceliophthora thermophila cellulase CBD and linker at the N-terminal of Lipolase™.

A PCR fragment was created using the clone pA2C161 (DSM 9967) containing the M. thermophila cellulase gene as template, and the following oligomers as primers:

8202

(SEQ ID No. 32)
5' ACGTAGTGGCCACGCTAGGCGAGGTGGTGG 3'

The PCR fragment is cut with NheI, the vector pIVI450 CBD-NheI-Lipolase™ is likewise cut with NheI, and the two fragments are ligated, creating: pIVI450 CBD-Nonglycosylated linker-Lipolase™ (SEQ ID No. 10).

Introduction of H. insolens family 45 cellulase linker

The protein expressed from the construct described here contains a construction of the type: CBD-glycosylated linker-lipase.

The amino acid sequence of the linker is as follows:

(SEQ ID No. 37)
VQIPSSSTSSPVNQPTSTSTTSTSTTSSPPVQPTTPS

PCR is performed with the following primers:

29313

(SEQ ID No. 38)
5' GATACTGCTAGCGTCCAGATCCCCTCCAGC 3'

29314

(SEQ ID No. 39)
5' GATACTGCTAGCGCTGGGAGTCGTAGGCTG 3'

The PCR fragment is cut with NheI, the vector pIVI450 CBD-NheI-Lipolase™ is likewise cut with NheI, and the two fragments are ligated, creating: pIVI450 CBD-H. insolens family 45 cellulase linker-Lipolase™ (SEQ ID No. 11).

EXAMPLE 5

This example concerns fusion proteins comprising a CBD linked to *Coprinus cinereus* peroxidase (CiP) or to a mutant thereof (mCiP842) (see, e.g., WO 95/10602).

Yeast expression system

The pJC106/YNG344 host/vector system was chosen as the standard expression system for all CiP experiments utilizing yeast expression. Mutant mCiP842 contains the following amino acid substitutions relative to the parent CiP: V53A, E239G, Y272F, M242I. Constructions using this plasmid were performed with the same procedure as was used for the fusion of CBD to the wild type CiP gene.

Construction of the CBD-CiP fusion vector JC20A or JC20D: CiP signal seq.-*H. insolens* family 45 cellulase CBD-*H. insolens* family 45 cellulase linker-CiP or -mCiP842

The CBD-CiP fusion was constructed by amplifying four separate gene fragments using PCR. A) The CiP 5'-untranslated region and the CiP coding sequence from plasmid JC106 or mCiP842 encoding amino acids 1 to 22, B) the *H. insolens* family 45 cellulase CBD from plasmid pCaHj418 encoding amino acids 248–305, C) the *H. insolens* family 45 cellulase linker domain from plasmid pCaHj418 encoding amino acids 213–247, and D) the CiP coding sequence from plasmid JC106 or mCiP842 encoding amino acids 21 to 344.

The sequence of the *H. insolens* family 45 cellulase is disclosed in WO 91/17244.

Primers used in amplifications A through D were as follows:

```
Amplification A:

1. CiPpcrdwn:    CCCCCTTCCCTGGCGAATTCCGCATGAGG           (SEQ ID No. 40)

2. JC20.1:       ACCTTGGGGTAGAGCGAGGGCACCGATG            (SEQ ID No. 41)

Amplification B:

3. JC20.2:       TGCACTGCTGAGAGGTGGGC                    (SEQ ID No. 42)

4. JC20.3:       CAGGCACTGATGATACCAGT                    (SEQ ID No. 43)

Amplification C:

5. JC20.4:       CCCTCCAGCAGCACCAGCTCT                   (SEQ ID No. 44)

6. JC20.5:       TCCTCCAGGACCCTGACCGCTCGGAGTCGTAGGCTG    (SEQ ID No. 45)

Amplification D:

7. JC20.6:       TACGACTCCGAGCGGTCAGGGTCCTGGAGGAGGCGGG   (SEQ ID No. 46)

8. YES2term:     GGGAGGGCGTGAATGTAAG                     (SEQ ID No. 47)
```

Amplified products of reactions A) and B) were purified and phosphorylated using T4 polynucleotide kinase, ligated to one another for 15 min. at room temperature, and amplified with primers 1 and 4 to generate product AB. Amplified products of reactions C) and D) were purified and mixed, then PCR-amplified to generate product CD. Reaction products AB and CD were purified and phosphorylated using T4 polynucleotide kinase, ligated to one another for 15 min. at room temperature, and amplified with primers 1 and 8 to generate the final product. The resulting product was purified, mixed with plasmid JC106 which had the CiP gene removed by digestion with BamHI and XhoI. Plasmid JC20A contains the wild type CiP gene, whereas plasmid JC20D contains the peroxide-stable mutant mCiP842. Transformants were selected on minimal media lacking uridine.

Construction of the other CBD-CiP fusion vectors JC21, 22, 23

Other plasmids containing alternate linkers between the *H. insolens* family 45 cellulase CBD and CiP were constructed in essentially the same way as described for plasmid JC20A above, using PCR and overlap extension. The resulting plasmids encode fusion proteins with the following domain compositions:

JC21: CiP signal seq.-truncated *H. insolens* family 45 cellulase CBD-*H. insolens* family 45 cellulase linker-CiP JC22: CiP signal seq.-*H. insolens* family 45 cellulase CBD-linker from the NifA gene of *Klebsiella pneumoniae*-CiP JC23: CiP signal seq.-*H. insolens* family 45 cellulase CBD-linker from the *E. coli* OmpA gene-CiP.

Scoring of transformants for peroxidase and cellulose-binding activity

Plate Assay: Yeast transformants were grown on minimal media plates containing 2% galactose (to induce the GAL1 yeast promoter driving CBD-CiP expression) that had been covered with a double filter layer consisting of cellulose acetate on top of nitrocellulose. After overnight growth, both filters were washed twice with 100 ml of 20 mM phosphate buffer, pH 7.0 for 5 minutes, after which no colony debris could be detected. Filters were then assayed for bound peroxidase activity by coating them with a 100 mM phosphate buffer, pH 7.0, containing 50 µg/ml of diaminobenzidine and 1 mM hydrogen peroxide. Bound peroxidase activity appears as a brown precipitate on the filter.

Liquid Assay: Liquid cultures of mutants demonstrating cellulose binding in the filter assay were grown overnight in minimal media containing 2% galactose. 20 µl samples of culture broth were mixed with Avicel crystalline cellulose (20 g/L) in 0.1 M phosphate buffer, pH 7, 0.01% Tween 20 in a total volume of 100 µl and incubated at 22° C. for 10 minutes. The mixture was then centrifuged to pellet the insoluble cellulose fraction, and the supernatants were assayed for peroxidase activity using the standard CiP assay (see, e.g, WO 95/10602). Binding was scored as the % activity bound to the insoluble cellulose fraction based on the decrease in soluble activity.

High pH/thermal stability screening of CBD-CiP fusions

This screening process utilizes broth samples from yeast cultures grown in microtiter plates. The 96-well plate screen is performed by first growing yeast transformants of a pool of mutants in 50 μL volumes of URA(-) medium, pH 6.0 in 96-well microtiter plates. Cultures are inoculated by dilution into medium and pipetting (robotic or manual autopipettor) into 96-well plates. These are placed in an incubator set at 30° C., 350 RPM and shaken for approximately 5 days. Plates are placed directly from the culture box onto the robotic system.

Both CiP and mCiP842 and the related fusion proteins were subjected to a combined pH—temperature—$H_2O_2$ stress test: After an initial activity assay, cultures are diluted to ca. 0.06 PODU/ml (see WO 95/10602 for definition of PODU) and incubated in 200 μM hydrogen peroxide, 100 mM phosphate/borate buffer, pH10.5 at 50° C. After 0, 10, 20 and 30 minutes, samples are removed and residual activity is measured using the standard ABTS assay, pH 7.0. Improved mutants are those showing higher residual activity than CiP and are expressed as percent residual activity relative to the time 0 assay result.

Yeast expression plasmids designed to make five *H. insolens* family 45 cellulase CBD-CiP fusions were constructed and sequenced. The primary difference between the fusions is in the type of linker domain that connects the CBD to the CiP, as this was thought to be important for maximizing the binding of the CBD to cellulosic substrates.

All the constructs encode a fusion of four discrete domains: CiP signal sequence-*H. insolens* family 45 cellulase CBD-linker-CiP. Plasmid JC20A is a CBD-CiP fusion to the wild type CiP, while plasmid JC20D is a fusion to the stable mutant mCiP842 containing the amino acid substitutions V53A, E239G, M2421 and Y272F. Both JC20 constructs contain the natural *H. insolens* family 45 cellulase linker domain. Plasmid JC21 encodes a fusion protein identical to the JC20 product with the exception that it contains a truncated linker lacking residues 7 to 23 of the *H. insolens* family 45 cellulase linker. Plasmid JC22 has the *H. insolens* family 45 cellulase linker domain replaced with a 12 residue proline-rich linker from the outer membrane protein of *E. coli* (from the OmpA gene). The final plasmid, JC23, contains a fourth linker (called a Q linker) derived from the NifA gene of *Klebsiella pneumoniae*. This linker, 14 amino acids in length, contains 3 glutamine residues (hence the name Q linker) as well as 3 arginine residues, giving it a positive charge at neutral pH.

These JC20-series plasmids were transformed into *S. cerevisae* for expression and testing. After transformation, yeast colonies were grown on selective plates covered with a double filter layer: cellulose acetate filters on top of nitrocellulose. Wild type CiP secreted from yeast JC106 and the stable mutant mCiP842 pass through the cellulose acetate, then binds to the nitrocellulose where it can be visualized using diaminobenzidine (DAB) and $H_2O_2$. The cellulose acetate filter does not bind any wild-type or mCiP842 peroxidase. In contrast, the N-terminal CBD-CiP fusions encoded by plasmids JC20A, JC20D, JC21, JC22, and JC23 are all detectable on both filters using the DAB assay, indicating that the fusion proteins have both peroxidase and cellulose-binding activities. Visual inspection of filters suggests that the NifA linker may improve binding slightly over the others, although the difference is marginal. In all cases the peroxidase activity bound to the cellulose acetate filter remains bound even after washing extensively with buffer at pH 7. The activity bound to the lower nitrocellulose filter suggests that binding of the CBD-CiP may be incomplete, or the cellulose filter gets saturated, allowing some of the fusion protein to pass through to the lower filter, or that some percentage of the fusion protein gets truncated to include only the peroxidase domain.

Sequence identifiers herein corresponding to the constructs are as as indicated below. Abbreviations are as follows:

EGV: *Humicola insolens* family 45 endoglucanase (cellulase)
CiPss: CiP signal sequence
CiP842: CiP mutant/variant mCiP842;
SEQ ID No. 12: Nucleotide sequence of the CiPss(+2 amino acids)-EGV CBD-EGV linker-CiP fusion in JC20.A;
SEQ ID No.13: Nucleotide sequence of the CiPss(+2 amino acids)-EGV CBD-EGV linker-CiP842 fusion in JC20.D1;
SEQ ID NO. 14: Nucleotide sequence of the CiPss(+2 amino acids)-EGV CBD-truncated EGV linker-CiP fusion in JC21;
SEQ ID No. 15: Nucleotide sequence of the CiPss(+2 amino acids)-EGV CBD-*E. coli* OmpA linker-CiP fusion in JC22;
SEQ ID No. 16: Nucleotide sequence of the CiPss(+2 amino acids)-EGV CBD-NifA linker-CiP fusion in JC23.

EXAMPLE 6

This example concerns fusion proteins comprising a CBD linked to *Myceliophthora thermophila* laccase (MtL) (MtL is described in, e.g., WO 95/33836).

Construction of the N-terminal MtL-CBD fusion pJC24

A DNA fragment containing the *Coprinus cinereus* peroxidase (CiP) signal sequence (22 amino acids), the *H. insolens* family 45 cellulase CBD (37 amino acids) and a NifA linker domain from *Klebsiella pneumoniae* (14 amino acids) was PCR-amplified using two specific primers to plasmid pJC23.

| primer name | sequence |
| --- | --- |
| CiPpcrdwn: | CTGGGGTAATTAATCAGCGAAGCGATG (SEQ ID No. 48) |
| JC24.1 | AGCGCGTGGACGTTCGATGC (SEQ ID No. 49) |

PCR amplification was performed using Pwo polymerase (Boehringer Mannheim) using the supplied buffer according to the manufacturer's instructions. The reaction was initiated after 3 min. at 96° C. by addition of the polymerase, and allowed to cycle 30 times with 30 sec at 96° C., 30 sec at 60° C. and 2 min at 72° C.

A second PCR fragment encoding the mature MtL peptide lacking both the signal peptide and propeptide (residues 48–620) was PCR amplified from a cDNA clone of the Myceliophthora laccase contained in plasmid pJRoC30. PCR amplification was performed using the same conditions as described above and the following primer pair:

| primer name | sequence | |
| --- | --- | --- |
| JC24.2 | CAGCAGAGCTGCAACACCCCCAG | (SEQ ID No. 50) |
| YES2term | GGGGAGGGCGTGAATGTAAG | (SEQ ID No. 51) |

Following amplification, both DNA fragments were purified using the QiaQuick™ Spin purification kit (Qiagen, Inc.) according to the manufacturer's recommendations. The two DNA fragments were then ligated together and a portion of the ligation mix used as a template for PCR amplification using the CiPpcrdwn and YES2term primers under the same conditions as described above. The resulting 2.3 kb chimeric DNA fragment was gel-purified, cut with BamHI and NotI restriction enzymes, and ligated into the vector backbone of plasmid pJC106 to obtain plasmid pJC24.

Construction of the C-terminal MtL-CBD fusion pJC25

A PCR fragment encoding the entire MtL peptide (residues 1–620) and 232 bp of upstream sequence was amplified from plasmid pJRoC30 using the following primer pair:

| primer name | sequence |
|---|---|
| CiPpcrdwn: | CTGGGGTAATTAATCAGCGAAGCGATG (SEQ ID No. 52) |
| JC25.2 | CGCCTTGACCAGCCACTCGCCCTCCTCG (SEQ ID No. 53) |

A second DNA fragment encoding the H. insolens family 45 cellulase linker domain (35 amino acids), the H. insolens family 45 cellulase CBD (37 amino acids) and 20 bp of 3' non-coding sequence was amplified from the H. insolens family 45 cellulase plasmid pCaHj418 using the following primer pair:

| primer name | sequence |
|---|---|
| JC20.4 | CCCTCCAGCAGCACCAGCTCTC (SEQ ID No. 54) |
| JC25.1NotI | ATAAGAATGCGGCCGCCTACAGGCACTGATGGTACCAGT (SEQ ID No. 55) |

The two DNA fragments were ligated briefly and the full-length 2.3 kb fusion product was amplified as described above, using the primers CiPpcrdwn and JC25.1NotI. This final PCR product was cloned into plasmid pJC106 to obtain plasmid pJC25.

Construction of the C-terminal MtL-CBD fusion pJC26

Plasmid pJC26 was constructed in exactly the same manner as pJC25, except that primer ML-ct was substituted for primer JC25.1 and resulted in a truncated product of the MtL gene lacking the final 17 codons.

| primer name | sequence |
|---|---|
| ML-ct | CAGCAGAGCTGCAACACC |

Sequence identifiers herein corresponding to the constructs are as as indicated below. Abbreviations are as follows:

EGV: *Humicola insolens* family 45 endoglucanase (cellulase)
CiPss: CiP signal sequence
MtLss: MtL signal sequence
SEQ ID No. 17: Nucleotide sequence of the CiPss(+2 amino acids)-EGV CBD-NifA linker-MtL fusion in pJC24;
SEQ ID No. 18: Nucleotide sequence of the MtLss-MtL propeptide-MtL-EGV linker-EGV CBD fusion in pJC25;
SEQ ID No. 19: Nucleotide sequence of the MtLss-MtL propeptide-MtL (minus 17 amino acids)-EGV linker-EGV CBD fusion in pJC26. The codons corresponding to the 17 amino acids in question are shown in bold in SEQ ID No. 18.

We claim:

1. A process for removal or bleaching of soiling or stains present on cellulosic fabric, comprising contacting the fabric in an aqueous medium with an enzyme hybrid which comprises a catalytically active amino acid sequence of a non-cellulolytic enzyme linked to an amino acid sequence comprising a cellulose-binding domain, wherein:

(i) the catalytically active amino acid sequence is derived from an enzyme selected from the group consisting of amylases, proteases, lipases, pectinases and oxidoreductases, wherein the amylase is derived from a species of Bacillus, Thermoanaerobactor, or Thermoanaerobacterium; the protease is derived from a species of Bacillus or Fusarium; the lipase is derived from a species of Humicola, Rhizomucor, Penicillium, Geotricum, Rhizopus, Fusarium, Candida, Pseudomonas or Bacillus; and the oxidoreductase is selected from the group consisting of a peroxidase and a laccase, wherein the peroxidase is derived from a species of Coprinus, Fusarium, Humicola, Tricoderma, Myrothecium, Verticillum, Arthromyces, Caldariomyces, Ulocladium, Embellisia, Cladosporium, Dreschlera, Phanerochaete, Coriolus, Trametes, Rhizopus, Mucor, Streptomyces, Streptoverticillum, Bacillus, Rhodobacter, Rhodomonus, Streptococcus, or Pseudomonas and the laccase is derived from a species of Trametes, Aspergillus, Neurospora, Podospora, Botrytis, Collybia, Fomes, Lentinus, Pleurotus, Rhizoctonia, Coprinus, Psatyrella, Phlebia, Pyricularia, Rigidoporus, Myceliophthora, Schytalidium or Polyporus; and (ii) the cellulose-binding domain is derived from an enzyme selected from the group consisting of cellulases, xylanases, mannanases, arabinofuranosidases, acetylesterases, and chitinases.

2. The process according to claim 1, wherein the soiling or stain originates from starch, protein, fat, soil, clay, fruit, vegetables, coffee, tea, spices, red wine, body fluids, grass or ink.

3. The process according to claim 2, wherein the amylase is derived from *Bacillus licheniformis*.

4. The process according to claim 3, wherein the peroxidase is derived from *C. cinereus*.

5. The process according to claim 1, wherein the enzyme hybrid is obtained by a method comprising growing a transformed host cell containing an expression cassette which comprises a DNA sequence encoding the enzyme hybrid, whereby the enzyme hybrid is expressed.

6. A detergent composition comprising an enzyme hybrid which comprises:

(a) a catalytically active amino acid sequence of a non-cellulolytic enzyme linked to an amino acid sequence comprising a cellulose-binding domain, wherein (i) the catalytically active amino acid sequence is derived from an enzyme selected from the group consisting of amylases, proteases, lipases, pectinases and oxidoreductases, wherein the amylase is derived from a species of Bacillus, Thermoanaerobactor, or Thermoanaerobacterium; the protease is derived from a species of Bacillus or Fusarium; the lipase is derived from a species of Humicola, Rhizomucor, Penicillium, Geotricum, Rhizopus, Fusarium, Candida, Pseudomonas or Bacillus; and the oxidoreductase is selected from the group consisting of a peroxidase and a laccase, wherein the peroxidase is derived from a species of Coprinus, Fusarium, Humicola, Tricoderma, Myrothecium, Verticillum, Arthromyces, Caldariomyces, Ulocladium, Embellisia, Cladosporium, Dreschlera, Phanerochaete, Coriolus, Trametes, Rhizopus, Mucor, Streptomyces, Streptoverticillum, Bacillus, Rhodobacter, Rhodomonus, Streptococcus, or Pseudomonas, and the laccase is derived from a species of Trametes, Aspergillus, Neurospora, Podospora, Botrytis, Collybia, Fomes, Lentinus, Pleurotus, Rhizoctonia, Coprinus, Psatyrella, Phlebia, Pyricularia, Rigidoporus, Myceliophthora, Schytalidium or Polyporus; and (ii) the cellulose-binding domain is derived from an enzyme selected from the group consisting of cellulases, xylanases, mannanases, arabinofuranosidases, acetylesterases, and chitinases; and (b) a surfactant.

7. A process for washing soiled or stained cellulosic fabric, comprising washing the fabric in an aqueous medium with a detergent composition according to claim 6.

8. An enzyme hybrid encoded by a hybrid-encoding DNA sequence comprising a sequence contained in a DNA sequence selected from the group consisting of SEQ ID No. 1, SEQ ID No. 5, SEQ ID No. 7, SEQ ID No. 9, SEQ ID No 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18 and SEQ ID No. 19.

9. An enzyme hybrid according to claim 8 having an amino acid sequence comprising an amino acid sequence selected from the group consisting of SEQ ID No. 2, SEQ ID No. 6 and SEQ ID No. 8.

10. A process for removal or bleaching of soiling or stains present on cellulosic fabric, comprising contacting the fabric in an aqueous medium with an enzyme hybrid which comprises a catalytically active amino acid sequence of a non-cellulolytic enzyme linked to an amino acid sequence comprising a cellulose-binding domain, wherein said enzyme hybrid is selected from the group consisting of:

(a) a polypeptide comprising an amino acid sequence selected from the group consisting of SEQ ID NO:2, SEQ ID NO:6, and SEQ ID NO:8; and (b) a polypeptide encoded by a DNA sequence selected from the group consisting of SEQ ID NO:9, SEQ ID NO: 10, SEQ ID NO:11, SEQ ID NO: 12, SEQ ID NO:13, SEQ ID NO:14, SEQ ID NO:15, SEQ ID NO:16, SEQ ID NO:17, SEQ ID NO:18,and SEQ ID NO:19.

11. A detergent composition as defined in claim 6, wherein said enzyme hybrid is selected from the group consisting of:

(a) a polypeptide comprising an amino acid sequence selected from the group consisting of SEQ ID NO:2, SEQ ID NO:6, and SEQ ID NO:8; and (b) a polypeptide encoded by a DNA sequence selected from the group consisting of SEQ ID NO: 9, SEQ ID NO: 10, SEQ ID NO:11, SEQ ID NO: 12, SEQ ID NO:13, SEQ ID NO:14, SEQ ID NO:15, SEQ ID NO: 16, SEQ ID NO:17, SEQ ID NO:18,and SEQ ID NO:19, and (b) a surfactant.

* * * * *